US011732008B2

(12) United States Patent
Deming et al.

(10) Patent No.: US 11,732,008 B2
(45) Date of Patent: Aug. 22, 2023

(54) PREPARATION OF FUNCTIONAL HOMOCYSTEINE RESIDUES IN POLYPEPTIDES AND PEPTIDES

(71) Applicant: The Regents of the University of California, Oakland, CA (US)

(72) Inventors: Timothy J. Deming, Los Angeles, CA (US); Eric G. Gharakhanian, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 366 days.

(21) Appl. No.: 16/096,951

(22) PCT Filed: Apr. 27, 2017

(86) PCT No.: PCT/US2017/029867
§ 371 (c)(1),
(2) Date: Oct. 26, 2018

(87) PCT Pub. No.: WO2017/189860
PCT Pub. Date: Nov. 2, 2017

(65) Prior Publication Data
US 2019/0119322 A1    Apr. 25, 2019

Related U.S. Application Data

(60) Provisional application No. 62/328,394, filed on Apr. 27, 2016.

(51) Int. Cl.
| | |
|---|---|
| *C07K 7/06* | (2006.01) |
| *C07K 14/00* | (2006.01) |
| *C08G 69/10* | (2006.01) |
| *C07K 1/113* | (2006.01) |
| *C07K 1/107* | (2006.01) |
| *C07K 1/00* | (2006.01) |
| *C08G 69/48* | (2006.01) |

(52) U.S. Cl.
CPC .............. *C07K 7/06* (2013.01); *C07K 1/006* (2013.01); *C07K 1/107* (2013.01); *C07K 1/113* (2013.01); *C07K 1/1133* (2013.01); *C07K 14/001* (2013.01); *C08G 69/10* (2013.01); *C08G 69/48* (2013.01)

(58) Field of Classification Search
None
See application file for complete search history.

(56) References Cited

U.S. PATENT DOCUMENTS

| | | | |
|---|---|---|---|
| 4,165,332 | A | 8/1979 | Beard et al. |
| 5,599,903 | A | 2/1997 | Kauvar et al. |
| 7,132,475 | B2 | 11/2006 | Hubbell et al. |
| 9,718,921 | B2 | 8/2017 | Deming et al. |
| 10,351,591 | B2 | 7/2019 | Deming et al. |
| 10,526,396 | B2 | 1/2020 | Lecommandoux et al. |
| 2010/0222407 | A1 | 9/2010 | Segura et al. |
| 2011/0177508 | A1 | 7/2011 | Bestor et al. |
| 2011/0223217 | A1 | 9/2011 | Dixon et al. |
| 2014/0294932 | A1 | 10/2014 | Kim et al. |
| 2019/0119322 | A1 | 4/2019 | Deming et al. |

FOREIGN PATENT DOCUMENTS

| | | |
|---|---|---|
| CN | 104926924 A | 9/2015 |
| EP | 0226827 A2 | 7/1987 |
| EP | 0761203 A1 | 3/1997 |
| EP | 1712557 A1 | 10/2006 |
| JP | 2004/231633 A | 8/2004 |
| WO | WO-96/40757 A2 | 12/1996 |
| WO | WO-2009/151708 A2 | 12/2009 |
| WO | WO-2010/023670 A2 | 3/2010 |
| WO | WO-2013/082116 A1 | 6/2013 |
| WO | WO-2013/148727 A1 | 10/2013 |
| WO | WO2016/154120 | 3/2016 |
| WO | WO-2017/021334 A1 | 2/2017 |
| WO | WO-2017189860 A1 | 11/2017 |
| WO | WO-2022/261181 | 12/2022 |

OTHER PUBLICATIONS

Kramer, Multimodal Switching of Conformation and Solubility in Homocysteine Derived Polypeptides, J. Am. Chem. Soc. 2014, 136, 5547-5550 (Year: 2014).*
Brown et al., "Strategy for "Detoxification" of a Cancer-Derived Histone Mutant Based on Mapping Its Interaction with the Methyltransferase PRC2," Journal of The American Chemical Society, 136(39):13498-13501 (2014).
Extended European Search Report for EP Application No. EP 17790439 dated Nov. 13, 2019.
Jamonnak et al., "Substrate specificity of SIRT1-catalyzed lysine $N^\epsilon$-deacetylation reaction probed with the side chain modified $N^\epsilon$-acetyl-lysine analogs," Bioorganic Chemistry, 38(1):17-25 (2010).
Weeden et al., "Aretro-inverso α-melanocyte stimulating hormone analog with MC1R-binding selectivity," Journal of Peptide Science, 17:47-55 (2011).
Kramer et al., "Reversible chemoselective tagging and functionalization of methionine containing peptides," Chemical Communications, 49:5144-5146 (2013).
Roemmele et al., "Chirospecific synthesis of beta-hydroxy alpha-amino acids," The Journal of Organic Chemistry, 54(8): 1866-1875 (1989).
Ross et al., "A straightforward preparation of primary alkyl triflates and their utility in the synthesis of derivatives of ethidium," Journal of the Chemical Society Perkins Transactions 1, 1(4): 571-574 (2000).
Notice of Allowance and Fees Due for U.S. Appl. No. 15/559,981 dated Feb. 25, 2019.

(Continued)

*Primary Examiner* — Thomas S Heard
(74) *Attorney, Agent, or Firm* — Foley Hoag LLP; David P. Halstead; Janine S. Ladislaw

(57) ABSTRACT

Methodology was developed for transformation of methionine residues into homocysteine derivatives. Methionine residues can undergo alkylation reactions at low pH to yield sulfonium ions, which can then be selectively demethylated to give alkyl homocysteine residues. This process tolerates many functional groups.

14 Claims, 15 Drawing Sheets

Figure 1:
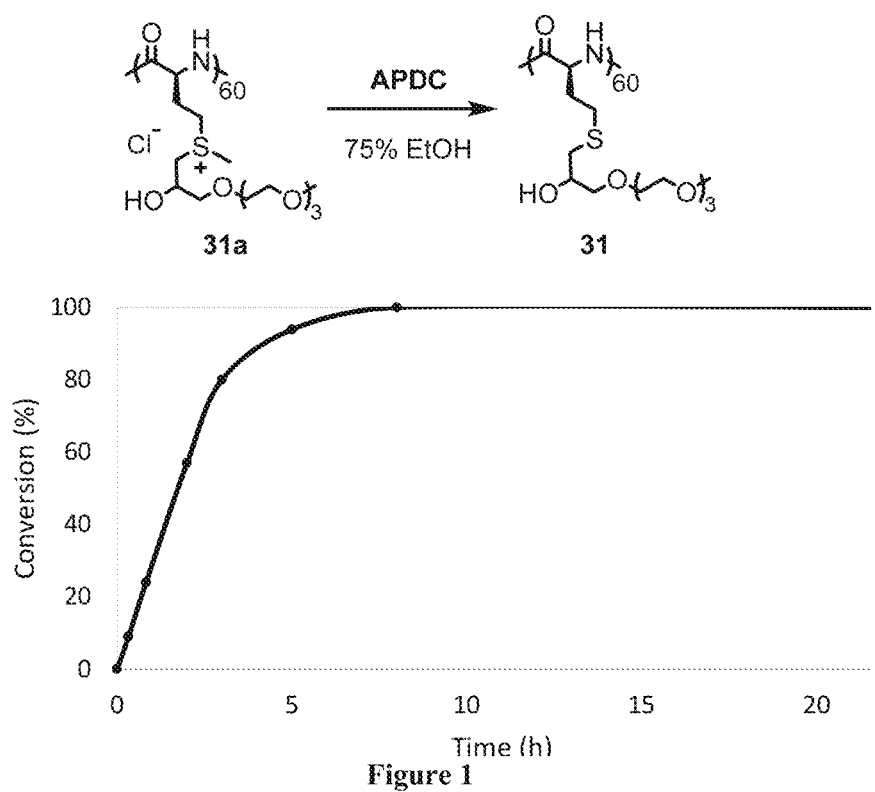

Specification includes a Sequence Listing.

(56) References Cited

OTHER PUBLICATIONS

Chilkoti et al., "Targeted drug delivery by thermally responsive polymers," Advanced Drug Delivery Reviews, 54(5): 613-630 (2002).
Urry et al., "Temperature of polypeptide inverse temperature transition depends on mean residue hydrophobicity," Journal of the American Chemical Society, 113(11): 4346-4348 (1991).
U.S. Appl. No. 14/388,777, Abandoned.
U.S. Appl. No. 14/770,417, Granted.
U.S. Appl. No. 15/559,981, Granted.
U.S. Appl. No. 15/748,806, Granted.
Hayakawa, T. et al., "Syntheses and conformational studies of poly (S-aminoalkyl-homocysteine)s and their benzyloxycarbonyl derivatives", Polymer Journal, 7(5): pp. 538-543 (1975).
International Search Report and Written Opinion for International Application No. PCT/US22/032637 dated Oct. 12, 2022.
Alferiev et al., "High reactivity of alkyl sulfides towards epoxides under conditions of collagen fixation—a convenient approach to 2-amino-4-butyrolactones," Biomaterials, 22(18):2501-2506 (2001).
Catalog page for 2 bromoethyl triflate from ABX, http://web.archive.org/web/20090706013707/http://abx.de/chemicals/6182.html, available online Jul. 2009.
Extended European Search Report issued by the European Patent Office, dated Jan. 28, 2016, in related Application No. EP 15306247.
Gharakhanian et al., "Chemoselective synthesis of functional homocysteine residues in polypeptides and peptides," Chem Commun, 52(30): 5336-5339 (2016).
Gharakhanian et al., "Role of side-chain molecular features in tuning lower critical solution temperatures (LCSTs) of oligoethylene glycol modified polypeptides," J Phys Chem B, 120(26): 6096-6101 (2016).
Gharakhanian et al., "Versatile Synthesis of Stable, Functional Polypeptides via Reaction with Epoxides," Biomacromolecules, 16(6):1802-1806 (2015).
Hanson et al., "Nonionic block copolypeptide micelles containing a hydrophobic rac-leucine core," Macromolecules, 43(15):6268-6269 (2010).
Huang et al., "Biologically active polymersomes from amphiphilic glycopeptides," J Am Chem Soc, 134:119-22 (2011).
International Search Report and Written Opinion for International Application No. PCT/EP2016/068232 dated Nov. 14, 2016.
International Search Report and Written Opinion for International Application No. PCT/US2013/033938 dated Jul. 22, 2013.
International Search Report and Written Opinion for International Application No. PCT/US2017/029867 dated Jul. 20, 2017.
International Search Report from corresponding International Application No. PCT/US2014/018763, dated Jun. 2, 2014.
International Search Report from corresponding International Application No. PCT/US2016/023428, dated Jun. 29, 2016.
Kaplowitz, et al., "The importance and regulation of hepatic glutathione," Yale J Biol Med, 54: 497-502 (1981).
Kramer et al., "Glycopolypeptide conformations in bioactive block copolymer assemblies influence their nanoscale morphology," Soft Matter, 9(12):3389-95 (2013).
Kramer, Jessica R., et al. "Preparation of Multifunctional and Multireactive Polypeptides via Methionine Alkylation," Biomacromolecules, 13: 1719-23 (2012).
Kultyshev, et al., "S-Alkylation and S-Amination of Methyl Thioethers—Derivative of closo-[B12H12]2-. Synthesis of a Boronated Phosphonate, gem-Bisposphonates, and Dodecaborane-ortho-carborane Oligomers," J Am Chem Soc, 124(11): 2614-2624 (2002).
Kyte, et al., "Purification of peptides that contain methionine residues," Method Enzymol, 91: 367-377 (1983).
March, Jerry Advanced Organic Chemistry (1992) ISBN 0-471-60180-2, p. 294-298 and p. 352-354.
Pande, et al., "Suppression of phase separation in solutions of bovine lambda IV-crestallin by polar modification ofthe sulfur-containing amino acids," PNAS, 88(11): 4916-4920 (1991).
Reid, et al., "Selective identification and quantitative analysis of methionine containing peptides by charge derivatization and tandem mass spectrometry," J Am Soc Mass Spectr, 16(7): 1131-1150 (2005).
Ribeiro et al., "Influence ofthe amino-acid sequence on the inverse temperature transition of elastin-like polymers," Biophys J, 97:312-20 (2009).
Stark, et al., "Alkylation ofthe methionine residues of ribonuclease in 8M urea," J Biol Chem, 269(11): 3755-3761 (1964).
Storer, et al., "Aracyl triflates for preparing fluorescent and UV absorbing derivatives of unreactive carboxylates, amines, and other reactive metabolites," Analytica Chimic Acta, 558: 319-325 (2006).
Supplementary European Search Report dated Sep. 16, 2016 from EP 14 75 7627.
Taichi, et al., "Suppression of side reactions during final deprotection employing a strong acid in boc chemistry: regeneration of methionyl residues from their sulfonium salts," Int J Peptide Res Ther, 15(4): 247-253 (2009).
Teeuwen et al., "'Clickable' elastins: elastin-like polypeptides functionalized with azide or alkyne groups," Chem Comm, 4022-4 (2009).
Toennies, et al., "Methionine Studies VII. Sulfonium Derivatives," Journal ofthe American Chemical Society, vol. 67, 1945, pp. 849-851.
Umemura, et al., "Alylation of several nucleophiles with alkylsulfonium salts," Bull Chem Soc Japan, 63: 2593-2600 (1990).

* cited by examiner

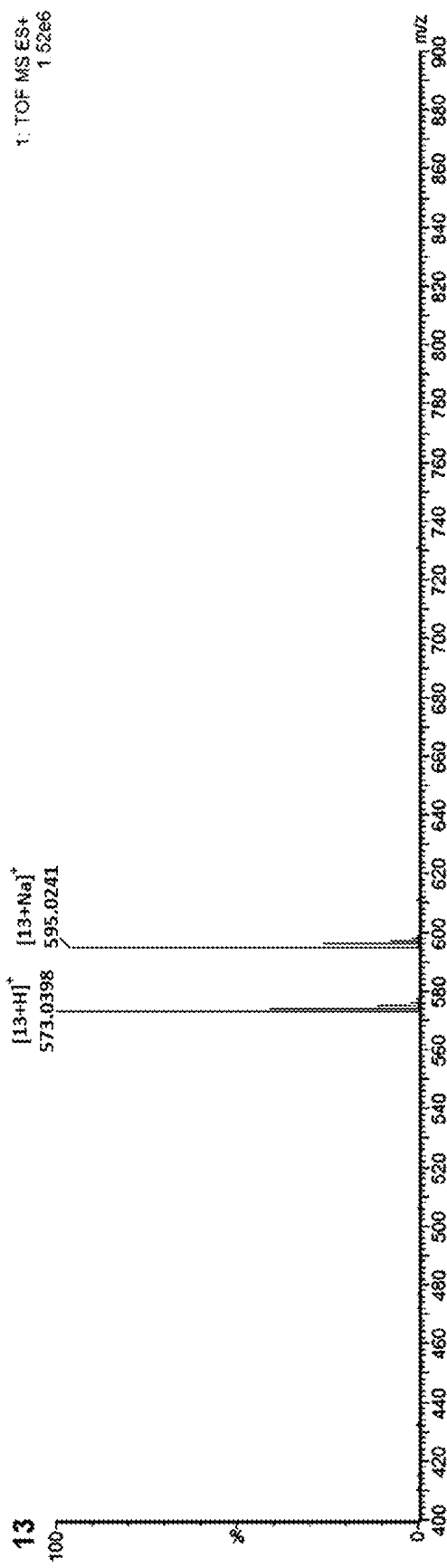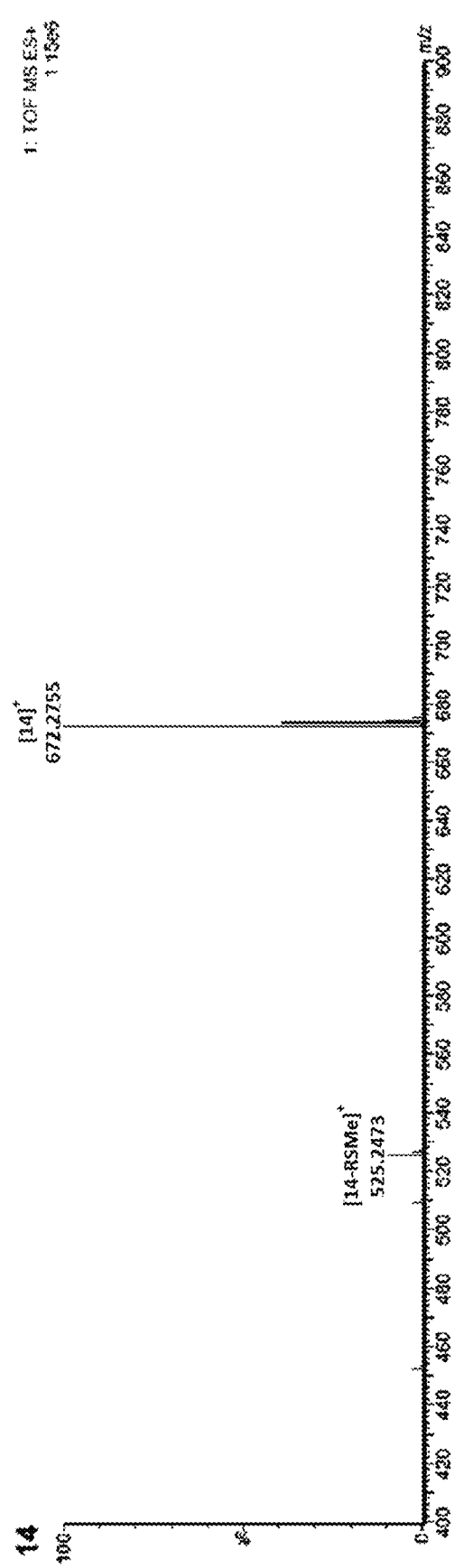
Figure 5A
Figure 5B

PREPARATION OF FUNCTIONAL HOMOCYSTEINE RESIDUES IN POLYPEPTIDES AND PEPTIDES

RELATED APPLICATIONS

This application is a national stage filing under 35 U.S.C. 371 of International Application PCT/US2017/029867, filed Apr. 27, 2017 which claims the benefit of, and priority to, U.S. Provisional Application No. 62/328,394, filed Apr. 27, 2016. The contents of the international application are hereby incorporated by reference in their entirety.

STATEMENT REGARDING FEDERALLY SPONSORED RESEARCH OR DEVELOPMENT

This invention was made with government support under Grant Number 1412367, awarded by the National Science Foundation. The government has certain rights in the invention.

SEQUENCE LISTING

The instant application contains a Sequence Listing which has been submitted electronically in ASCII format and is hereby incorporated by reference in its entirety. Said ASCII copy, created on Aug. 27, 2020, is named UCH-09201_SL.txt and is 2,219 bytes in size.

BACKGROUND OF THE INVENTION

Practical methods for selective conversion of natural amino acids in peptides, polypeptides and proteins into different functional residues are desirable for many areas including chemical biology, materials science, and pharmaceuticals. The introduced functionality can provide probes for tracking, mimicking of post-translational modifications, or a means to adjust biological and physical properties of biomacromolecules. Both biological and chemical synthesis methods have been developed to either replace or convert natural residues using highly selective processes. In order to introduce functionality at unique sites, it is essential that the natural residues are present in low abundance, which has focused much attention on cysteine, methionine, and N-terminal residues. Most chemical strategies focus on the modification of highly nucleophilic cysteine residues. While many excellent methods are available for chemoselective cysteine modification, some are potentially limited by racemization and moderate yields. Previously, M residues, mainly as the amino acid, have been converted to R—$C^H$ analogs through use of Na/NH$_3$, which is incompatible with some functional groups and can lead to racemization, resulting in this method being rarely used for peptides.

Additionally, polymers that respond to temperature in solution, especially in aqueous media, have received much attention for a variety of applications such as stimulus-responsive assemblies, and as materials for potential use in medicine. Double hydrophilic block copolymers containing a thermoresponsive segment, i.e. possessing a lower critical solution temperature (LCST), are able to transform from solutions in water into hydrogels or suspensions of nanoparticles upon heating to above the LCST. In recent years there has been considerable development of new polymers that possess LCSTs in water, primarily based on repeats bearing short oligoethylene glycol (OEG) side-chains. Initial efforts in this area focused on polymethacrylates and polyacrylates containing OEG side-chain groups, and now this motif has been used to prepare other types of thermoresponsive polymers, such as OEG containing polypeptides.

Thermoresponsive polypeptides are desirable compared to other polymers since they can degrade in living systems, which is advantageous for biological and medical applications. OEG containing thermoresponsive polypeptides have been prepared using a variety of methods, using different core amino acid residues, and also with a wide range in number of ethylene glycol (EG) repeats and means of their attachment to different residues. While many thermoresponsive polypeptides have been described that possess LCSTs, there is limited understanding of how the molecular features of different side-chain structures affect solution properties. For most thermoresponsive polypeptides, LCST is mainly adjusted by variation of the number of side-chain EG repeats, with less attention given to the components of different linkages. Hence, it can be difficult to understand the differences in thermoresponsive properties of OEG-containing polypeptides prepared using different amino acids and side-chain linkages.

Thus, there is a need for new methods to convert natural amino acids into different functional residues, and a need for new thermoresponsive polypeptides.

SUMMARY OF THE INVENTION

The present invention provides a methodology for efficient, chemoselective transformation of methionines in peptides and polypeptides into stable, functional homocysteine derivatives. This process uses easily handled, readily available reagents, and allows facile incorporation of a wide range of functional modifications for different uses.

In one aspect, the present invention provides a polypeptide containing a functionalized homocysteine residue, R—$C^H$, as defined herein. In some embodiments, the R—$C^H$ residue has the structure:

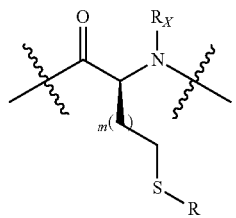

Where $R_X$, m, and R are as defined herein.

In a second aspect, the present invention provides methods of making polypeptides containing R—$C^H$ residues. In a third aspect, the present invention provides methods of reversibly switching the solubility characteristics of polypeptides containing R—$C^H$ residues.

DETAILED DESCRIPTION OF THE DRAWINGS

FIG. 1 shows conversion vs. time for demethylation of 31a using APDC. Conditions: 31a and 5 eq APDC in 75% EtOH for 0-22 h at 22° C., quenched with HCl$_{(aq)}$, followed by dialysis. Conversion=percent of methionine sulfonium groups converted.

Figure 2:
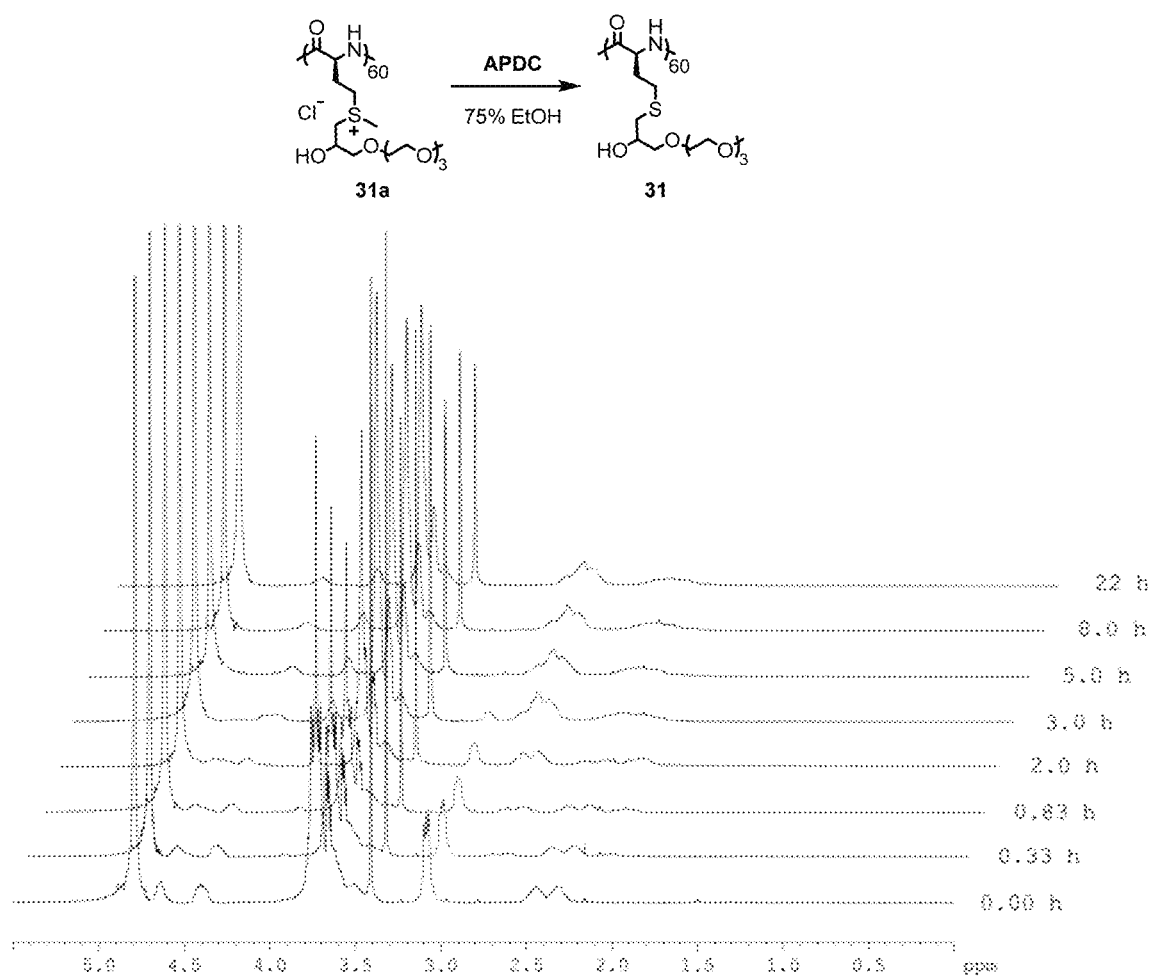

FIG. 2 shows $^1$H NMR spectra at indicated time points for the reaction of 31a with APDC. Resonances at approximately 3.1 ppm correspond to the methyl protons from 31a residues; resonances at approximately 2.8 ppm correspond to the two sets of methylene protons from 31 residues (at approximately 2.8 ppm).

Figure 3:
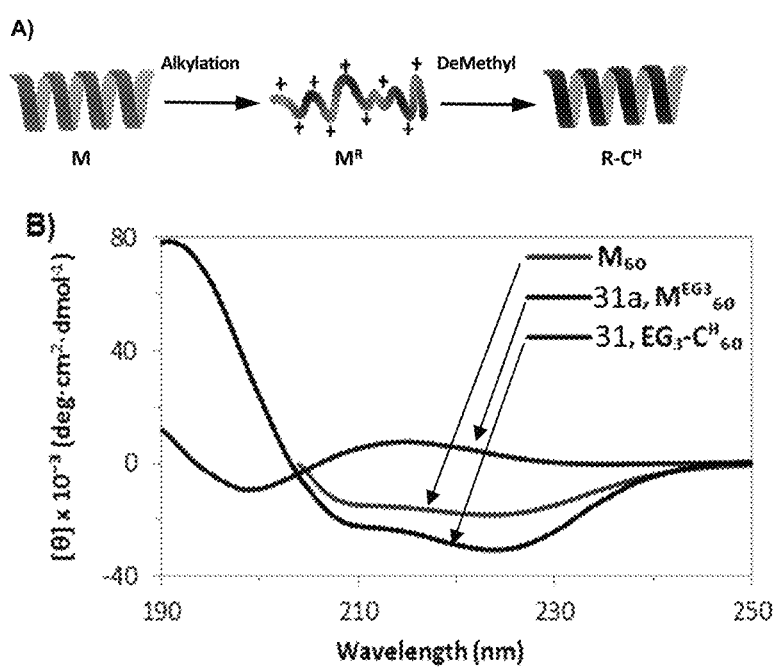

FIG. 3 shows the effect of chemical transformations on polypeptide properties. A) Scheme for complete conversion of helical, water-insoluble $M_{60}$ (SEQ ID NO: 1) to disordered, water soluble 31a ($M^{EG3}_{60}$ (SEQ ID NO: 1)), then to helical, water soluble 31 ($EG_3$-$C^H_{60}$ (SEQ ID NO: 2)) via M alkylation followed by demethylation. B) CD spectra of $M_{60}$ (SEQ ID NO: 1), 31a and 31 in either THF ($M_{60}$ (SEQ ID NO: 1)) or DI water (31a & 31). For $M_{60}$ (SEQ ID NO: 1), no data are presented below 204 nm due to solvent absorption that prohibits data collection. 31 found to be 85% α-helical. All CD spectra recorded at 0.5 mg/ml, 20° C. Figure discloses "$C^H_{60}$" as SEQ ID NO: 2.

Figure 4:
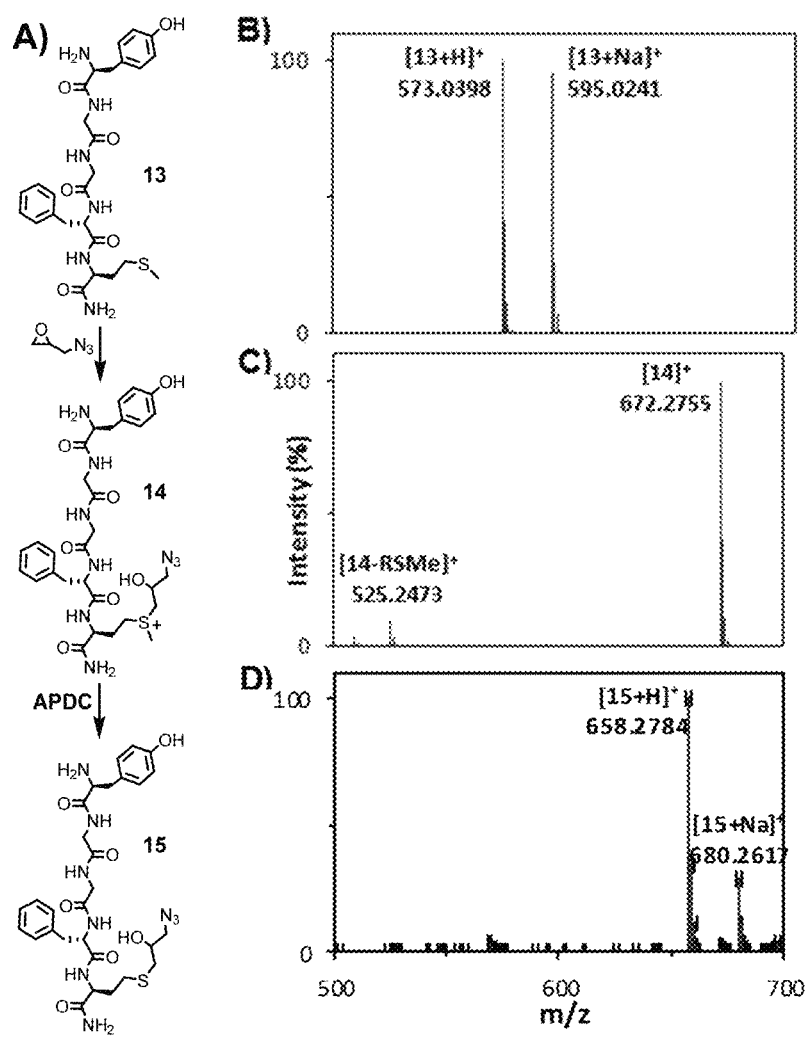

FIG. 4 shows chemoselective modification of met-enkephalin amide (13). (A) Reaction scheme for modification of M residues in 13 to yield azido functionalized R—$C^H$ residues. ESI-MS spectra of (B) starting peptide 13, with the proton [13+H]$^+$ and sodium [13+Na]$^+$ adducts labeled; (C) Product after alkylation, with molecular ion [14]$^+$ and characteristic fragment [14-RSMe]$^+$ labeled; and (D) Product after demethylation, with proton [15+H]$^+$ and sodium [15+Na]$^+$ adducts labeled. R=3-azido-2-hydroxypropyl.

Figure 5C:
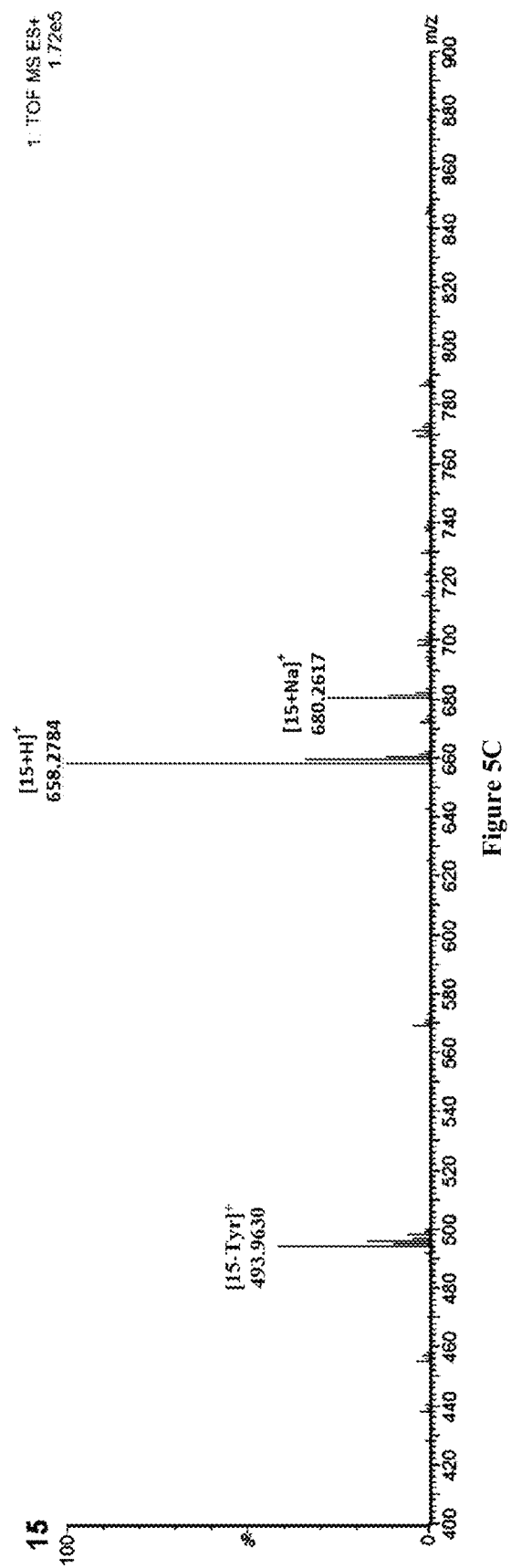

FIG. 5A: Expanded range ESI-MS data for 13 with [13+H]$^+$ (573.0398 m/z) and [13+Na]$^+$ (595.0241 m/z) ions labeled. FIG. 5B: Expanded range ESI-MS data for 14 with [14]$^+$ (672.2755 m/z) and fragment [14-RSMe]$^+$ (525.2473 m/z) ions labeled. FIG. 5C: Expanded range ESI-MS data for 15 with [15+H]$^+$ (658.2784 m/z), [15+Na]$^+$ (680.2617 m/z) and fragment [15-Tyr]$^+$ (493.9630 m/z) ions labeled.

Figure 6A:
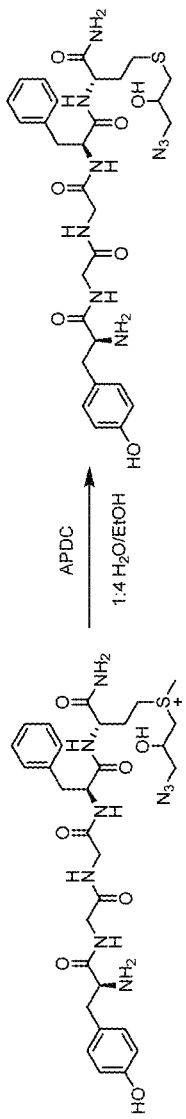
Figure 6B:
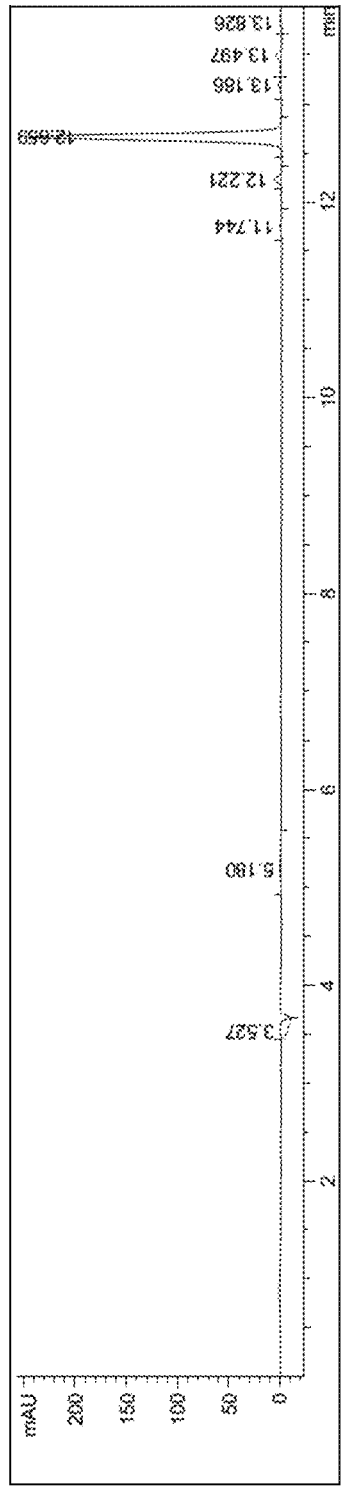
Figure 6C:
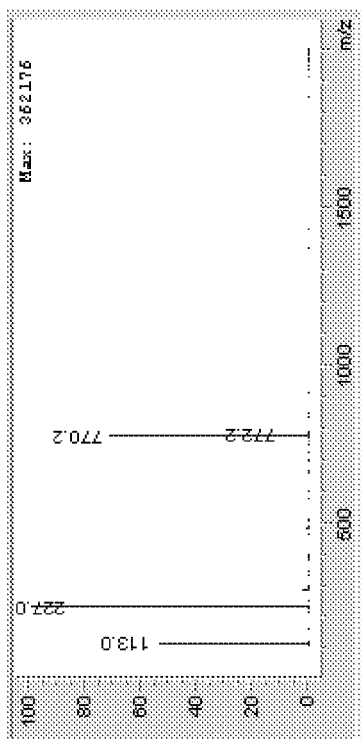

FIG. 6. shows LC-MS data for 15. Conditions: 14 (8.2 mM) and APDC (82 mM) in 75% EtOH at 22° C. for 26 h. Crude reaction mixture directly injected for LC-MS analysis. A) Scheme for synthesis of 15. B) UV trace (λ=280.4 nm) for LC of 15. C) MS of LC peak at 12.659 min confirming identity of [15+TFA]$^-$ (770.2 m/z).

Figure 7A:
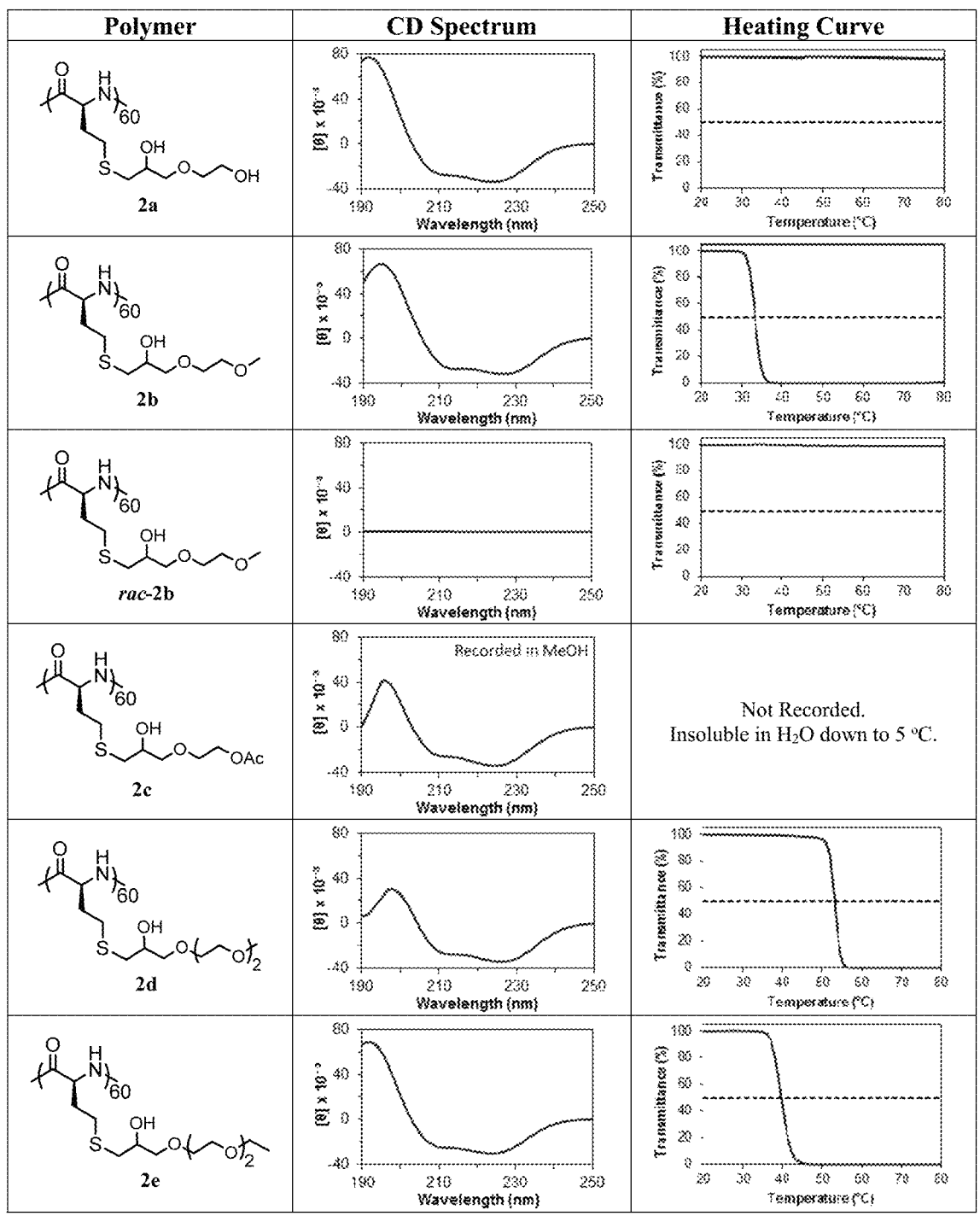
Figure 7B:
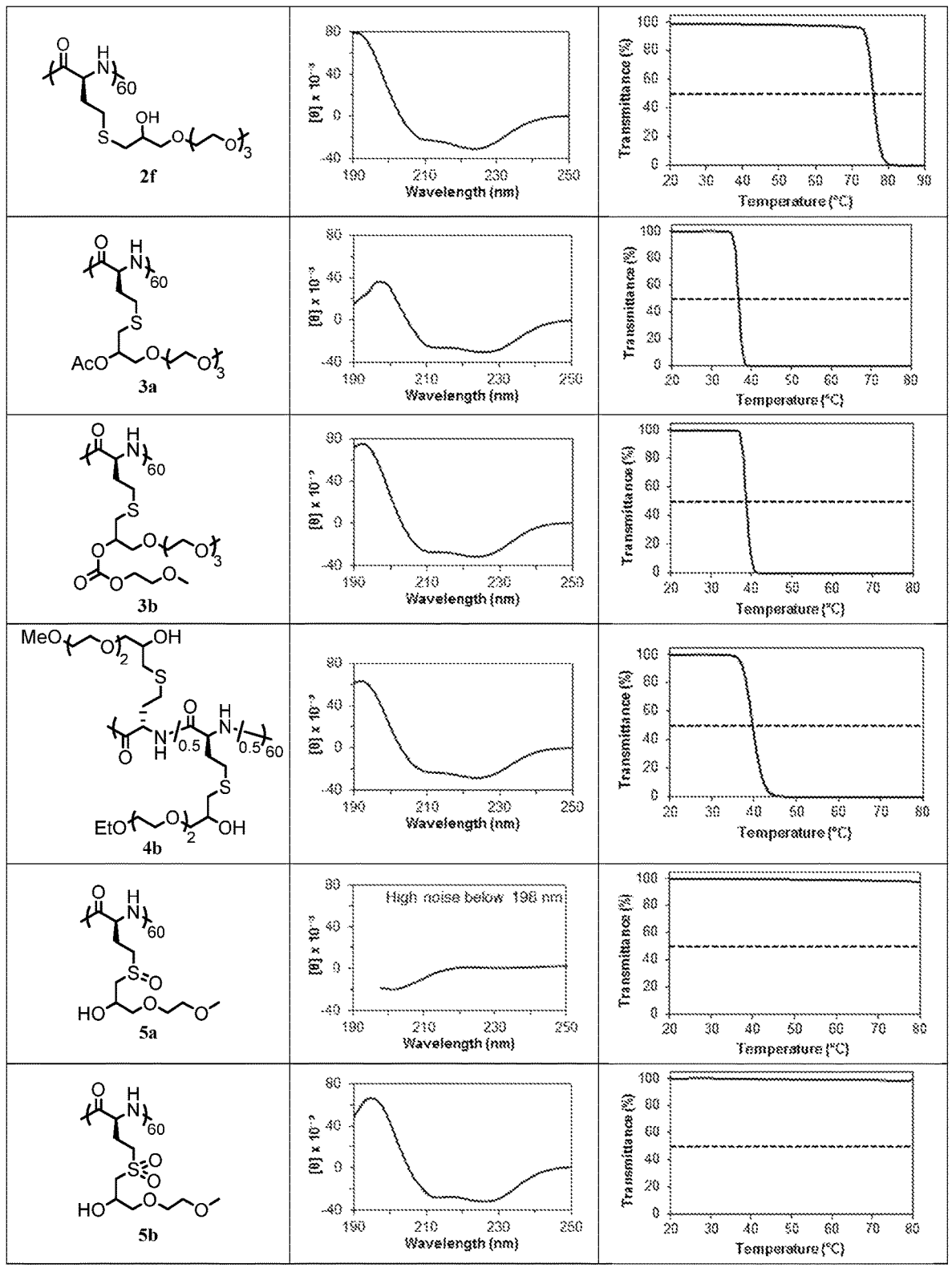

FIGS. 7A and 7B show CD Spectra and heating curves of exemplary OEG-Hcy derivatives. All CD spectra recorded in H$_2$O at 22° C. in H$_2$O except 2c which was recorded in MeOH due to low solubility (Concentration: 0.25 mg/mL (5a), 0.4 mg/mL (2e) 0.5 mg/mL (2a, 2b, 2f, 3b, 4b, 5b), 1.0 mg/mL (2c), 1.5 mg/mL (2d, 3a). Heating curves measured by heating polymer samples (3.0 mg/mL) at a rate of 1° C./min while recording transmittance (500 nm).

Figure 8:
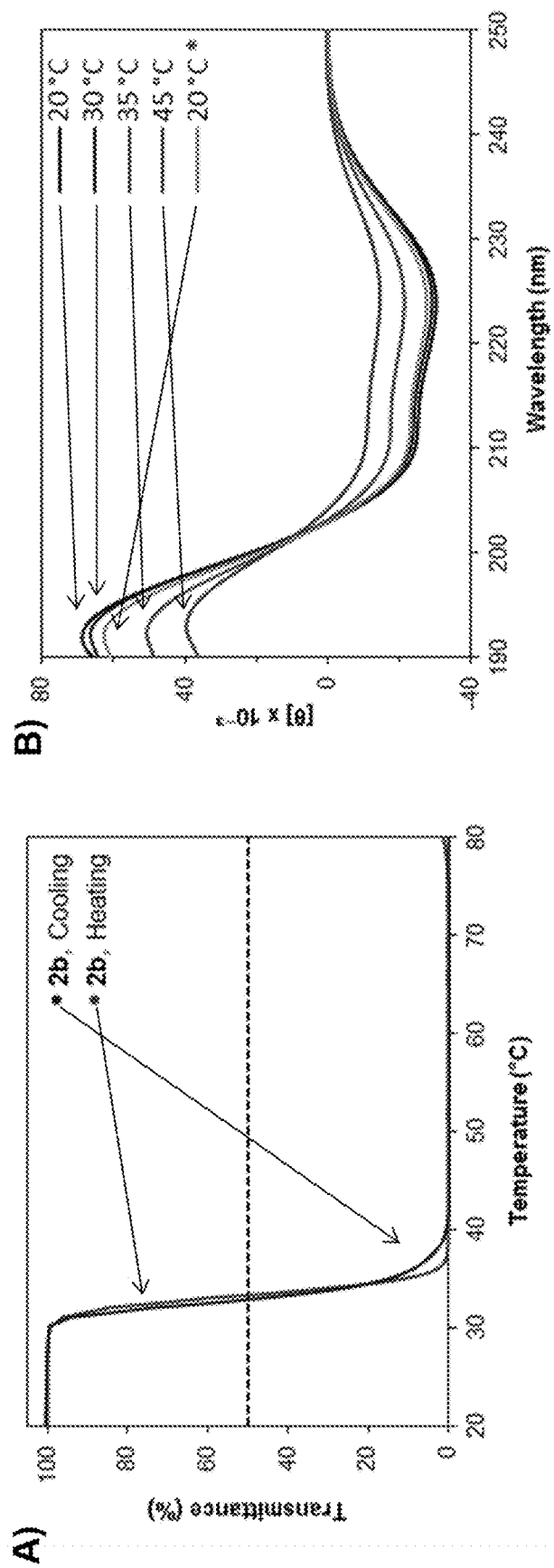

FIG. 8 shows A) heating and cooling curves for 2b (3.0 mg/mL) in H$_2$O. Heating or cooling rate: 1° C./min, transmittance recorded at 500 nm. B) CD spectra for 2e (0.5 mg/mL) in H$_2$O for a sample incrementally heated from 20° C. to 45° C. and returned back to 20° C. (label: 20° C.*). Aggregation at 35° C. and 45° C. decreased the magnitude of [θ], however the characteristic double minima indicate the polypeptide remained helical.

Figure 9:
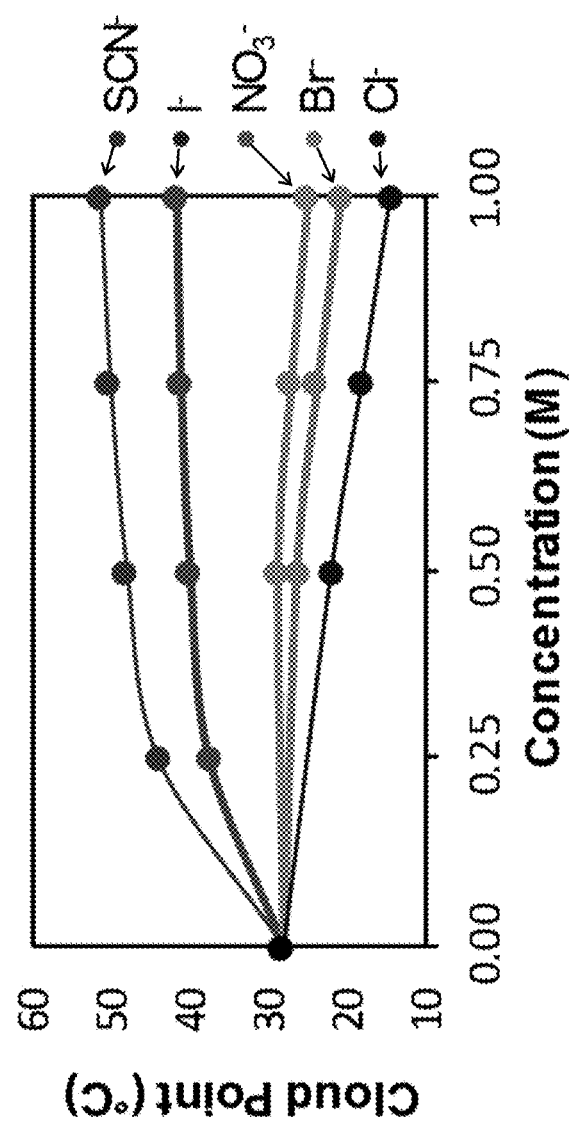

FIG. 9 shows Cloud point temperatures ($T_{cp}$) for 2e (3.0 mg/mL) in aqueous solutions containing different concentrations of Hofmeister salts (counterion=Na$^+$).

Figure 10:
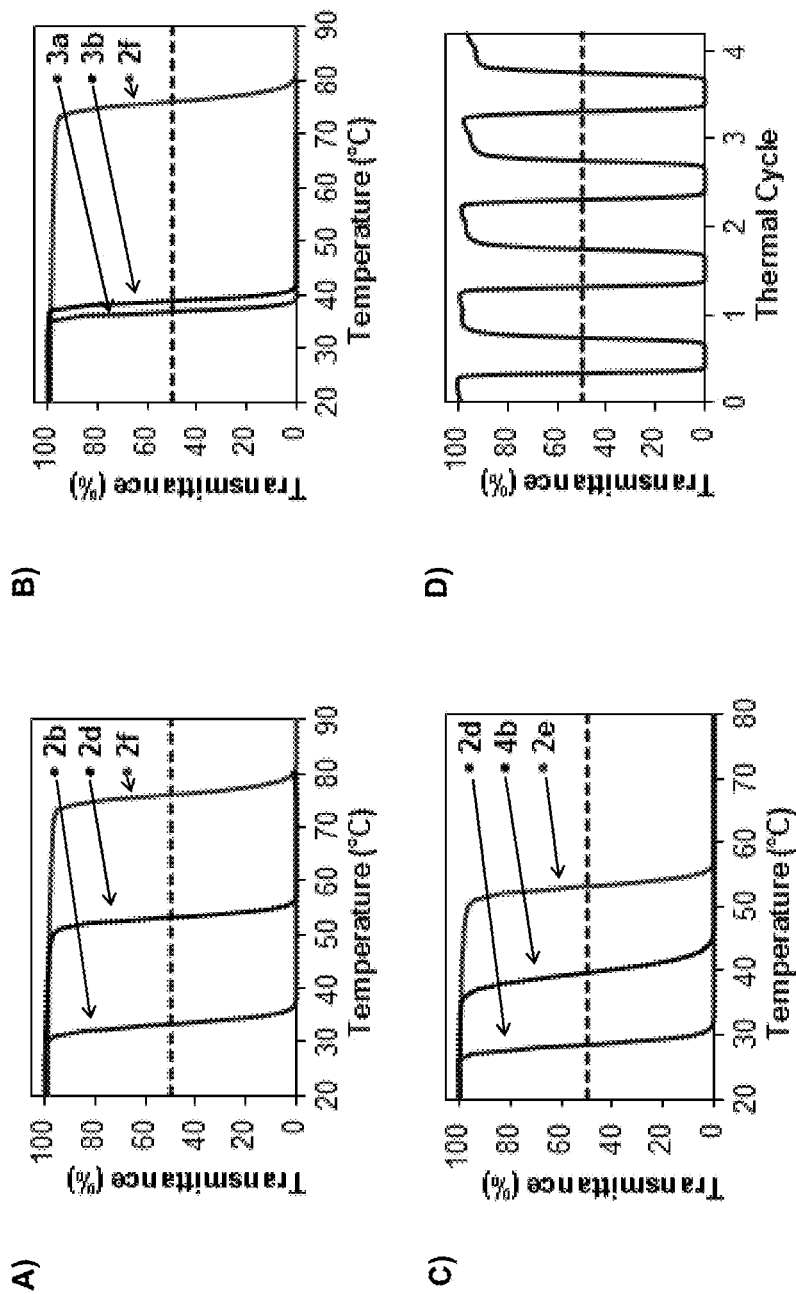

FIG. 10 shows (A) Heating curves for methyl terminated OEG-Hcy polymers as number of OEG repeats increased from 1 (2b) to 2 (2d) to 3 (2f). (B) Change in $T_{cp}$ upon conversion of the side-chain alcohol in 2f to the acetate ester (3a) or 2-methoxyethyl carbonate (3b). (C) Comparison of methyl (2d) and ethyl (2e) terminated OEG-Hcy polypeptides with the equimolar Me/Et terminated statistical copolymer (4b). (D) Reversibility of thermal transition of 2b with repeated cycling between 15 and 45° C. All measurements performed with polypeptide (3.0 mg/mL) in H$_2$O with heating or cooling rates of 1° C./min (2° C./min for panel D).

Figure 11:
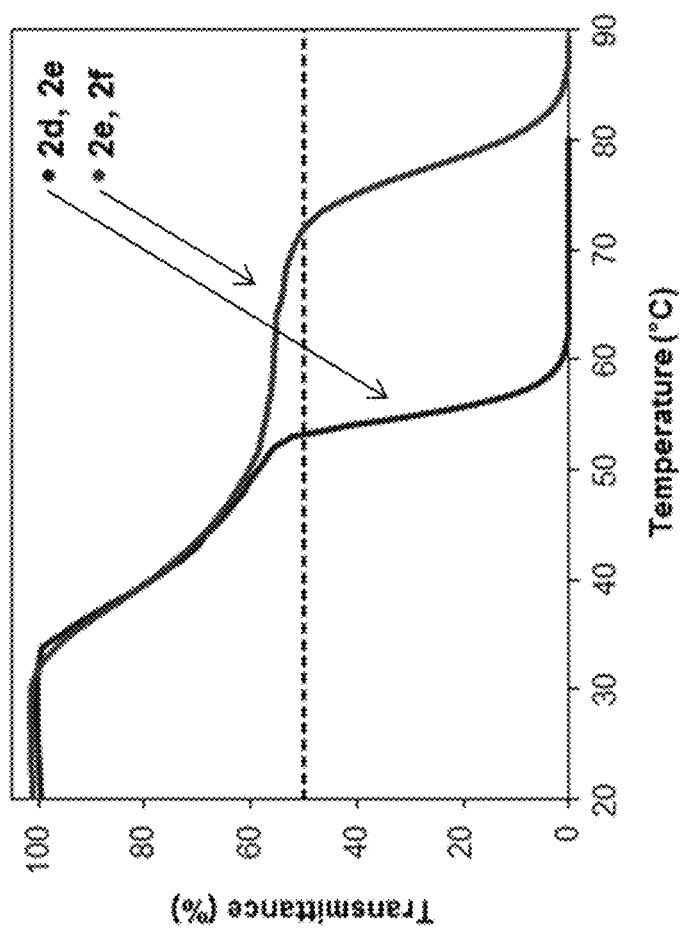

FIG. 11 shows heating curves for physical mixtures of 2e (0.5 mg/mL) with 2d or 2f (1.0 mg/mL) in H$_2$O. Two distinct cloud point temperatures were observed. The transition at lower temperature was attributed to the less hydrophilic polypeptide (2e) and the transition at higher temperature to the more hydrophilic polypeptide (2d or 2f). The low polypeptide concentrations needed to enable observation of both cloud points resulted in broader LCST transitions with higher cloud point temperatures than those reported at 3.0 mg/mL.

Figure 12:
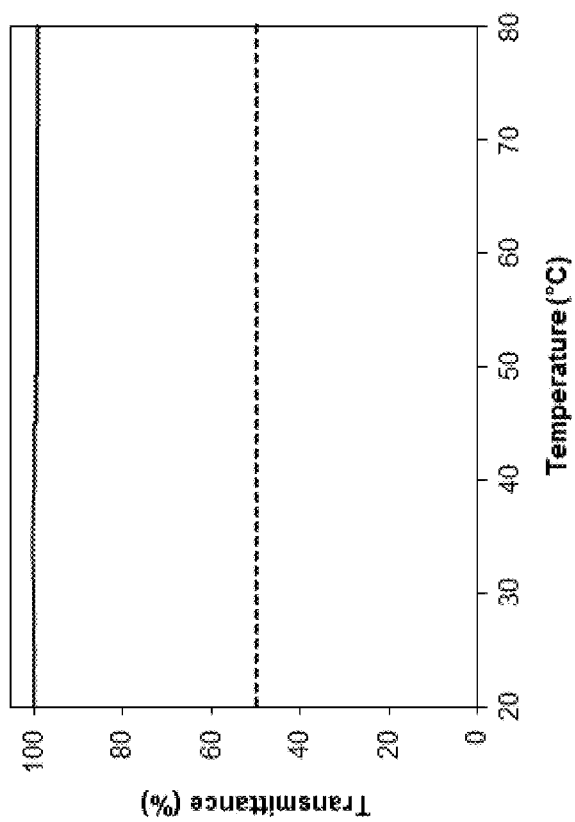

FIG. 12 shows heating curve for rac-2b (3.0 mg/mL) in H$_2$O. Heating or cooling rate: 1° C./min, transmittance recorded at 500 nm.

Figure 13:
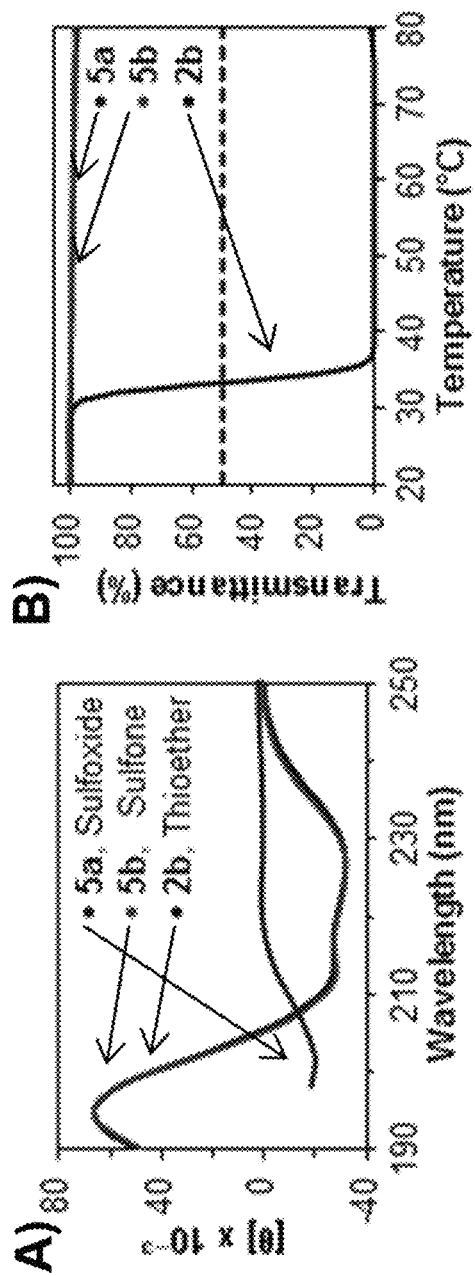

FIG. 13 shows effects of sulfur oxidation on chain conformation and thermoresponsive behavior of OEG-Hcy derivatives. (A) CD spectrum of thioether (2b) shows an α-helical conformation. Oxidation to the sulfoxide (5a) shows a disordered conformation, and further oxidation to the sulfone (5b) restores the α-helical conformation. All data were recorded in H$_2$O at 0.5 mg/mL, 20° C. For 5b no data were recorded below 198 nm due to sulfoxide absorption. 2b and 5b were found to be 84% and 86% α-helical, respectively. (B) 2b shows a $T_{cp}$ in water, but the more hydrophilic (5a, 5b) and disordered (5a) derivatives do not.

DETAILED DESCRIPTION OF THE INVENTION

The present invention provides a methodology for transforming methionines in peptides and polypeptides into homocysteine derivatives.

In one aspect, the present invention provides a polypeptide comprising an R—$C^H$ residue. The polypeptide may comprise 2 or more R—$C^H$ residues, 5 or more R—$C^H$ residues, 10 or more R—$C^H$ residues, 20 or more R—$C^H$ residues, or is entirely comprised of R—$C^H$ residues. A plurality of R—$C^H$ residues may be present in one or more contiguous sequences within the polypeptide, scattered throughout the polypeptide, or otherwise disposed throughout the length of a polypeptide. The polypeptide may have the sequence of a naturally occurring polypeptide, wherein some or all of the methionine residues in the naturally occurring polypeptide have been replaced by R—$C^H$ residues. The polypeptide may contain other residues that are incompatible with known techniques of producing R—$C^H$ residues by post-polymerization modification, such as residues containing thiol groups, such as cysteine. The polypeptide may be free of disulfide bridges.

In some embodiments, each R—$C^H$ residue in the polypeptide has a structure of Formula (I):

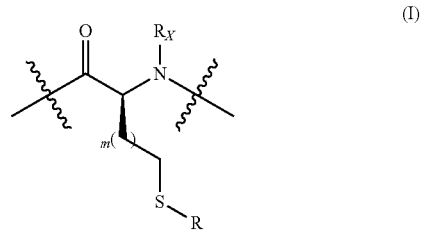

wherein:
m, independently for each R—$C^H$ residue, is 0, 1, 2, 3, or 4, preferably 1;
$R_X$, independently for each R—$C^H$ residue, is H or alkyl, preferably H; and
R, independently for each R—$C^H$ residue, is alkyl, provided that R is not unsubstituted methyl.

In some embodiments, R is not allyl or benzyl.

In some embodiments, the carbon atom of R that is directly bonded to the S atom is not activated, i.e., it is not adjacent to an atom that is sp$^2$ or sp hybridized. In some embodiments, the carbon atom of R that is directly bonded to the S atom is not allylic or benzylic. In certain preferred embodiments, the carbon atom of R that is directly bonded to the S atom is not adjacent to an sp$^2$- or sp-hybridized carbon atom. In some embodiments, R is not unsubstituted oligoethylene glycol, or glycosylated alkyl. In some embodiments, R does not contain sulfoxide, phosphate, phosphonate, a saccharide, or an ester.

In some embodiments, R is not more electrophilic than a methyl group.

In one aspect, the present invention provides a polypeptide comprising a C-terminal portion, an R—$C^H$ residue, and an N-terminal portion. In certain such embodiments, the polypeptide has the structure of Formula (II):

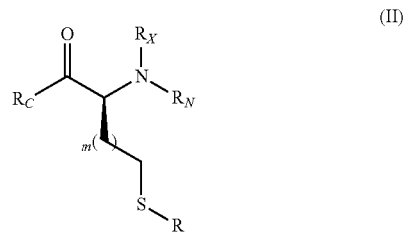

(II)

wherein m, R, and $R_X$ are as defined herein, and:
$R_C$ is the C-terminal portion, and is selected from hydroxyl, —O-(carboxylate protecting group), a natural or unnatural amino acid, or a C-terminal polypeptide fragment; $R_N$ is H, an amine protecting group, a natural or unnatural amino acid, or an N-terminal polypeptide fragment; or $R_C$ and $R_N$, taken together with the R—$C^H$ residue between them, form a cyclic polypeptide;
m is 0, 1, 2, 3, or 4, preferably 1;
$R_X$ is H or alkyl, preferably H; and
R is alkyl.

In some embodiments, each R—$C^H$ residue in a polypeptide is identical to the others; in other embodiments, a polypeptide may comprise two or more distinct R—$C^H$ residues, each distinct R—$C^H$ residue having a different alkyl group for R.

In some embodiments, the polypeptide of the present invention is a homopolymer. In other embodiments, it is a heteropolymer (e.g., a block, random, alternating, or other sequence of two or more amino acid units). In some embodiments, the polypeptide does not include any residue that is not an R—$C^H$ residue.

In some embodiments, the polypeptide of the present invention is N-terminally modified, C-terminally modified, or both.

In some embodiments, the polypeptide of the present invention has 2 or more residues, 4 or more residues, 10 or more residues, 20 or more residues, 40 or more residues, or 60 or more residues. In some embodiments, at least 1%, 5%, 10%, 20%, 25%, 40%, 50%, 60%, 75%, 80%, 90%, 95%, or 99% of the amino acids in a polypeptide sequence are R—$C^H$ residues.

In some embodiments, the polypeptide comprises at least one R—$C^H$ residue selected from S-3-amino-2-hydroxypropyl)-L-homocysteine, S-(3-(2-aminoethoxy)-2-hydroxypropyl)-L-homocysteine, S-(3-(2-aminoethoxy)-propyl)-L-homocysteine, S-(3-(2-(isopropylamino)ethoxy)-2-hydroxypropyl)-L-homocysteine, S-(3-(2-amino-3-isopropylamino-3-oxopropoxy)-2-hydroxypropyl)-L-homocysteine, S-(3-(2,3-diamino-3-oxopropoxy)-2-hydroxypropyl)-L-homocysteine, S-(3-(carboxymethoxy)-2-hydroxypropyl)-L-homocysteine, S-(3-(2-carboxy-1-aminoethoxy)-2-hydroxypropyl)-L-homocysteine, S-(3-(2-(2-aminoethoxy)-ethoxy)-2-hydroxypropyl)-L-homocysteine, or S-(3-(5-aminopentoxy)-2-hydroxypropyl)-L-homocysteine.

In some embodiments, the polypeptide comprises at least one R—$C^H$ residue selected from S-ethyl-L-homocysteine, S-propyl-L-homocysteine, S-butyl-L-homocysteine, S-(3-azido-2-hydroxypropyl)-L-homocysteine, S-(3-ammonio-2-hydroxypropyl)-L-homocysteine, S-(3-(carboxylatomethoxy)-2-hydroxypropyl)-L-homocysteine, S—((S)-3-2-ammonio-2-carboxylatoethoxy)-2-hydroxypropyl)-L-homocysteine, S-(2-hydroxy-4,7,10,13-tetraoxatetradecyl)-L-homocysteine, or S-((3-(2-(6-deoxy-D-galactopyranosid-6-yl)oxy)ethoxy)-2-hydroxypropyl)-L-homocysteine.

In some embodiments, the polypeptide of the present invention is poly(S-3-amino-2-hydroxypropyl)-L-homocysteine), poly(S-(3-(2-aminoethoxy)-2-hydroxypropyl)-L-homocysteine), poly(S-(3-(2-aminoethoxy)-propyl)-L-homocysteine), poly(S-(3-(2-(isopropylamino)ethoxy)-2-hydroxypropyl)-L-homocysteine), poly(S-(3-(2-amino-3-isopropylamino-3-oxopropoxy)-2-hydroxypropyl)-L-homocysteine), poly(S-(3-(2,3-diamino-3-oxopropoxy)-2-hydroxypropyl)-L-homocysteine), poly(S-(3-(carboxymethoxy)-2-hydroxypropyl)-L-homocysteine), poly(S-(3-(2-carboxy-1-aminoethoxy)-2-hydroxypropyl)-L-homocysteine), poly(S-(3-(2-(2-aminoethoxy)-ethoxy)-2-hydroxypropyl)-L-homocysteine), or poly(S-(3-(5-aminopentoxy)-2-hydroxypropyl)-L-homocysteine).

In some embodiments, the polypeptide of the present invention is poly(S-propyl-L-homocysteine), poly(S-butyl-L-homocysteine), poly(S-(3-azido-2-hydroxypropyl)-L-homocysteine), poly(S-(3-ammonio-2-hydroxypropyl)-L-homocysteine), poly(S-(3-(carboxylatomethoxy)-2-hydroxypropyl)-L-homocysteine), poly(S—((S)-3-2-ammonio-2-carboxylatoethoxy)-2-hydroxypropyl)-L-homocysteine), poly(S-(2-hydroxy-4,7,10,13-tetraoxatetradecyl)-L-homocysteine), or poly(S-((3-(2-(6-deoxy-D-galactopyranosid-6-yl)oxy)ethoxy)-2-hydroxypropyl)-L-homocysteine).

In some embodiments, the polypeptide of the present invention is

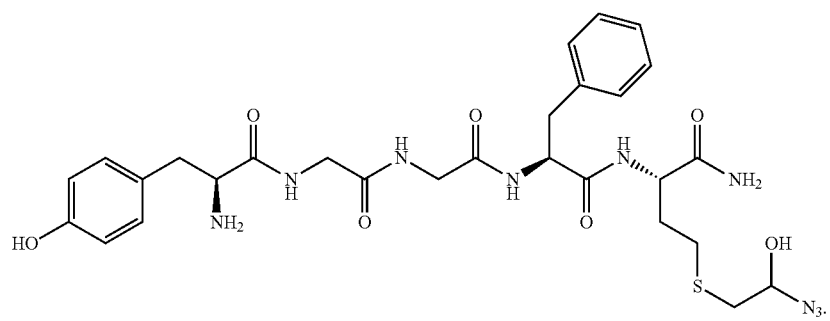 [SMILES: [N-]=[N+]=NC(O)CSCC[C@H](NC(=O)[C@H](Cc1ccccc1)NC(=O)CNC(=O)CNC(=O)[C@@H](N)Cc1ccc(O)cc1)C(N)=O]

In some embodiments, in the polypeptide of Formula (I) or (II), R is substituted or unsubstituted 2-hydroxypropyl.

In some embodiments, R is a moiety with the following structure:

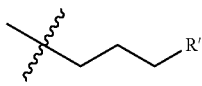

wherein R' is selected from H, alkyl, alkoxy, azido, aryl, heteroaryl, halo, allyloxy, alkylcarbonyl, phosphonate, carbamate, amido, $NH_3^+$,

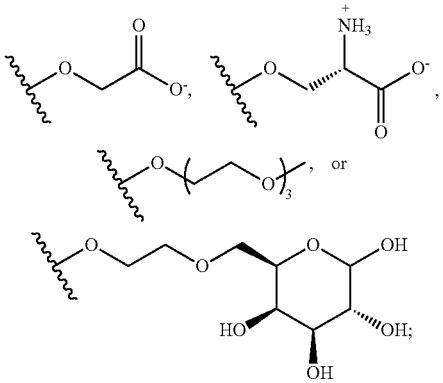

azido, aryl, heteroaryl, halo, allyloxy, alkylcarbonyl, phosphonate, carbamate, amido, $NH_3^+$

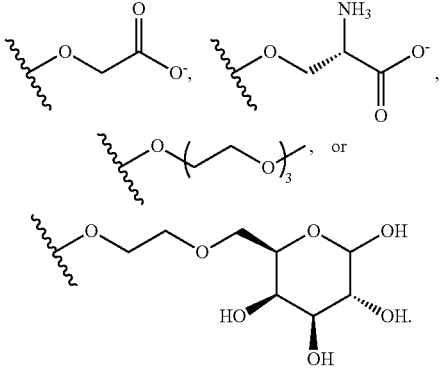

In some embodiments, R is a moiety with the following structure:

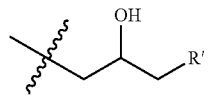

wherein R' is selected from H, alkyl, alkoxy, azido, aryl, heteroaryl, halo, allyloxy, alkylcarbonyl, phosphonate, carbamate, amido, $NH_3^+$,

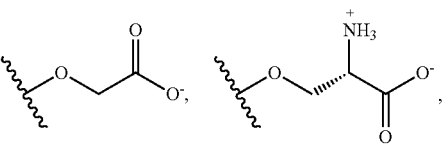

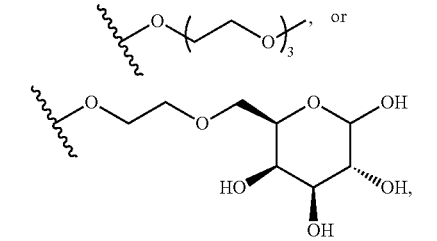

In some embodiments, R is a moiety with the following structure:

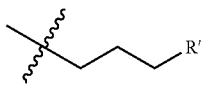

wherein R' is selected from H, alkyl, alkoxy, azido, aryl, heteroaryl, halo, allyloxy, alkylcarbonyl, phosphonate, carbamate, amido, $NH_3^+$, -continued

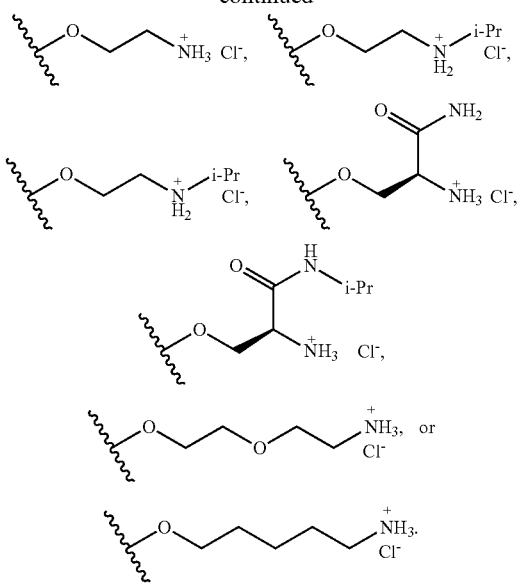

In some embodiments, R is a moiety with the following structure:

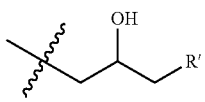

wherein R' is selected from H, alkyl, alkoxy, azido, aryl, heteroaryl, halo, allyloxy, alkylcarbonyl, phosphonate, carbamate, amido, NH$_3^+$,

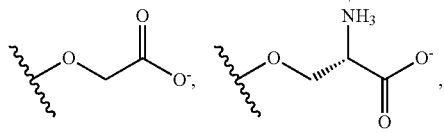

preferably R' is alkoxy, azido, aryl, heteroaryl, halo, allyloxy, alkylcarbonyl, phosphonate, carbamate, amido, NH$_3^+$,

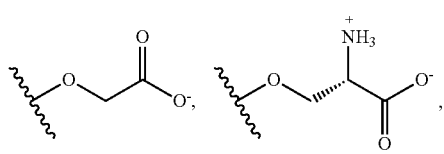

-continued

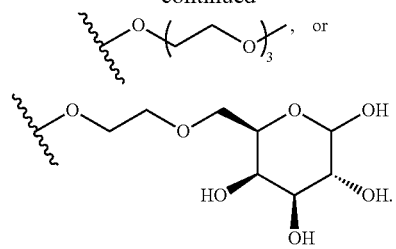

In certain embodiments, the invention relates to any of the compounds described herein, wherein R' is -L-halo, -L-azide, -L-NHR$^a$, -L-NR$^a$-TFA, -L-NR$^a$—C(O)—O-alkyl, -L-NR$^a$—C(O)—CH$_2$—NR$^a$-TFA, -L-O—CH$_2$—CH=CH$_2$, -L-O—CH$_2$CCH, -L-O-alkyl, -L-O—C(O)—alkyl, -L-P(O)(O-alkyl)$_2$, -L-P(O)(OH)$_2$, -L-O—C(O)—C(halo)(alkyl)$_2$, -L-CH$_2$—P(O)(O-alkyl)$_2$, -L-CH$_2$—P(O)(OH)$_2$, -LO—CH$_2$CH—(C(O)NR$^1$-alkyl)(NR$^1$-TFA), -L-O—CH$_2$CH—(C(O)OR$^1$)(NR$^1$-TFA), -L-OCH$_2$—C(O)—OR$^a$, -L-CH—(CO$_2$-alkyl)$_2$, -L-CH—(CO$_2$H)$_2$, -L-SO$_2$(O-alkyl), -L-SO$_2$(O-aryl), -L-SO$_3$H,

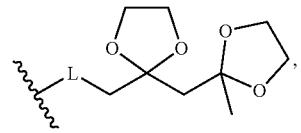

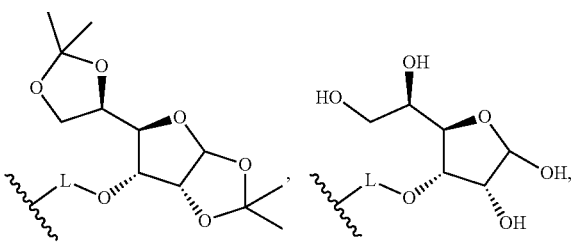

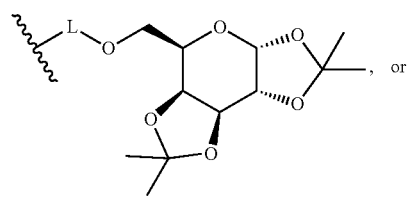

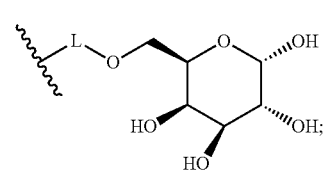

R$^a$ is H or alkyl; L is a bond or —(OCH$_2$CH$_2$)$_x$—, and x is 1-10.

In some embodiments, the polypeptide contains at least one R—C$^H$ residue with the following structure:

(II)

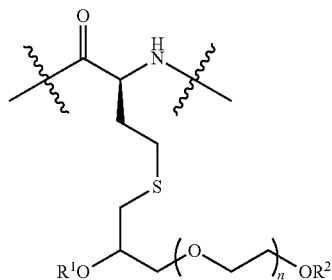

wherein:
R$^1$ is selected from H, alkyl, acyl, or alkoxy-C(O)—;
R$^2$ is selected from H, alkyl, acyl, or alkoxy-C(O)—; and
n is an integer from 0-10, preferably 1-3, more preferably 3.

In some embodiments, R$^1$ is H; R$^2$ is H, C$_{1-3}$ alkyl, or Ac; and n is 1, 2, or 3.

In some embodiments, the polypeptide contains at least one R—C$^H$ residue with the following structure:

(II)

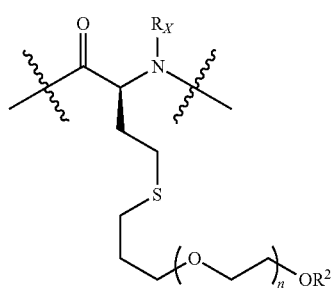

wherein:
R$^2$ is selected from H, alkyl, acyl, or alkoxy-C(O)—; and
n is an integer from 0-10, preferably 1-3, more preferably 3.

In some embodiments, R$^2$ is H, C$_{1-3}$ alkyl, or Ac; and n is 1, 2, or 3.

In some embodiments, at least one R—C$^H$ residue is S-(3-(2-hydroxyethoxy)-2-hydroxypropyl)-L-homocysteine, S-(3-(2-methoxyethoxy)-2-hydroxypropyl)-L-homocysteine, S-(3-(2-methoxyethoxy)-2-hydroxypropyl)-DL-homocysteine, S-(3-(2-acetoxyethoxy)-2-hydroxypropyl)-L-homocysteine, S-(2-hydroxy-4,7,10-trioxaundecyl)-L-homocysteine, S-(2-hydroxy-4,7,10-trioxadodecyl)-L-homocysteine, or S-(2-hydroxy-4,7,10,13-tetraoxatetradecyl)-L-homocysteine.

In some embodiments of the polypeptide containing an R—C$^H$ residue of Formula (II), the polypeptide is poly(S-(3-(2-hydroxyethoxy)-2-hydroxypropyl)-L-homocysteine), poly(S-(3-(2-methoxyethoxy)-2-hydroxypropyl)-L-homocysteine), poly(S-(3-(2-methoxyethoxy)-2-hydroxypropyl)-DL-homocysteine), poly(S-(3-(2-acetoxyethoxy)-2-hydroxypropyl)-L-homocysteine), poly(S-(2-hydroxy-4,7,10-trioxaundecyl)-L-homocysteine), poly(S-(2-hydroxy-4,7,10-trioxadodecyl)-L-homocysteine), or poly(S-(2-hydroxy-4,7,10,13-tetraoxatetradecyl)-L-homocysteine).

In some embodiments, M and M$^R$ residues comprise no more than 25%, 15%, 10%, 5%, 1%, or 0.5% of the M, M$^R$, and R—C$^H$ residues in the composition. In some embodiments, the composition is substantially free of M and M$^R$ residues.

In a second aspect, the present invention provides a method of preparing the polypeptides or compositions described above, comprising demethylating an M$^R$ sulfonium residue, wherein the demethylating step comprises contacting the M$^R$ sulfonium residue with a nucleophile, and further wherein R does not have enhanced electrophilicity relative to a methyl group.

In some embodiments, the method of preparing the polypeptides or compositions described above also comprises alkylating a methionine residue to produce an M$^R$ sulfonium residue. The methionine residue may be a component of a starting material polypeptide. The sequence of the starting material polypeptide may be found in nature. Alternatively, the sequence of the starting material polypeptide may be artificial. The starting material polypeptide may comprise cysteine.

In some embodiments, the nucleophile is APDC or thioacetate.

In some embodiments, the demethylating step takes place in the presence of ethanol.

In some embodiments, the demethylating step has a selectivity of at least 50%, 75%, 90%, 95%, 99%, or 99.5%.

In a third aspect, the present invention provides a method of reversibly switching solubility characteristics of the polypeptides described above, comprising oxidizing the —S— moieties in the polypeptide to —(S=O)— moieties to produce an oxidized polypeptide, wherein the oxidation converts a thermoresponsive polypeptide to a water soluble polypeptide. In some embodiments, the method further comprises reducing the —(S=O)— moieties in the oxidized polypeptide to —S— moieties.

Demethylation of Alkyl Methionine Sulfonium Residues

Methionine residues (M) are a good choice for site-specific peptide and protein modification, as well as for post-polymerization polypeptide functionalization, since they occur in low abundance in proteins, are easily introduced into peptides and polypeptides usually without protecting groups, and can undergo highly chemoselective alkylation reactions at pH<3 in high yield (eq 1).

(1)

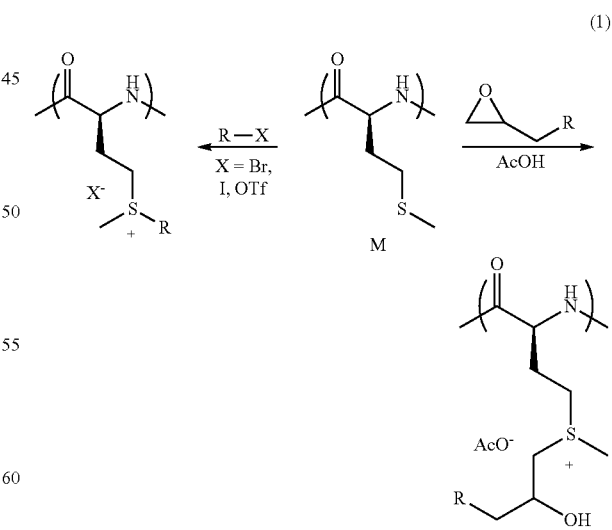

While alkyl methionium sulfonium (M$^R$) products themselves are potentially valuable as functional derivatives, they can be unstable toward nucleophiles, and their cationic nature may be undesirable for some uses. Reactions of M$^R$ salts with nucleophiles can yield up to three different products. The demethylation pathway is attractive as it leads to stable alkyl homocysteine residues (R—$C^H$), where the initial alkylating reagent reacted with M becomes the functional group in R—$C^H$ through a two-step transformation.

Scheme 1: Possible products for reaction of $M^R$ sulfonium residues with nucleophiles.

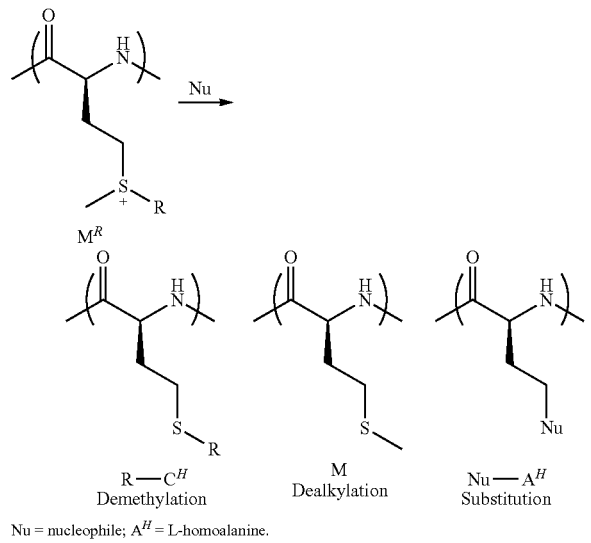

Nu = nucleophile; $A^H$ = L-homoalanine.

However, dealkylation, demethylation and substitution reactions all can occur. Substitution occurs primarily when the nucleophile is intramolecular. $M^R$ salts containing labile R groups, e.g., benzyl, can be readily and selectively dealkylated, but this only leads back to the starting material M. Selective demethylation to give an R—$C^H$ product was obtained for R=tBu, but required a complex procedure due to instability of the sulfonium intermediate, which dealkylates under most conditions. The present disclosure describes a versatile, selective process for conversion of M to R—$C^H$ in peptides and polypeptides.

Formation of $M^R$ salts from M residues in peptides, polypeptides and proteins can be accomplished chemoselectively and quantitatively using a variety of functional alkylating reagents, as is known in the art, e.g., U.S. Patent Application Publication Nos. 2015/0057433 and 2016/0002405; PCT Publication No. 2016/154120; J. R. Kramer and T. J. Deming, *Biomacromolecules* 2012, 13, 1719; E. G. Gharakhanian and Deming, T. J. *Biomacromolecules* 2015, 16, 1802; H. G. Gundlach, S. Moore and W. H. Stein, *J. Biol. Chem.* 1959, 234, 1761; F. Naider and Z. Bohak, *Biochemistry* 1972, 11, 3208; M. Taichi, T. Kimura and Y. Nishiuchi, *Int. J. Pept. Res. Ther.* 2009, 15, 247. J. R. Kramer and T. J. Deming, *Chem. Commun.* 2013, 49, 514; J. R. Kramer, R. Petitdemange, L. Bataille, K. Bathany, A.-L. Wirotius, B. Garbay, T. J. Deming, E. Garanger and S. Lecommandoux, ACS *Macro Lett.* 2015, 4, 1283; T. J. Deming et al., *Bioconjugate Chem.*, 2017, 28 (3), pp 691-700, DOI: 10.1021/acs.bioconjchem.6b00696. Each of these publications is incorporated by reference in its entirety.

To favor demethylation of these salts, as opposed to dealkylation or substitution (Scheme 1), the methyl substituent needs to be the most electrophilic site in the $M^R$ group. Labile R groups are readily removed from $M^R$ salts using thione and thiol nucleophiles, yet these are unable to demethylate $M^R$ salts when R=Me. However, as the present disclosure shows, more potent nucleophiles are able to demethylate $M^R$ salts, and use of more sterically demanding, non-labile R groups favors the demethylation pathway over dealkylation. $M^R$ salts prepared by reaction of M with functional epoxides are stable against dealkylation under a variety of conditions, so as an exemplary system, the reactions of a model poly(L-methionine sulfonium) system, poly(S-(2-hydroxy-4,7,10,13-tetraoxatetradecyl)-L-methionine sulfonium chloride)$_{60}$ (SEQ ID NO: 1), $M^{EG3}_{60}$ (SEQ ID NO: 1), with different nucleophiles were studied. The reactions were conducted in NaOAc buffered 95% EtOH ("$M^{EG3}_{60}$" disclosed as SEQ ID NO: 1):

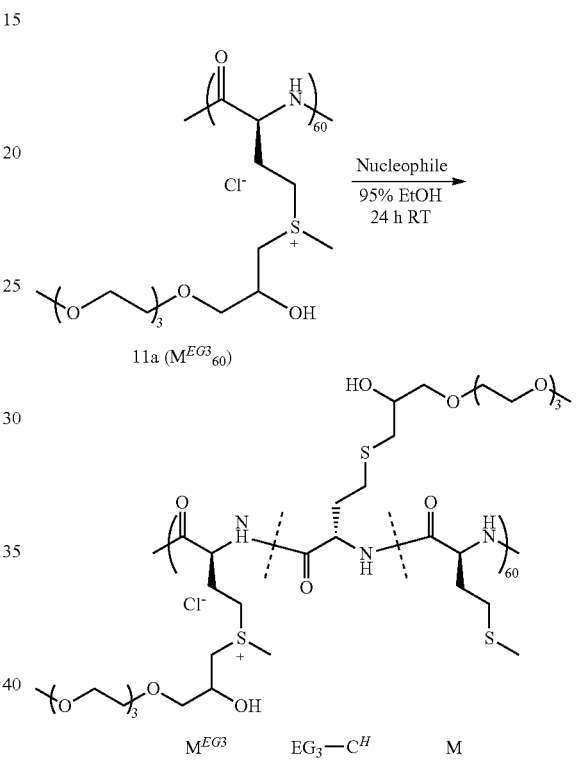

Using $M^{EG3}_{60}$ (SEQ ID NO: 1) allowed for facile purification and isolation of products via precipitation and dialysis, and the uniform sequence of $M^{EG3}_{60}$ (SEQ ID NO: 1) also allows for facile product characterization by NMR. While KI and 2-mercaptopyridine gave no reaction, and sodium thioglycolate gave 7% dealkylation, the more potent nucleophiles sodium thioacetate and ammonium pyrrolidinedithiocarbamate (APDC) were found to give selective and quantitative demethylation at 24 h to the corresponding fully functionalized poly(L-homocysteine) derivative, EG$_3$-$C^H_{60}$ (SEQ ID NO: 2), as shown in Table 1. In Table 1 and elsewhere, product selectivity indicates percent conversion to each type of product functional group.

TABLE 1

| | Product Selectivity (%) | | |
|---|---|---|---|
| Nucleophile | $M^{EG3}$ | EG$_3$—$C^H$ | M |
| None | 100 | 0 | 0 |
| KI | 100 | 0 | 0 |

TABLE 1-continued

| Nucleophile | Product Selectivity (%) | | |
|---|---|---|---|
| | $M^{EG3}$ | $EG_3$—$C^H$ | M |
| HS-CH2-COOH | 93 | 0 | 7 |
| pyridine-2-thione (NH) | 100 | 0 | 0 |
| K⁺ ⁻S-C(=O)-CH3 (potassium thioacetate) | 0 | 100 | 0 |
| NH4⁺ ⁻S-C(=S)-N-pyrrolidine (APDC) | 0 | 100 | 0 |

At a shorter reaction time of 3 h, APDC gave higher conversion to $EG_3$-$C^H$ groups compared to less nucleophilic thioacetate, and hence was used for all subsequent studies:

TABLE 2

11a → (Nucleophile, 75% EtOH, 3 h, RT) → 11

| Nucleophile | Conversion (%) |
|---|---|
| K⁺ ⁻S-C(=O)-CH3 | 20 |
| NH4⁺ ⁻S-C(=S)-N-pyrrolidine | 80 |

The successful selective demethylation of $M^{EG3}_{60}$ (SEQ ID NO: 1) to $EG_3$-$C^H_{60}$ (SEQ ID NO: 2) was found to be highly dependent on both the choice of nucleophile as well as the solvent used. The combination of resonance stabilized anionic nucleophiles (thioacetate or APDC) with less polar, EtOH rich solvent mixtures was found to be optimal for efficient demethylation. Use of EtOH/water mixtures with lower EtOH content led to much slower, albeit selective demethylation reactions:

TABLE 3

11a → (APDC, 0-75% EtOH) → 11

| Mass Fraction EtOH (%) | Conversion (%) | |
|---|---|---|
| | 3 h | 24 h |
| 0 | 10 | 58 |
| 50 | 33 | 99 |
| 75 | 80 | 100 |

These results agree with early studies on sulfonium hydrolysis that show ion-pairing occurs in low dielectric constant solvent mixtures, i.e. >75% EtOH, which accelerates the reaction of sulfonium ions paired with anionic nucleophiles. In addition, the electron delocalization in APDC may provide additional demethylation rate enhancement similar to that seen with sulfonium hydrolysis in the presence of acetate ions. Using APDC and 75% EtOH, it was found that complete conversion of $M^{EG3}_{60}$ (SEQ ID NO: 1) to $EG_3$-$C^H_{60}$ (SEQ ID NO: 2) occurred in ca. 8 h at 22° C., as depicted in the scheme below and in FIGS. 1 and 2.

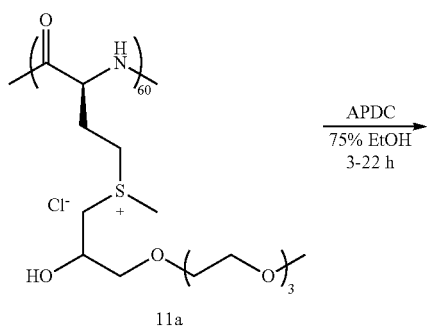

11a

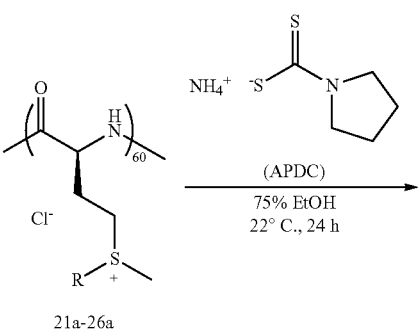

11

To further examine the selectivity of the demethylation reaction, a series of fully functionalized poly(L-methionine sulfonium)s was prepared, $M^R{}_{60}$ (SEQ ID NO: 1), where R were alkyl substituents of different size and electrophilicity (samples 21a-26a):

TABLE 4

Selectivity for demethylation versus dealkylation.
Conditions: 21a-26a and 5 eq. APDC in 75% EtOH
for 24 h at 22° C. 21, 25, 26 dialyzed. 22-24 washed
with MeOH. a = M is the only possible product. Yields
are of isolated, purified, fully converted polypeptides.

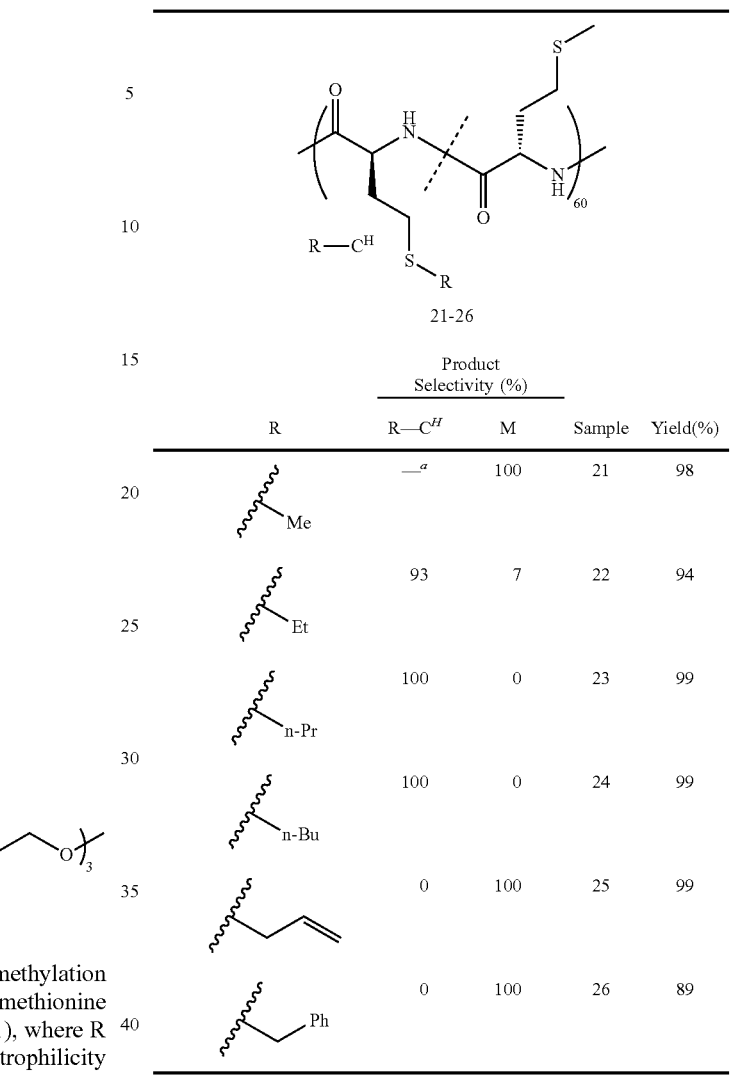

TABLE 4-continued 21-26

| R | Product Selectivity (%) | | Sample | Yield(%) |
|---|---|---|---|---|
| | R—$C^H$ | M | | |
| Me | —$^a$ | 100 | 21 | 98 |
| Et | 93 | 7 | 22 | 94 |
| n-Pr | 100 | 0 | 23 | 99 |
| n-Bu | 100 | 0 | 24 | 99 |
| (allyl) | 0 | 100 | 25 | 99 |
| Ph | 0 | 100 | 26 | 89 |

Under optimized reaction conditions from above, poly(S-methyl-L-methionine sulfonium), 21a, could be converted completely back to poly(L-methionine) in high yield. Notably, poly(S-ethyl-L-methionine sulfonium), 22a, gave the fully demethylated product with 93% selectivity in high yield, showing that the steric difference between ethyl and methyl is enough to strongly favor the demethylation pathway. Larger n-alkyls, 23a and 24a, gave exclusively the fully demethylated R—$C^H$ products. These reactions allow straightforward conversion of M residues to known analogs such as ethionine and buthionine. Sulfoniums with activated alkyls, such as allyl (25a) and benzyl (26a), were found to give exclusively the fully dealkylated product poly(L-methionine), confirming that demethylation does not occur if R has enhanced electrophilicity relative to methyl.

As seen above with $M^{EG3}{}_{60}$ (SEQ ID NO: 1), $M^R$ residues derived from epoxide alkylations of M strongly favor demethylation when treated with APDC, with possible enhanced selectivity due to the presence of the β-OH substituents on these R groups. To test the functional group tolerance of M to R—$C^H$ conversions, a variety of fully functionalized $M^R{}_{60}$ (SEQ ID NO: 1) derivatives were prepared in high yield using readily obtained, functional epoxides (samples 7a-12a).

TABLE 5

Complete conversion of $M^R_{60}$ to $R\text{—}C^H_{60}$ (SEQ ID NO: 1) to $R\text{-}C^H_{60}$ (SEQ ID NO: 2).
Conditions: 27a-32a and 5 eq. APDC in 75% EtOH for 24 h at 22° C., then dialyzed. a = Washed with MeOH in lieu of dialysis. b = Starting material protected, and product deprotected by treating with $K_2CO_3$ before dialysis (See SI). Yields are of isolated, deprotected, and purified polypeptides.

[Reaction scheme: 27a-32a (sulfonium chloride intermediate) → 27-32 (thioether product) via APDC, 75% EtOH, 22° C., 24 h]

| R | Sample | Yield(%) |
|---|---|---|
| —N$_3$ | 27 | 82$^a$ |
| —NH$_3^+$ Cl$^-$ | 28 | 98$^b$ |
| —O—CH$_2$—C(O)O$^-$ NH$_4^+$ | 29 | 92$^b$ |
| —O—CH(NH$_3^+$)—C(O)O$^-$ | 30 | 98$^b$ |
| —O—(CH$_2$CH$_2$O)$_3$— | 31 | 99 |
| —O—CH$_2$CH$_2$—O—(monosaccharide) | 32 | 91 |

All the examples shown gave exclusively the fully demethylated products in high yields after treatment with APDC. Reactive azido groups were readily incorporated (27), as well as charged (28,29) and zwitterionic (30) groups. Polar, non-ionic oligoethylene glycol (31) and monosaccharide (32) functionalized $R\text{—}C^H$ were also selectively prepared in high yield, providing an economical route to functional polypeptides with desirable properties. Samples 27-32 all possessed good solubility (>10 mg/mL) in water at 22° C., which was enhanced by the presence of the hydroxyl groups.

The characteristic solubility and conformational changes that occur in the complete transformation of an $M_{60}$ polymer (SEQ ID NO: 1) to an $M^R_{60}$ polymer (SEQ ID NO: 1) then to the $R\text{—}C^H_{60}$ (SEQ ID NO: 2) product are shown by the example in FIG. 3. Poly(L-methionine) is a hydrophobic polypeptide with poor water solubility that adopts a rigid α-helical conformation ($M_{60}$ (SEQ ID NO: 1), FIG. 3). After alkylation, resulting $M^R_{60}$ polymers (SEQ ID NO: 1) (31a ($M^{EG3}_{60}$ (SEQ ID NO: 1)), FIG. 3) are highly charged polyelectrolytes with good water solubility and disordered chain conformations. After demethylation, the $R\text{—}C^H_{60}$ polymers (SEQ ID NO: 2) contain non-ionic thioether linkages, and are hydrophilic, water soluble polymers that can adopt stable α-helical conformations if the R substituents are not charged (31 ($EG_3\text{-}C^H_{60}$ (SEQ ID NO: 2)), FIG. 3). The ability of $EG_3\text{-}C^H_{60}$ (SEQ ID NO: 2) to adopt a predominantly helical conformation also shows that ordered chain conformations can be obtained, which are beneficial for tuning polypeptide properties, and may allow for improved biomimicry in peptide derivatives.

To show the conversion of M to $R\text{—}C^H$ residues is not only applicable to polypeptides, this conversion was studied in a model bioactive peptide, met-enkephalin amide (13) (FIG. 4a,b). Enkephalins are natural, endogenous opioid peptides that are conformationally flexible and tolerate substantial chemical modification. Numerous structure-activity relationship studies have been conducted on enkephalins to improve and understand their selectivity for binding to different opioid receptors, and are aimed at developing better treatment of neuropathic pain. In addition to the use of conformational restraints, glycosylation and addition of lipophilic and aromatic groups have been used to modify enkephalins to improve their activity, receptor selectivity, and bioavailability. Hence, conversion of M residues to functional $R\text{—}C^H$ analogs in met-enkephalin amide may have potential value for such studies.

Treatment of 13 with glycidyl azide in glacial AcOH gave a dominant product (14), where the M residue was chemoselectively alkylated. The identity of 14 was determined using ESI-MS (FIG. 4a,c), where the parent ion [14]$^+$ showed addition of a single 100 Da 3-azido-2-hydroxypropyl group to each peptide. The presence of a fragment corresponding to the loss of a thioether group [14-RSMe]$^+$, which commonly occurs during MS analysis of $M^R$ ions, also confirmed that alkylation was exclusively occurring at the M residues. Subsequent demethylation of 14 using APDC gave the desired product 15, which was confirmed by observation of the [15+H]$^+$ and [15+Na]$^+$ adducts by ESI-MS (FIG. 4a,d). Expanded range ESI-MS data for all samples are shown in FIG. 5. High conversion in the demethylation reaction of 14 was seen by LC-MS analysis of the crude reaction mixture, which showed 15 as the predominant product (84% purity, see FIG. 6).

Synthesis of OEG Functionalized Polypeptides

A series of poly(OEG-alkylated-L-homocysteine)$_{60}$ (SEQ ID NO: 2) derivatives, OEG-Hey (2a-2f) were prepared using the process described above from poly(L-methionine)$_{60}$ (SEQ ID NO: 1), $M_{60}$ (SEQ ID NO: 1), via its alkylation using functionalized epoxides in acetic acid, followed by demethylation using APDC.

TABLE 6

Synthesis of OEG functionalized polypeptides. $M_{60}$ (SEQ ID NO: 1) alkylated with OEG epoxides to provide sulfoniums, 1a-f. Sulfoniums were demethylated to afford OEG—Hcy, 2a-f. Yields are of isolated, fully functionalized polypeptides.

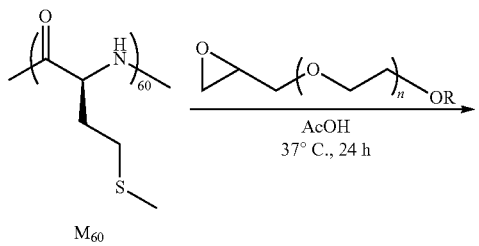

TABLE 6-continued

| Sample | n | R  | 1 (% yield) | 2 (% yield) |
|--------|---|----|-------------|-------------|
| c      | 1 | Ac | 94          | 97          |
| d      | 2 | Me | 95          | 81          |
| e      | 2 | Et | 92          | 99          |
| f      | 3 | Me | 90          | 99          |

This methodology allowed rapid and efficient synthesis of a systematic series of OEG functionalized polypeptides, which contained an unprecedented level of side-chain diversity (FIG. 1). In these samples, the number of EG repeats was varied from 1 to 3, and the EG terminal groups were also varied to include H, Ac, Me, and Et. To further increase diversity, samples of polypeptide 2f were modified at the hydroxyl groups in the linker between EG and amino acid into acetate (3a) and 2-methoxyethylcarbonate (3b) derivatives:

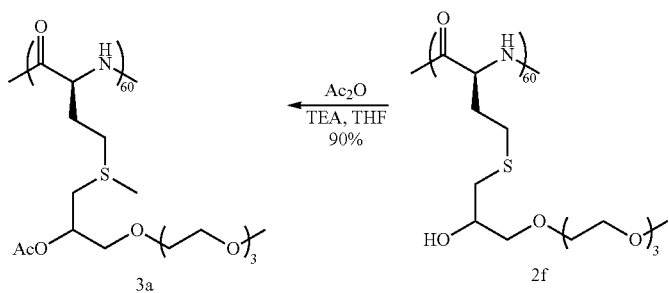

An equimolar statistical copolymer of 2d and 2e (4b) was also prepared for analysis.

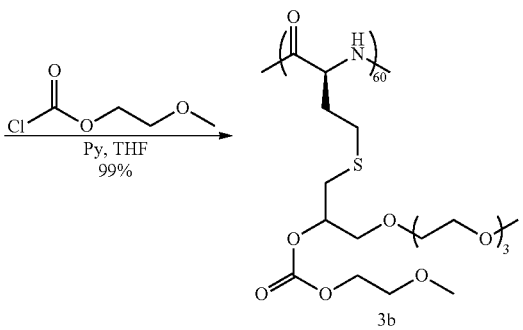

TABLE 6-continued

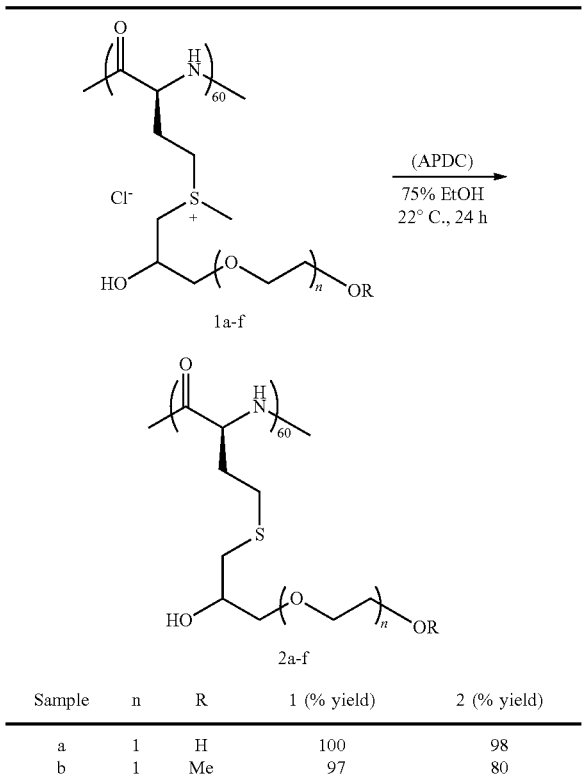

| Sample | n | R  | 1 (% yield) | 2 (% yield) |
|--------|---|----|-------------|-------------|
| a      | 1 | H  | 100         | 98          |
| b      | 1 | Me | 97          | 80          |

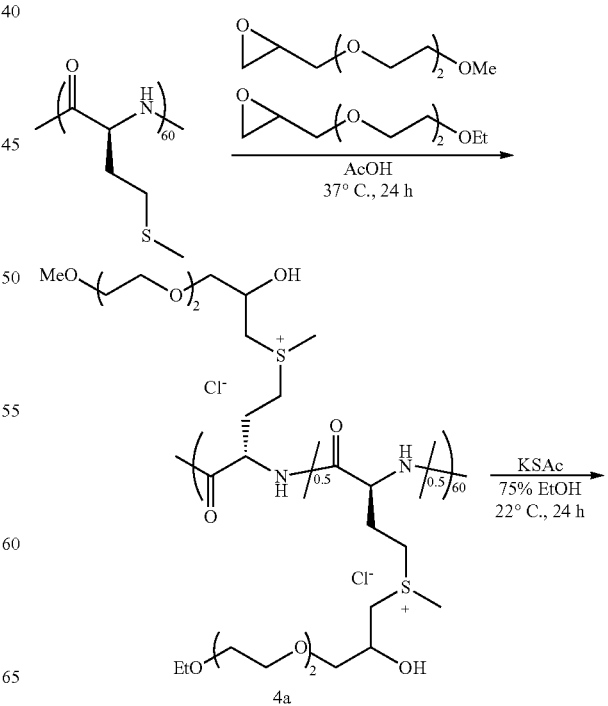

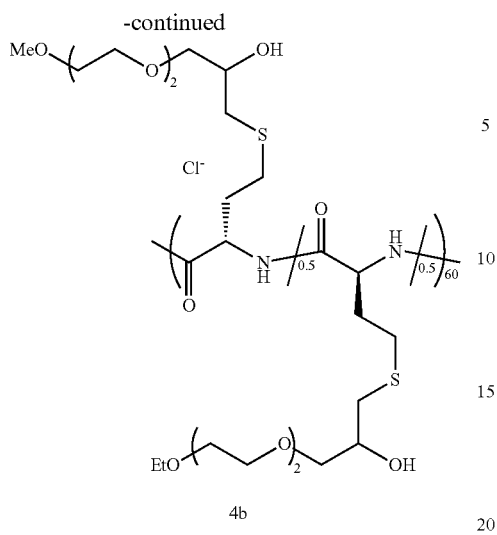

4b

All of the non-ionic OEG-Hcy samples described above were found to adopt predominantly α-helical conformations in deionized water at 22° C. (except for water insoluble 2c, which was measured in MeOH at 22° C.), as determined by circular dichroism (CD) spectroscopy (see FIG. 7)

The incorporation of precise side-chain structural modifications, enabled systematic study of the effects of different functionalities on the properties of the materials. Table 7 shows the results obtained from analysis of aqueous solutions of all the different OEG-Hcy homopolymers at concentrations of 3.0 mg/ml. Cloud point temperatures ($T_{cp}$) were determined at 50% transmittance by monitoring solution transmittance as a function of temperature, and were used to approximate the equilibrium LCST values. Since chain length variation and polymer concentration are well known to affect $T_{cp}$ values, all samples were identical in length, being prepared from the same stock of $M_{60}$ (SEQ ID NO: 1).

TABLE 7

Cloud point temperatures ($T_{cp}$) of OEG—Hcy polypeptides. $T_{cp}$ determined by heating polymer samples (3.0 mg/mL) at a rate of 1° C./min while recording transmittance (500 nm). $T_{cp}$ was the temperature where 50% transmittance was observed. a) No $T_{cp}$ detected, polymer fully soluble from 20 to 80° C. b) not applicable, polymer insoluble in H$_2$O down to 5° C. c) EC = (CH$_3$OCH$_2$CH$_2$OC(O)—). d) equimolar statistical copolymer.

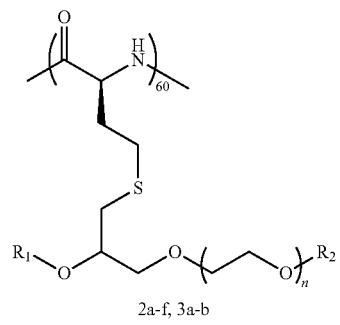

2a-f, 3a-b

| Polypeptide | n | R$_1$ | R$_2$ | $T_{cp}$ (° C.) |
|---|---|---|---|---|
| 2a | 1 | H | H | —a |
| 2b | 1 | H | Me | 33 |
| 2c | 1 | H | Ac | NA[b] |
| 2d | 2 | H | Me | 53 |
| 2e | 2 | H | Et | 28 |
| 2f | 3 | H | Me | 76 |
| 3a | 3 | Ac | Me | 39 |
| 3b | 3 | EC[c] | Me | 41 |
| 4b | 2 | H | Me/Et[d] | 40 |

As can be seen in Table 7, all samples, except fully water soluble 2a and water insoluble 2c, showed a $T_{cp}$ in water, which varied widely depending on number of EG repeats, as well as the nature of both the terminal and linker groups. These $T_{cp}$ were found to be reversible with minimal hysteresis, and polymers remained α-helical above $T_{cp}$ (see FIG. 8).

To study the effect of salts on $T_{cp}$, solutions of 2e were examined in the presence of different Hofmeister anions. Anions were varied since they are known to have more substantial effects on polymer thermoresponsive properties compared to cations (FIG. 9). The present results show that the effects of different salt concentrations and different anions affect cloud point temperatures of polymer 2e in various ways that are somewhat similar to the effects observed with other thermoresponsive polymer systems. These results allow $T_{cp}$ to be tuned by varying salt concentration, identity, and other parameters. None of the polycationic precursor polymers 1a-1f showed a $T_{cp}$ in water, and were fully water soluble due to their polyelectrolyte nature.

In order to better understand the origins of the differences in $T_{cp}$ values for the samples in Table 7, changes in $T_{cp}$ were measured as a function of individual molecular features. Samples 2b, 2d, and 2f, differ only in that the number of side-chain EG repeats increased from 1 to 3, which resulted in commensurate increases in $T_{cp}$ of ca. 20° C. per EG residue (FIG. 10a). This behavior is somewhat similar to the behavior of OEG containing polymethacrylates. Variation in number of EG repeats is the most common method used to adjust $T_{cp}$, since OEG units enhance water solubility at lower temperatures via H-bonding interactions with solvent that favor mixing, but these H-bonding interactions are disrupted at elevated temperatures, resulting in an LCST. Beyond variation of EG repeats, the nature of linker and EG terminal groups, R$_1$ and R$_2$ from Table 7, respectively, also had significant effects on $T_{cp}$.

Samples with different linker groups (R$_1$), which included hydroxyl (2f), acetate (3a) and 2-methoxyethylcarbonate (3b), were also found to possess a range of T$_{cp}$ values (FIG. 10b). Both carbonate and ester functionalities were found to greatly lower T$_{cp}$ compared to the parent hydroxyl group. This can be explained by the hydroxyl group's greater ability to H-bond, both as donor and acceptor, to water solvent. The similarity in T$_{cp}$ between 3a and 3b may be explained by the higher polarity of the ester group being counterbalanced by a less polar carbonate that also includes a solubilizing EG group. This series of samples shows that the hydroxyl group in the linker of 2f provides a substantial enhancement in water solubility as evidenced by the increase in T$_{cp}$ of ca. 36° C. over the other samples. Polar hydroxyl groups have been introduced previously in thermoresponsive statistical copolymers as a means to increase T$_{cp}$. However, no other homopolymers with hydroxyl groups in each side-chain are known to possess an LCST in water, as high hydroxyl group density typically results in chains being fully soluble in water regardless of temperature. The unique localization of hydroxyl groups within the linker region, as opposed to the side-chain terminus, may be the reason why hydroxyl containing OEG-Hcy polypeptides possess LCSTs. Supporting this hypothesis, sample 2a, which contains an additional hydroxyl group at the side-chain terminus, was found to be fully water soluble with no LCST (Table 7).

chain molecular features. Another important structural characteristic of OEG-Hcy polymers shown herein is their stable α-helical conformation, also found in other thermoresponsive polypeptides, which allows for sharp thermal transitions with excellent reversibility over many heating/cooling cycles (FIG. 10d). Thermoresponsive polypeptides with disordered or less stable α-helical conformations can adopt β-sheet conformations above T$_{cp}$, which leads to irreversible phase separation of the polymers. The α-helical conformations of OEG-Hcy are also an important reason why these polymers possess lower LCSTs with fewer EG repeats compared to disordered polypeptides. The lack of conformational freedom in the α-helical chains leads to small entropy of mixing with water, which facilitates their phase separation at lower temperatures. By comparison, analogs of α-helical thermoresponsive polypeptides that possess disordered conformations, which have much greater entropy of mixing with water, are fully water soluble and do not have LCSTs. Similar behavior was also observed here for a sample of 2b prepared from racemic poly(DL-methionine) (i.e. rac-2b, see FIGS. 7 and 12).

Since chain conformations of OEG-Hcy polymers affect whether or not they have LCSTs in water, oxidation of the thioether linkages was used in these polymers as a means to alter both chain conformation and side-chain polarity (eq 2).

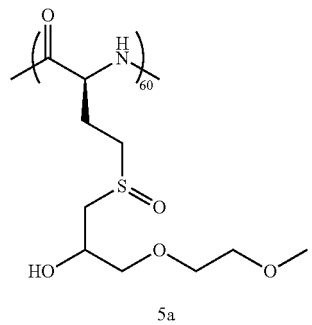
5a

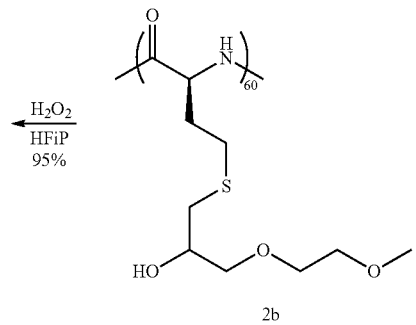
2b

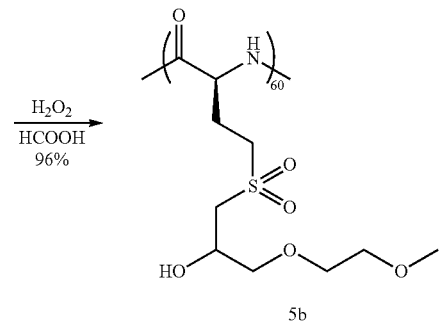
5b

The effect of the EG terminal groups (R$_2$) on T$_{cp}$ was also studied with samples 2d, 2e, and 4b, where R$_2$ was either Me, Et, or a 1:1 statistical mixture of Me and Et. As the groups became more hydrophobic, the polymers became less water soluble, and T$_{cp}$ values decreased (FIG. 10c). The statistically grafted copolymer 4b showed that terminal groups can be mixed to obtain a single, reversible transition at an intermediate T$_{cp}$ value. Slight broadening of the thermal transition for this statistical copolymer compared to the homopolymers may be due to small differences in comonomer distribution among individual copolymer chains. Physical blends were also prepared of sample 2e with 2d or 2f, which upon heating showed the presence of distinct T$_{cp}$ for each polymer component (see FIG. 11). These data suggest that statistical functionalization of individual chains is necessary to obtain a single, average T$_{cp}$, while physical blending retains the characteristics of the individual components. These principles are potentially useful for fine adjustment of T$_{cp}$ values, as well as preparation of sequentially thermoresponsive blends and block copolymers.

OEG-Hcy polymers are a robust platform whose thermoresponsive properties can be adjusted based on the data presented herein through variation of three distinct side- Oxidation of thioether groups in poly(alkyl-L-homocysteine)s to sulfoxides results in a transition from α-helical to disordered conformations, and further oxidation to sulfones results in reversion to stable α-helical conformations. As shown by example with 2b, these oxidation induced conformational changes, as measured using CD spectroscopy, also occur in the OEG-Hcy polypeptides (FIG. 13a). Examination of the water solubility for the sulfoxide (5a) and sulfone (5b) derivatives of 2b as a function of temperature showed that both have good solubility and neither polymer has a LCST (FIG. 13b). The disordered conformation of 5a likely improves solubility of this sample compared to 2b, however the increased polarity of both the sulfoxide and sulfone groups in 5a and 5b also significantly increases their water solubility, such that the helicity of 5b does not lead to recovery of an LCST. Overall, oxidation of thioether groups in OEG-Hcy polymers is an effective means to switch off their LCST properties. Since sulfoxides can also be reduced back to thioether groups under mild conditions, interconversion between these two states can be expected to reversibly switch OEG-Hcy polymers between thermoresponsive and fully water soluble states.

ABBREVIATIONS

Acetonitrile (MeCN), N-carboxyanhydride (NCA), degree of polymerization (DP), L-methionine (Met), L-methionine residue (M), L-Methionine sulfonium residue ($M^R$), alkyl homocysteine residue (R—$C^H$), glacial acetic acid (AcOH), electrospray ionization-mass spectrometry (ESI-MS), ethanol (EtOH), ethyl acetate (EtOAc), formic acid (HCOOH), diethyl ether ($Et_2O$), trifluoroacetic acid (TFA), trifluoroacetic anhydride (TFAA), meta-chloroperbenzoic acid (mCPBA), molecular weight cut-off (MWCO), room temperature (RT), equivalents (eq), methanol (MeOH), N,N-dimethylformamide (DMF), broad (br), doublet (d), doublet of doublets (dd), doublet of doublet of doublets (ddd), doublet of multiplets (dm), doublet of quartets (dq), doublet of triplets (dt), pentet (p), quartet (q), septet (sep), sextet (sext) singlet (s), triplet (t), triplet of doublets (td), thin layer chromatography (TLC), acetic anhydride ($Ac_2O$), Ammonium pyrrolidinedithiocarbamate (APDC), deuterated trifluoroacetic acid (d-TFA), hexafluoroisopropanol (HFiP), pyridine (py), tetrahydrofuran (THF) and triethylamine (TEA).

Definitions

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

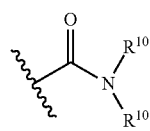

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

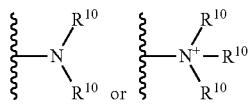

wherein each $R^{10}$ independently represents a hydrogen or a hydrocarbyl group, or two $R^{10}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

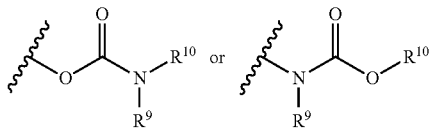

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring.

The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —$OCO_2$—$R^{10}$, wherein $R^{11}$ represents a hydrocarbyl group.

The term "carboxy", as used herein, refers to a group represented by the formula —$CO_2H$.

The term "ester", as used herein, refers to a group —C(O)$OR^{10}$ wherein $R^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "polypeptide" refers to a molecule comprising 2 or more amino acids linked by peptide bonds. A polypeptide may be linear or cyclic. A polypeptide may be functionalized or modified at its N-terminus, its C-terminus, or at any of the amino acids within it, including by protecting groups. A polypeptide may contain both natural and unnatural amino acids. "Post-polymerization modification" refers to the action of chemically modifying the amino acids in a polypeptide, the C-terminus, or the N-terminus. A polypeptide may comprise 2 or more amino acids, 5 or more amino acids, 10 or more amino acids, 25 or more amino acids, 50 or more amino acids, or 100 or more amino acids. A polypeptide may be a molecule that is commonly referred to in the art as a "peptide", an "oligopeptide", a "polypeptide", or a "protein", or any other art-recognized term that satisfies the definition herein. A polypeptide may be part of a larger structure, such as a protein.

The term "silyl" refers to a silicon moiety with three hydrocarbyl moieties attached thereto.

The term "silyloxy" refers to an oxygen moiety with a silyl attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds.

The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

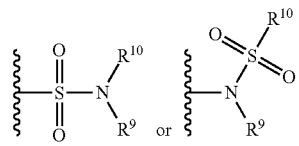

wherein R$^9$ and R$^{10}$ independently represents hydrogen or hydrocarbyl, such as alkyl, or R$^9$ and R$^{10}$ taken together with the intervening atom(s) complete a heterocycle having from 4 to 8 atoms in the ring structure.

The term "sulfoxide" is art-recognized and refers to the group —S(O)—R$^{10}$, wherein R$^{10}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—R$^{10}$, wherein R$^{10}$ represents a hydrocarbyl.

The term "thioalkyl", as used herein, refers to an alkyl group substituted with a thiol group.

The term "thioester", as used herein, refers to a group —C(O)SR$^{10}$ or —SC(O)R$^{10}$ wherein R$^{10}$ represents a hydrocarbyl.

The term "thioether", as used herein, is equivalent to an ether, wherein the oxygen is replaced with a sulfur.

The term "urea" is art-recognized and may be represented by the general formula

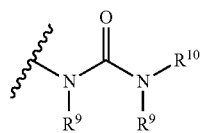

wherein R$^9$ and R$^{10}$ independently represent hydrogen or a hydrocarbyl, such as alkyl, or either occurrence of R$^9$ taken together with R$^{10}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxylprotecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

The invention now being generally described, it will be more readily understood by reference to the following examples which are included merely for purposes of illustration of certain aspects and embodiments of the present invention, and are not intended to limit the invention.

EXAMPLES

Example 1: Synthetic Procedures

Poly(L-methionine)$_{60}$ (SEQ ID NO: 1), M$_{60}$ (SEQ ID NO: 1)

Prepared by previously reported method. Kramer, J. R.; Deming, T. J. *Biomacromolecules* 2012, 13, 1719-1723. Met NCA was polymerized with Co(PMe$_3$)$_4$ in THF under N$_2$ using a 20:1 monomer to initiator ratio. The DP was determined by endcapping a small aliquot from the polymerization mixture with 2 kDa PEG-isocyanate (CH$_3$(OCH$_2$CH$_2$)$_{45}$N=C=O) followed by $^1$H NMR analysis. Found average DP=58.

M$_{60}$ (SEQ ID NO: 1) Alkylation Procedure a (Alkylation Procedure A)

M$_{60}$ (SEQ ID NO: 1) is alkylated with an alkyl halide in H$_2$O. If an activated alkyl halide is used, poly(Met) is suspended in either DMF, water, or 0.2 M aqueous formic acid (10 mg/mL). Alkyl halide (3 eq. per methionine residue) is added. 1.1 eq alkyl halide per methionine can also be used with an increased reaction time of 72 hours to give identical products. The reaction mixture is covered with foil and stirred at room temperature for 48 hours. The reaction is then diluted 2× with water, transferred to a 2000 MWCO dialysis bag, and dialyzed against 0.10 M NaCl for 24 hours, followed by DI water for 48 hours with water changes twice per day. Dialysis against NaCl serves to exchange counterions so that only chloride is present. The contents of the dialysis bag are then lyophilized to dryness to give the product as a white solid.

If an unactivated alkyl halide is used, poly(Met) is suspended in dry MeCN (10 mg/mL). Alkyl halide (1.1 eq per methionine residue) is added, followed by a solution of AgBF$_4$ in MeCN (50 mg/mL, 1 equiv). The reaction mixture is covered with foil and stirred at 50° C. for 24 hours under N$_2$. A yellow precipitate generally evolves. The reaction is centrifuged to remove the precipitate, and polymer is isolated by precipitation with ether and evaporation to dryness to give the product, generally as a white solid. The product can then be dispersed in water, transferred to a 2000 MWCO dialysis bag, and then dialyzed against 0.10 MNaCl for 24 hours, followed by DI water for 48 hours with water changes twice per day. Dialysis against NaCl serves to exchange counterions so that only chloride is present.

See U.S. Patent Application Publication No. 2015/0057433 and Kramer, J. R.; Deming, T. J. *Biomacromolecules*, 2012, 13, 1719-1713, which are incorporated herein by reference in their entirety.

M$_{60}$ (SEQ ID NO: 1) Alkylation Procedure B (Alkylation Procedure B)

M$_{60}$ (SEQ ID NO: 1) is alkylated with an alkyl triflate in CH$_2$Cl$_2$/MeCN. Poly(Met) is dissolved in dry DCM (10 mg/mL). Alkyl triflate (2 eq per methionine residue) is added. The reaction mixture is stirred at room temperature for 48 hours. White precipitate is generally observed after 24 hours in all cases. After 24 hours, MeCN is added to give a 1:1 MeCN: DCM mixture to solubilize the polymer, and the resulting solution is stirred for 24 more hours. The reaction is precipitated with ether to remove excess alkyl triflate and then evaporated to dryness to give the product, generally as a white solid. The product can then be dispersed in water, transferred to a 2000 MWCO dialysis bag, and then dialyzed against 0.10 M NaCl for 24 hours, followed by DI water for 48 hours with water changes twice per day. Dialysis against NaCl serves to exchange counterions so that only chloride is present as previously reported. See U.S. Patent Application Publication No. 2015/0057433 and Kramer, J. R.; Deming, T. J. *Biomacromolecules*, 2012, 13, 1719-1713, which are incorporated herein by reference in their entirety.

M$_{60}$ (SEQ ID NO: 1) Alkylation Procedure C (Alkylation Procedure C)

M$_{60}$ (SEQ ID NO: 1) was alkylated with an epoxide in AcOH as previously reported. Poly(Met) is suspended in glacial AcOH (16 mg/mL). The epoxide (3 eq per methionine residue) is added in one portion. The mixture is stirred vigorously at 37° C. After 24 h, the solution is transferred to a 2 kDa MWCO dialysis bag and dialyzed against 3 mM HCl(aq) (24 h, 3 $H_2O$ changes). The retentate is lyophilized to provide the functionalized polypeptide.

Alternatively, $M_{60}$ (SEQ ID NO: 1) is suspended in glacial AcOH (27 mg/mL). The epoxide (1.5 eq per methionine residue) is added. The mixture is stirred vigorously at 37° C. After the peptide dissolves (ca. 2-6 h), a second portion of epoxide (1.5 eq per methionine residue) is added. After 24 h, the solution is transferred to a 2 kDa MWCO dialysis bag and dialyzed against 3 mM HCl(aq) (24 h, 3 $H_2O$ changes). The retentate is lyophilized to provide the functionalized polypeptide.

See PCT Publication No. 2016/154120 and Gharakhanian, E. G.; Deming, T. J. *Biomacromolecules*, 2015, 16, 1802-1806, which are incorporated herein by reference in their entirety.

$M^R$ Demethylation Procedure a (Demethylation Procedure A)

A solution of $M^R{}_{60}$ (SEQ ID NO: 1) in 75% $EtOH_{(aq)}$ (20 mM $M^R$) is prepared in a vial and treated with APDC (5.0 eq per $M^R$). The headspace of the vial is briefly flushed with a stream of $N_2$, then rapidly capped. The mixture is stirred vigorously at 22° C. The initially homogenous solution generally becomes turbid with precipitate (polypeptide) over the course of minutes (products 25 & 26) to hours (21-24). After 24 h, the reaction mixture is centrifuged and the supernatant separated. The precipitate is triturated and then centrifuged 3× with MeOH, then 2× with $H_2O$ (both 40 μL per pmol $M^R$ in substrate) and lyophilized.

$M^R$ Demethylation Procedure B (Demethylation Procedure B)

A solution of $M^R{}_{60}$ (SEQ ID NO: 1) in 75% $EtOH_{(aq)}$ (20 mM $M^R$) is prepared in a vial and is treated with APDC (5.0 eq per $M^R$). The headspace of the vial is briefly flushed with a stream of $N_2$ and rapidly capped. The vial is vortexed until homogenous, then allowed to stand for 24 h at 22° C. The reaction mixture is directly treated with $K_2CO_3/H_2O$ to cleave the protecting group(s). The reaction mixture is transferred to a 2 kDa MWCO dialysis bag and dialyzed against 50% $MeOH_{(aq)}$ containing 3 mM HCl or 3 mM $NH_3$ (24 h, 3 solvent changes) followed by $H_2O$ (8 h, 3 $H_2O$ changes). The retentate is lyophilized to provide the functionalized polypeptide.

$M^R$ Demethylation Procedure C (Demethylation Procedure C)

A solution of $M^R{}_{60}$ (SEQ ID NO: 1) in 75% $EtOH_{(aq)}$ (20 mM $M^R$) is prepared in a vial and is treated with APDC (5.0 eq per $M^R$). The headspace of the vial is briefly flushed with a stream of $N_2$ and rapidly capped. The vial is vortexed until homogenous, then allowed to stand for 24 h at 22° C. The reaction mixture is transferred to a 2 kDa MWCO dialysis bag and dialyzed against 50% $MeOH_{(aq)}$ (24 h, 3 solvent changes) followed by $H_2O$ (8 h, 3 $H_2O$ changes). The retentate is lyophilized, to provide the functionalized polypeptide.

Example 2: Synthesis of Alkylating Agents

Ethyl 2-(oxiran-2-ylmethoxy)acetate, 9b

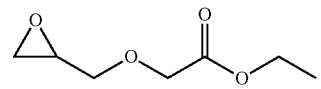

Ethyl 2-(allyloxy)acetate (0.95 g, 6.6 mmol, 1.0 eq) was dissolved in $CH_2Cl_2$ (25 mL). Commercial 70% mCPBA (2.4 g, 9.8 mmol, 1.5 eq) was added. The mixture was allowed to stir 2 days at 22° C., then cooled on an ice bath. 10% $Na_2SO_{3(aq)}$ (12 mL) was added followed by 10% $Na_2CO_{3(aq)}$ (8.7 mL, 8.3 mmol, 1.3 eq) and EtOAc (60 mL). The solution was stirred for 10 min, then transferred to a separatory funnel using EtOAc (60 mL) and $H_2O$ (40 mL) to complete the transfer. The mixture was partitioned. The organic phase was washed with sat. $NaHCO_{3(aq)}$ (60 mL) and dried over $Na_2SO_4$. The extract was concentrated in vacuo and the residue was purified by flash chromatography (35% EtOAc/Hexanes). 9b (0.73 g, 70% yield) was recovered as a colorless oil. $R_F$=0.61; 40% EtOAc/Hexanes.

$^1$H NMR (400 MHz, $CDCl_3$, 25° C.): δ 4.24 (q, J=7.1 Hz, 2H), 4.15 (d, J=16.4 Hz, 1H), 4.14 (d, J=16.5 Hz, 1H), 3.90 (dd, J=11.7, 2.9 Hz, 1H), 3.49 (dd, J=11.6, 5.9 Hz, 1H), 3.19 (m, 1H), 2.80 (dd, J=4.8, 4.2 Hz, 1H), 2.62 (dd, J=4.9, 2.7 Hz, 1H), 1.28 (t, J=7.2 Hz, 3H). $^{13}$C NMR (100 MHz, $CDCl_3$, 25° C.): δ 170.1, 72.1, 68.5, 60.9, 50.6, 44.0, 14.2. ESI-MS m/z=182.9952 [M+Na]$^+$ (calcd 183.0633 for $C_7H_{12}O_4Na$).

Methyl O-(oxiran-2-ylmethyl)-N-(2,2,2-trifluoroacetyl)-(S)-serinate, 10b

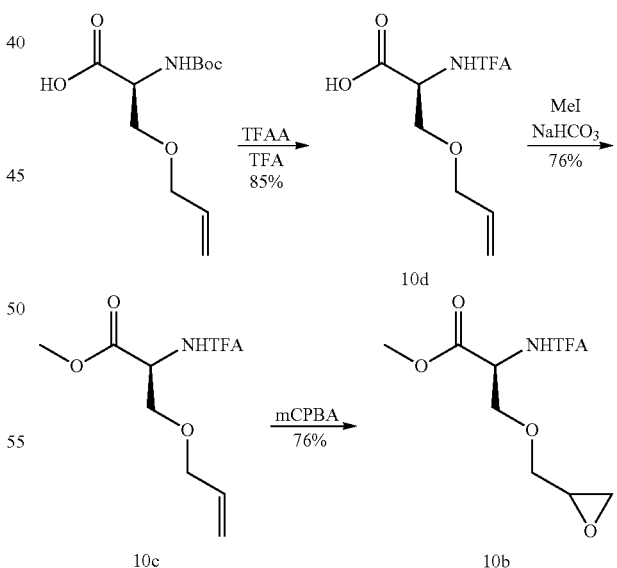

O-allyl-N-(2,2,2-trfluoroacetyl)-(S)-serine, 10d

O-allyl-N-(tert-butoxycarbonyl)-(S)-serine (6.0 g, 25 mmol, 1.0 eq) was cooled on an ice bath. TFA (20 mL) was added. TFAA (4.1 mL, 29 mmol, 1.2 eq) was added dropwise over 5 minutes. The solution was stirred for 1 h on the ice bath, then concentrated in vacuo. The residue was directly purified by flash chromatography (0:40:60 to 0.5:40:59.5 HCOOH:EtOAc:Hexanes). 10d was isolated as an orange-red viscous oil (5.0 g, 85% yield).

$^1$H NMR (400 MHz, CDCl$_3$, 25° C.): δ 7.75-7.29 (br s, 1H), 7.14 (d, J=7.7 Hz, 1H), 5.84 (m, 1H), 5.26 (m, 2H), 4.78 (m, 1H), 4.04 (dt, J=5.8, 1.3 Hz, 2H), 4.01 (dd, J=7.0, 2.8 Hz, 1H), 3.75 (dd, J=9.8, 3.4 Hz, 1H). $^{13}$C NMR (100 MHz, CDCl$_3$, 25° C.): δ 172.8, 157.6 (q, 38.5 Hz), 133.2, 118.4, 117.0 (q, J=287.0 Hz), 72.5, 68.2, 52.9. $^{19}$F{$^1$H} NMR (376 MHz, D$_2$O, 25° C.): δ −75.6. ESI-MS m/z=240.0082 [M−H]$^-$ (calcd 240.0484 for C$_8$H$_9$F$_3$NO$_4$).

Methyl O-allyl-N-(2,2,2-trifluoroacetyl)-(S)-serinate, 10c 10d (1.3 g, 5.1 mmol, 1.0 eq) and NaHCO$_3$ (0.86 g, 10 mmol, 2.0 eq) were suspended in DMF (50 mL). Methyl iodide (1.6 mL, 26 mmol, 5.0 eq) was added. The suspension was stirred at 22° C. overnight. The mixture was concentrated in vacuo and the residue was directly purified by flash chromatography (15% EtOAc/Hexanes). 10c (1.0 g, 76% yield) was recovered as a pale yellow, mobile oil. R$_F$=0.30; 15% EtOAc/Hexanes.

$^1$H NMR (400 MHz, CDCl$_3$, 25° C.): δ 7.13 (br s, 1H), 5.81 (m, 1H), 5.25 (dm, 13.9 Hz, 1H), 5.21 (dm, J=6.9 Hz, 1H), 4.72 (dm, J=8.2 Hz, 1H), 3.99 (dq, J=5.7, 1.5 Hz, 2H), 3.94 (dd, J=9.9, 3.0 Hz, 1H), 3.81 (s, 3H), 3.72 (dd, J=9.8, 3.2 Hz, 1H). $^{13}$C NMR (100 MHz, CDCl$_3$, 25° C.): δ 169.1, 157.1 (q, J=38.3 Hz), 133.5, 118.0, 117.1 (q, J=288.6 Hz), 72.3, 68.5, 53.0, 53.0. $^{19}$F{$^1$H} NMR (376 MHz, D$_2$O, 25° C.): δ −75.9. ESI-MS m/z=254.0211 [M−H]$^-$ (calcd 254.0640 for C$_9$H$_{11}$F$_3$NO$_4$).

Methyl O-(oxiran-2-ylmethyl)-N-(2,2,2-trifluoroacetyl)-(S)-serinate, 10b 10c (0.90 g, 3.5 mmol, 1.0 eq), was dissolved in a 0.45 M mCPBA solution in CH$_2$Cl$_2$ (12 mL, 5.3 mmol, 1.5 eq). The mixture was allowed to stir 3 days at 22° C., then cooled on an ice bath. 10% Na$_2$SO$_{3(aq)}$ (7 mL) was added followed by 10% Na$_2$CO$_{3(aq)}$ (4.6 mL, 4.4 mmol, 1.3 eq) and EtOAc (60 mL). The solution was stirred for 10 min. H$_2$O (20 mL) was added, then the mixture was partitioned. The organic phase was washed with sat. NaHCO$_{3(aq)}$ (30 mL) and dried over Na$_2$SO$_4$. The extract was concentrated in vacuo and the residue was purified by flash chromatography (35-40% EtOAc/Hexanes). 10b (0.73 g, 76% yield) was recovered as a colorless oil. Epoxide dr: 2:1 ($^1$H NMR). R$_F$=0.25; 40% EtOAc/Hexanes. NMR data is for major diasteriomer.

$^1$H NMR (400 MHz, CDCl$_3$, 25° C.): δ 4.69 (m, 1H), 4.10 (dd, J=10.2, 3.3 Hz, 1H), 3.81 (m, 2H), 3.77 (s, 3H), 3.73 (dd, J=10.1, 3.2 Hz, 1H), 3.43, (dd, J=12.0, 5.4 Hz, 1H), 3.07 (m, 1H), 2.76 (t, J=5.0 Hz, 1H), 2.59 (dd, J=5.0, 2.8 Hz, 1H). $^{13}$C NMR (100 MHz, CDCl$_3$, 25° C.): δ 168.0, 156.9 (q, J=37.1 Hz), 117.1 (q, J=285.5 Hz), 71.6, 70.4, 53.2, 53.0, 50.7, 43.7. $^{19}$F{$^1$H} NMR (376 MHz, D$_2$O, 25° C.): δ −75.9. ESI-MS m/z=293.9496 [M+Na]$^+$ (calcd 294.0565 for C$_9$H$_{12}$F$_3$NO$_5$Na).

Example 3: Synthesis of M$^R$ Polymers

Poly(S-methyl-L-methionine sulfonium chloride), 21a

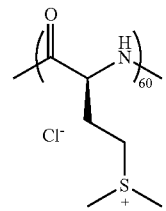

Prepared from M$_{60}$ (SEQ ID NO: 1) and methyl iodide using Alkylation Procedure A. Spectral data in agreement with those previously reported. Kramer, J. R.; Deming, T. J. *Biomacromolecules*, 2012, 13, 1719-1713.

Poly(S-ethyl-L-methionine sulfonium chloride), 22a

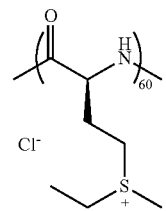

Prepared from M$_{60}$ (SEQ ID NO: 1) and ethyl triflate using Alkylation Procedure B. Yield: 99%. $^1$H NMR (400 MHz, D$_2$O, 25° C.): δ 4.68-4.55 (br m, 1H), 3.60-3.30 (br m, 4H), 2.98 (d, J=5.2 Hz, 3H), 2.51-2.17 (br m, 2H), 1.50 (dt, J=7.4, 2.8 Hz, 3H).

Poly(S-(n-propyl)-L-methionine sulfonium chloride). 23a

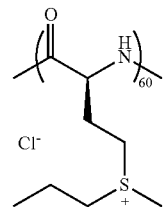

Prepared from M$_{60}$ (SEQ ID NO: 1) and propyl triflate using Alkylation Procedure B. Yield: 97%.

$^1$H NMR (400 MHz, D$_2$O, 25° C.): δ 4.71-4.53 (br m, 1H), 3.74-3.23 (br m, 4H), 2.98 (d, J=5.2 Hz, 3H), 2.59-2.14 (br m, 2H), 2.05-1.79 (br m, 2H), 1.11 (t, J=7.3 Hz, 3H).

Poly(S-(n-butyl)-L-methionine sulfonium chloride), 24a

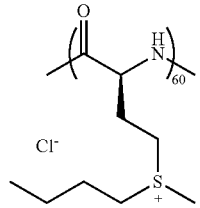

Prepared from M$_{60}$ (SEQ ID NO: 1) and butyl triflate using Alkylation Procedure B. Yield: 96%.

$^1$H NMR (400 MHz, D$_2$O, 25° C.): δ 4.72-4.50 (br m, 1H), 3.62-3.29 (br m, 4H), 2.99 (d, J=5.0 Hz, 3H), 2.58-2.17 (br m, 2H), 1.85 (m, 2H), 1.54 (sext, J=7.3 Hz, 2H), 0.99 (t, J=7.3 Hz, 3H).

Poly(S-allyl-L-methionine sulfonium chloride), 25a

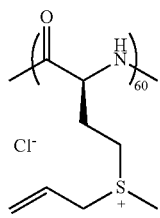

Prepared from M$_{60}$ (SEQ ID NO: 1) via a modified Alkylation Procedure A. M$_{60}$ (SEQ ID NO: 1) (16 mg, 0.122 mmol M, 1.0 eq) was suspended in AcOH. Allyl bromide (32 μL, 0.37 mmol, 3.0 eq) was added. The mixture was vigorously stirred at 37° C. After 24 h, the limpid solution was transferred to a 2 kDa MWCO dialysis bag and dialyzed against 3 mM HCl$_{(aq)}$ (24 h, 3 H$_2$O changes). The retentate was lyophilized, to provide 25a (25 mg, 99% Yield). $^1$H NMR (400 MHz, D$_2$O, 25° C.): δ 6.07-5.89 (br m, 1H), 5.84-5.61 (br m, 2H), 4.66-4.55 (br m, 1H), 4.26-4.03 (br m, 2H), 3.57-3.32 (br m, 2H), 2.94 (t, J=6.0 Hz, 3H), 2.53-2.18 (br m, 2H).

Poly(S-benzyl-L-methionine sulfonium chloride), 26a

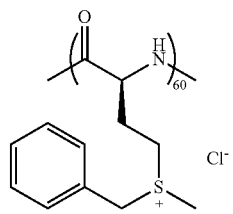

Prepared from M$_{60}$ (SEQ ID NO: 1) and benzyl bromide using Alkylation Procedure A. Spectral data in agreement with those previously reported. Kramer, J. R.; Deming, T. J. *Biomacromolecules*, 2012, 13, 1719-1713.

Poly(S-(3-azido-2-hydroxypropyl)-L-methionine sulfonium chloride), 27a

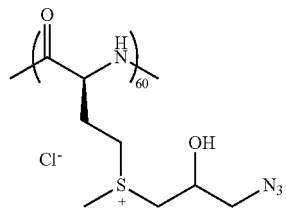

Prepared from M$_{60}$ (SEQ ID NO: 1) and glycidyl azide using Alkylation Procedure C. Spectral data in agreement with those previously reported. Gharakhanian, E. G.; Deming, T. J. *Biomacromolecules*, 2015, 16, 1802-1806.

Poly(S-(2-hydroxy-3-(2,2,2-trifluoroacetamido)propyl)-L-methionine sulfonium chloride), 28a

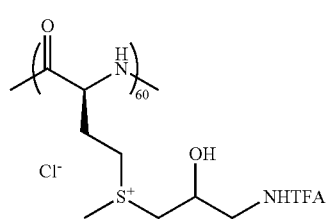

Prepared from M$_{60}$ (SEQ ID NO: 1) and glycidyl trifluoroacetamide using Alkylation Procedure C. Spectral data in agreement with those previously reported. Gharakhanian, E. G.; Deming, T. J. *Biomacromolecules*, 2015, 16, 1802-1806.

Poly(S-(3-((1-ethoxy-1-oxoeth-2-yl)oxy)-2-hydroxypropyl)-L-methionine sulfonium chloride), 29a

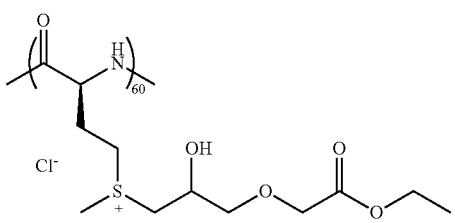

Prepared from M$_{60}$ (SEQ ID NO: 1) and 9b using Alkylation Procedure C. Dialysis was conducted against 6 mM NaCl (24 h, 3 H$_2$O changes) then H$_2$O (8 h, 3 H$_2$O changes) instead of HCl$_{(aq)}$, to reduce hydrolysis of the uncharacteristically labile ethyl ester. Recovered product showed 34% ethyl ester deprotection. Yield 96%.

$^1$H NMR (400 MHz, D$_2$O, 25° C.): δ 4.70-4.51 (br m, 1H), 4.51-4.35 (br m, 1H), 4.35-4.21 (br m, 2.6H), 4.01 (s, 0.6H), 3.97-3.40 (br m, 6H), 3.21-2.92 (br m, 3H), 2.55-2.18 (br m, 2H), 1.30 (t, J=7.2 Hz, 2H).

Poly(S-(3-(((S)-1-methoxy-1-oxo-2-(2,2,2-trifluoro-acetamido)prop-3-yl)oxy)-2-hydroxypropyl)-L-methionine sulfonium chloride), 30a

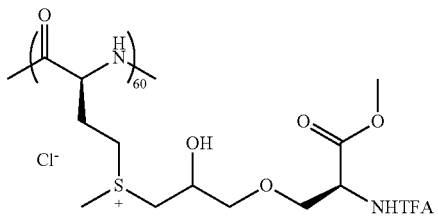

Prepared from $M_{60}$ (SEQ ID NO: 1) and 10b using Alkylation Procedure C. Yield: 96%

$^1$H NMR (400 MHz, $D_2O$, 25° C.): δ 4.98-4.89 (br m, 1H), 4.71-4.56 (br m, 1H), 4.44-4.32 (br m, 1H), 4.06-4.96 (br m, 2H), 3.83 (s, 3H), 3.79-3.34 (br m, 6H), 3.15-2.96 (br m, 3H), 2.58-2.17 (br m, 2H). $^{19}$F{$^1$H} NMR (376 MHz, $D_2O$, 25° C.): −75.1.

Poly(S-(2-hydroxy-4,7,10,13-tetraoxatetradecyl)-L-methionine sulfonium chloride), 31a

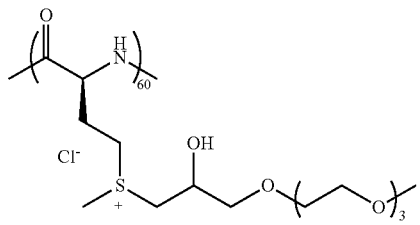

Prepared from $M_{60}$ (SEQ ID NO: 1) and 2-(2,5,8,11-tetraoxadodecyl)oxirane using Alkylation Procedure C. Spectral data in agreement with those previously reported. Gharakhanian, E. G.; Deming, T. J. *Biomacromolecules*, 2015, 16, 1802-1806.

Poly(S-((3-(2-(6-deoxy-D-galactopyranosid-6-yl)oxy)ethoxy)-2-hydroxypropyl)-L-methionine sulfonium chloride), 32a

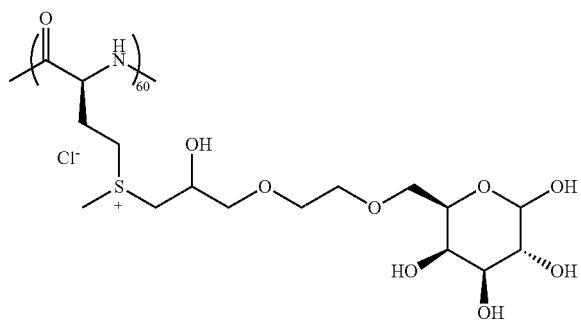

Prepared from $M_{60}$ (SEQ ID NO: 1) and 2-(2-((1,2:3,4-di-O-isopropylidene-6-deoxy-α-D-galactopyranosid-6-yl)oxy)ethoxymethyl)oxirane using Alkylation Procedure C followed by acid deprotection of the isopropylidene protecting groups. Spectral data in agreement with those previously reported. Gharakhanian, E. G.; Deming, T. J. *Biomacromolecules*, 2015, 16, 1802-1806.

Example 4: Studies of Demethylation Reaction Conditions

Example Reaction of $M^R_{60}$ (SEQ ID NO: 1) with Various Nucleophiles

A stock solution of 31a (22 mg/mL, 55 mM $M^R$) in 95% EtOH was prepared. A buffered ethanol solution was prepared by mixing equal volumes of 0.27 M NaOAc in 95% EtOH with 0.27 M AcOH in 95% EtOH. 31a stock (0.33 mL, 0.018 mmol $M^R$, 1.0 eq) was diluted with buffered ethanol (0.33 mL). Nucleophile (KI, 2-mercaptopyridine, potassium thioaceate or APDC) (0.090 mmol, 5.0 eq) was added if required. The reaction mixture was vortexed briefly and allowed to stand at 22° C. for 24 h. The reaction mixture was transferred to a 2 kDa MWCO dialysis bag and dialyzed against $H_2O$ (36 h, 5 $H_2O$ changes). The retentate was lyophilized and the reaction selectivity determined by $^1$H NMR.

For thioglycolate the procedure was as above, except a NaOAc solution was used instead of buffer. Therefore, 31a stock (0.33 mL, 0.018 mmol $M^R$, 1.0 eq) was diluted with 0.27 M NaOAc in 95% EtOH (0.33 mL). Thioglycolic Acid (0.090 mmol, 6.2 µL, 5.0 eq) was added. From there the procedure was as above.

Comparison of Extent of Reaction Conversion

An 31a stock solution (7.8 mg/mL, 20 mM $M^R$) in 75% $EtOH_{(aq)}$ was prepared. 31a stock (0.65 mL, 0.013 mmol $M^R$, 1.0 eq) was added to a vial containing an accurately weighed quantity of APDC (11 mg, 0.064 mmol, 5.0 eq) or potassium thioacetate (7.4 mg, 0.064 mmol, 5.0 eq). The headspace of the vial was briefly flushed with $N_2$ then rapidly capped. The reaction was stirred for 3.0 h at 22° C. The reaction was then immediately quenched with 3 drops of con. $HCl_{(aq)}$, transferred to a 2 kDa MWCO dialysis bag and dialyzed against 3 mM $HCl_{(aq)}$ (4 h, 2 $H_2O$ changes) followed by $H_2O$ (24 h, 3 $H_2O$ changes).

The retentate was lyophilized and extent of reaction conversion determined by $^1$H NMR.

Influence of $EtOH/H_2O$ solvent composition on demethylation rate

As above, using 31a stock solutions in 75% $EtOH_{(aq)}$, 50% $EtOH_{(aq)}$ or 0% $EtOH_{(aq)}$. Aliquots were removed from the reaction and quenched at either 3 h or 24 h time points.

Conversion Vs. Time Study

As preceding experiments, this study was performed using a stock solution of 31a in 75% $EtOH_{(aq)}$. Aliquots were removed from the reaction mixture and quenched at 0.33, 0.83, 2.0, 3.0, 5.0, 8.0 and 22.0 h time points.

For the 0.00 h time point a slight deviation was made. 31a stock (0.65 mL, 0.013 mmol $M^R$, 1.0 eq) was treated with 3 drops of con. $HCl_{(aq)}$. APDC (11 mg, 0.064 mmol, 5.0 eq) was added. The mixture was vortexed until homogenous and allowed to stand for 2 minutes. The mixture was transferred to dialysis and isolated as in preceding experiments.

Example 5: Details for Synthesis of Specific R—C$^H$ Polymers

Poly(L-Methionine), 21, 25-26

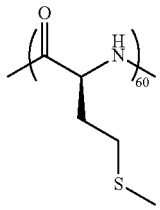

Prepared from 21a, 25a or 26a using Demethylation Procedure A. 25a and 26a became turbid with precipitate (polypeptide) in <10 min, while for 1a precipitate began forming after ~6 h.

$^1$H NMR (400 MHz, D-TFA, 25° C.): δ 4.93-4.70 (br m, 1H) 2.77-2.53 (br m, 2H) 2.29-1.94 (br m, 5H).

Poly[(S-ethyl-L-homocysteine)$_{0.93}$-stat-(L-Methionine)$_{0.07}$], 22

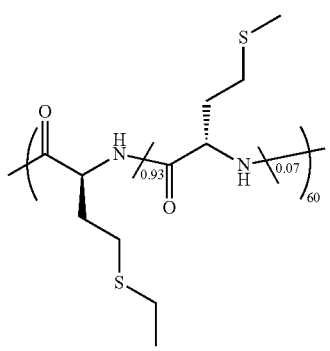

Prepared from 22a using Demethylation Procedure A $^1$H NMR (400 MHz, D-TFA, 25° C.): δ 4.98-4.82 (br m, 1.07H), 2.88-2.55 (br m, 4.14H), 2.38-2.03 (br m, 2.4H), 1.53-1.12 (t, J=7.6 Hz, 3H).

Poly(S-propyl-L-homocysteine), 23

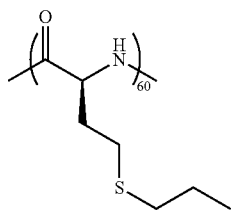

Prepared from 23a using Demethylation Procedure A.

$^1$H NMR (400 MHz, D-TFA, 25° C.): δ 4.93-4.77 (br m, 1H), 2.89-2.63 (br m, 2H), 2.59 (t, J=7.4 Hz, 2H), 2.27-2.07 (br m, 2H), 1.65 (sext, J=7.4 Hz, 2H), 1.00 (t, J=7.4 Hz, 3H).

Poly(S-Butyl-L-homocysteine), 24

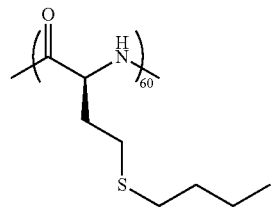

Prepared from 24a using Demethylation Procedure A.

$^1$H NMR (400 MHz, D-TFA, 25° C.): δ 5.52-5.13 (br m, 1H), 3.32-3.09 (br m, 2H), 3.05 (t, J=7.6 Hz, 2H), 2.73-2.52 (br m, 2H), 2.03 (p, J=7.6 Hz, 2H), 1.86 (sext, J=7.6 Hz, 2H), 1.35 (t, J=7.6 Hz, 3H).

Poly(S-(3-azido-2-hydroxypropyl)-L-homocysteine), 27

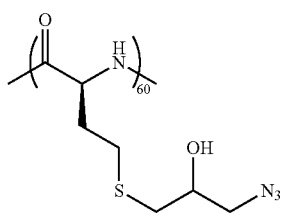

Prepared from 27a using Demethylation Procedure A $^1$H NMR (400 MHz, D-TFA, 25° C.): δ 5.26-4.68 (br m, 1H), 4.36-4.07 (br m, 1H), 3.89-3.43 (br m, 2H), 3.16-2.58 (br m, 4H), 2.43-2.04 (br m, 2H).

Poly(S-(3-ammonio-2-hydroxypropyl)-L-homocysteine chloride), 28

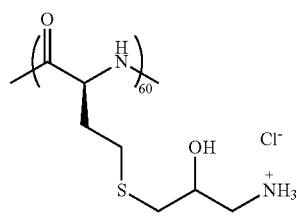

Prepared from 28a using Demethylation Procedure B. Deprotection conditions: H$_2$O (7.5 µL per µmol R—C$^H$) and K$_2$CO$_3$ (10 eq per R—C$^H$) were added. Allowed to stir vigorously at 40° C. for 48 h. Dialysis conditions: 50% MeOH$_{(aq)}$ containing 3 mM HCl (24 h, 3 solvent changes) followed by H$_2$O (8 h, 3 H$_2$O changes).

$^1$H NMR (400 MHz, D$_2$O, 25° C.): δ 4.67-4.39 (br m, 1H), 4.18-3.97 (br m, 1H) 3.32 (d, J=12.9 Hz, 1H), 3.04 (dd, J=12.9, 9.6 Hz, 1H), 2.95-2.49 (br m, 4H), 2.23-2.00 (br m, 2H).

Poly(ammonium S-(3-(carboxylatomethoxy)-2-hydroxypropyl)-L-homocysteine), 29

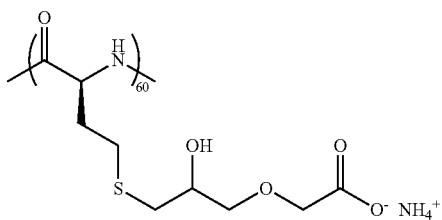

Prepared from 29a using Demethylation Procedure B. Deprotection conditions: $H_2O$ (5.5 μL per μmol R—$C^H$) and $K_2CO_3$ (6 eq per R—$C^H$) were added. The mixture was allowed to stir 18 h at 37° C. Dialysis conditions: 50% $MeOH_{(aq)}$ containing 3 mM $NH_3$ (24 h, 3 solvent changes) followed by $H_2O$ (8 h, 3 $H_2O$ changes).

$^1$H NMR (400 MHz, $D_2O$, 25° C.): δ 4.49-4.21 (br m, 1H), 4.22-3.86 (br m, 3H), 3.81-3.51 (br m, 2H), 3.27-3.55 (br m, 4H), 2.42-1.97 (br m, 2H).

Poly(S—((S)-3-2-ammonio-2-carboxylatoethoxy)-2-hydroxypropyl)-L-homocysteine), 30

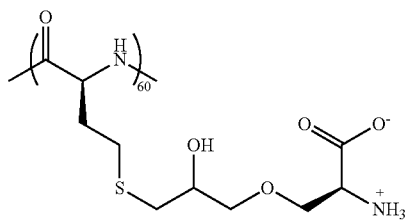

Prepared from 30a using Demethylation Procedure B. Deprotection conditions: $H_2O$ (7.5 μL per μmol R—$C^H$) and $K_2CO_3$ (10 eq per R—$C^H$) were added. Allowed to stir vigorously at 40° C. for 48 h. Dialysis conditions: 50% $MeOH_{(aq)}$ containing 3 mM $NH_3$ (24 h, 3 solvent changes) followed by $H_2O$ (8 h, 3 $H_2O$ changes).

$^1$H NMR (400 MHz, $D_2O$, 25° C.): δ 4.8-4.7 (1H)*, 4.61-4.16 (br m, 1H), 4.15-3.82 (br m, 3H), 3.82-3.45 (br m, 2H), 3.15-2.48 (br m 4H), 2.48-1.84 (br m, 2H). *Obscured by solvent residual peak.

Poly(S-(2-hydroxy-4,7,10,13-tetraoxatetradecyl)-L-homocysteine), 31

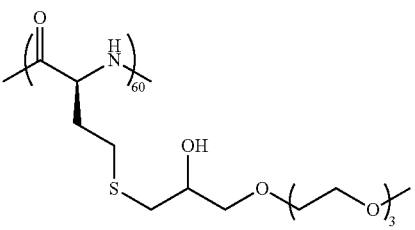

Prepared from 31a using Demethylation Procedure C.

$^1$H NMR (400 MHz, $D_2O$, 25° C.): δ 4.50-4.15 (br m, 1H), 4.07-3.92 (br m, 1H), 3.85-3.51 (br m, 14H), 3.41 (s, 3H), 3.10-2.57 (br m, 4H), 2.57-1.96 (br m, 2H).

Poly(S-((3-(2-(6-deoxy-D-galactopyranosid-6-yl)oxy)ethoxy)-2-hydroxypropyl)-L-homocysteine), 32

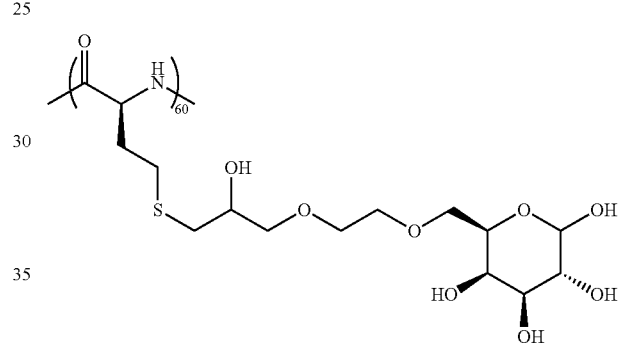

Prepared from 32a using Demethylation Procedure C. The product was found to contain a 1:2 ratio of α:β anomers ($^1$H NMR) in $D_2O$ at 25° C. Identification of anomers based on reported spectral assignments of D-galactose.[6]

$^1$H NMR (400 MHz, $D_2O$, 25° C.): δ 5.29 (m, 0.34H), 4.62 (d, J=7.8 Hz, 0.66H), 4.54-4.29 (br m, 1H), 4.29-3.41 (br m, 13H), 3.10-2.56 (br m, 4H), 2.56-1.84 (br m, 2H).

Additional R—$C^H$ Polymers

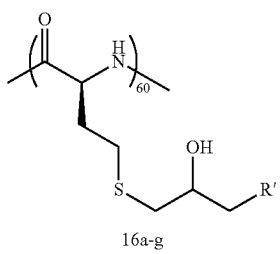

16a-g

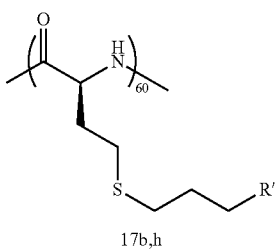

17b,h

| Label | R | Alkylating Agent | Alkylation Procedure | Demethylation Procedure |
|---|---|---|---|---|
| 16a | ~NH$_3^+$ Cl$^-$ | (epoxide)—NH—TFA | C | B |

-continued

| Label | R | Alkylating Agent | Alkylation Procedure | Demethylation Procedure |
|---|---|---|---|---|
| 16b | -O-CH₂CH₂-NH₃⁺ Cl⁻ | epoxide-O-CH₂CH₂-NH-TFA | C | B |
| 17b | -O-CH₂CH₂-NH₃⁺ Cl⁻ | TfO-CH₂CH₂CH₂-O-CH₂CH₂-NH-TFA | B | B |
| 16c | -O-CH₂CH₂-NH₂⁺(i-Pr) Cl⁻ | epoxide-O-CH₂CH₂-N(i-Pr)(TFA) | C | B |
| 16d | -O-CH₂-CH(NH₃⁺ Cl⁻)-C(O)NH₂ | epoxide-O-CH₂-CH(NH-Me)-C(O)NH₂ | C | B |
| 16e | -O-CH₂-CH(NH₃⁺ Cl⁻)-C(O)NH-i-Pr | epoxide-O-CH₂-CH(NH-TFA)-C(O)NH-i-Pr | C | B |
| 16f | -O-CH₂-C(O)O⁻ Na⁺ | epoxide-O-CH₂-C(O)-OEt | C | B |
| 16g | -O-CH₂-CH(NH₃⁺)-C(O)O⁻ | epoxide-O-CH₂-CH(NH-TFA)-C(O)OMe | C | B |
| 17h | -O-CH₂CH₂-O-CH₂CH₂-NH₃⁺ Cl⁻ | TfO-CH₂CH₂CH₂-O-CH₂CH₂-O-CH₂CH₂-NH-TFA | B | B |

Example 6: Peptide Modifications

H-YGGF(M$^{N3}$)-NH$_2$, 14 (SEQ ID NO: 3)

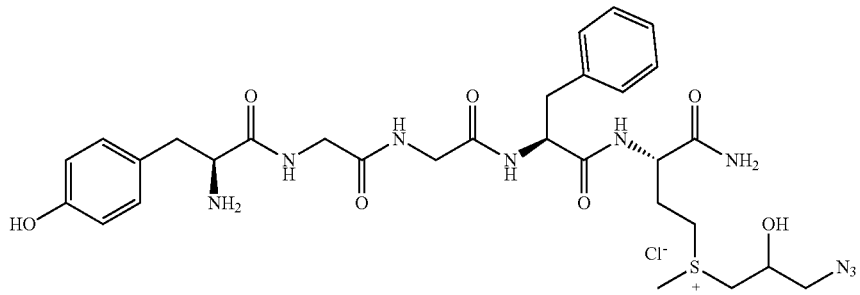

A 35 mM solution of 13 in AcOH was prepared. A 150 mM solution of glycidyl azide in AcOH was prepared immediately before use. The solution of 13 (0.11 mL, 3.8 μmol, 1.0 eq) was treated with the glycidyl azide solution (0.25 mL, 38 μmol, 10 eq). The mixture was stirred on a 30° C. H$_2$O bath for 24 h. The volatiles were removed under high vacuum at 22° C. The residue was triturated with Et$_2$O (2×1.0 mL) then dissolved in 10 mM HCl$_{(aq)}$ (1 mL). The solution was lyophilized to provide 14 (2.4 mg, 88% yield) as a colorless amorphous solid.
ESI-MS m/z=672.2780 [M]+(calcd 672.2927 for C$_{30}$H$_{42}$N$_9$O$_7$S).

H-YGGF(N$_3$—C$^H$)—NH$_2$, 15 (SEQ ID NO: 4)

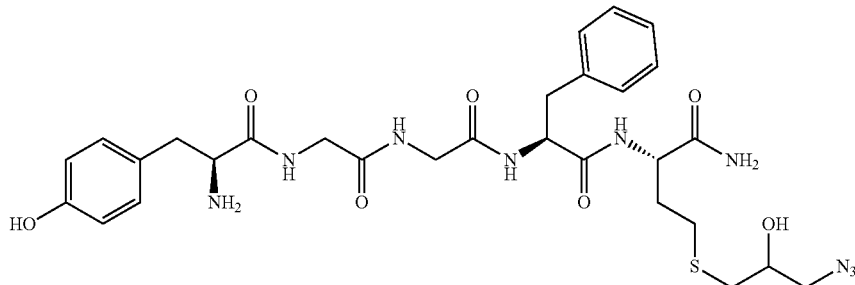 [SMILES: [N-]=[N+]=NCC(O)CSCC[C@H](NC(=O)[C@H](Cc1ccccc1)NC(=O)CNC(=O)CNC(=O)[C@@H](N)Cc1ccc(O)cc1)C(N)=O]

14 (2.2 mg, 3.3 μmol, 1.0 eq) was dissolved in an 82 mM APDC solution in 75% EtOH$_{(aq)}$ (0.40 mL, 33 μmol, 10 eq). The solution was stirred for 26 h under N$_2$, then directly analyzed by HPLC-MS. Crude 15 was found to be 84% pure (% a/a) by UV (280.4 nm). ESI-MS concomitantly showed [15+TFA]$^-$ (calcd: 770.3 m/z, found: 770.2 m/z). The reaction mixture was also analyzed by high resolution ESI-MS. ESI-MS m/z=658.2784 [M+H]$^+$ (calcd 658.2771 for C$_{29}$H$_{40}$N$_9$O$_7$S).

Example 7: General Synthetic Procedures for OEG-Functionalized Peptides

Poly(DL-methionine)$_{60}$, rac-M$_{60}$

Prepared analogously to M$_{60}$ (SEQ ID NO: 1) using DL-Met NCA. Found DP=56, designated as rac-M$_{60}$.

$^1$H NMR (400 MHz, d-TFA, 25° C.): 4.81 (m, 1H), 2.64 (m, 2H), 2.36-1.89 (br m, 5H).

2-acetoxyethyl glycidyl ether

A solution of 2-(allyloxy)ethyl acetate[32] (1.0 g, 6.9 mmol, 1 eq) in CH$_2$Cl$_2$ (25 mL) was cooled on an ice bath. mCPBA (2.6 g, 10.4 mmol, 1.5 eq) was added in one portion. The mixture was allowed to warm to room temperature and stirred for 48 h. The reaction was quenched on an ice bath with 10% Na$_2$SO$_3$ (13 mL) and Na$_2$CO$_3$ (11 mL). The mixture was stirred for 5 min and transferred to a separatory funnel using EtOAc (30 mL) to complete the transfer. The organic phase was partitioned, and washed with sat. aqueous NaHCO$_3$ (30 mL) followed by brine (30 mL). The organic extract was dried over Na$_2$SO$_4$ and concentrated by rotary evaporation. The residue was purified by flash chromatography (50% EtOAc/hexanes) to provide 2-acetoxyethyl glycidyl ether (0.79 g, 71% yield) as a colorless liquid. R$_F$=0.40; 50% EtOAc/Hexanes.
$^1$H NMR (400 MHz, CDCl$_3$, 25° C.): 4.23 (t, J=4.9 Hz, 2H), 3.82 (dd, J=11.7, 2.9 Hz, 1H), 3.17 (m, 2H), 3.43 (dd, J=11.7, 6.0 Hz, 1H), 3.16 (m, 1H), 2.80 (dd, J=5.0, 4.2 Hz, 1H), 2.61 (dd, J=5.0, 2.7 Hz, 1H), 2.09 (s, 3H). $^{13}$C NMR (100 MHz, CDCl$_3$, 25° C.): δ 170.9, 71.8, 69.2, 50.7, 44.0, 20.8. ESI-MS m/z=182.9794 [M+Na]+(calcd 183.0633 for C$_7$H$_{12}$O$_4$Na).

M$_{60}$ (SEQ ID NO: 1) Alkylation

M$_{60}$ (SEQ ID NO: 1) was alkylated with OEG-epoxides (3 eq per Met residue) in AcOH at 37° C., as previously reported, to provide 1a-f and 4a. Gharakhanian, E. G.;

Deming, T. J. Versatile synthesis of stable, functional polypeptides via reaction with epoxides. *Biomacromolecules* 2015, 16, 1802-1806.

M$_{60}$ (SEQ ID NO: 1) Sulfonium Demethylation

M$_{60}$ (SEQ ID NO: 1) sulfonium derivatives (1a-f, 4a) were demethylated with APDC (5 eq per sulfonium residue) in 75% EtOH as described above.

Example 8: Modification of OEG-HCy Polymers

Poly(S-(2-acetoxy-4,7,10,13-tetraoxatetradecyl)-L-homocysteine), 3a

A solution of 2f (6.0 mg, 0.020 mmol OH-groups, 1 eq) in THF (0.50 mL) was treated with Ac$_2$O (19 µL, 0.20 mmol, 10 eq) followed by TEA (28 µL, 0.20 mmol, 10 eq). The mixture was allowed to stand 20 h at 22° C. The reaction mixture was transferred to a 2 kDa MWCO dialysis bag and dialyzed against H$_2$O (48 h, 6 H$_2$O changes). The retentate lyophilized, to provide 3a (6.1 mg, 90% yield).

$^1$H NMR (400 MHz, D$_2$O, 25° C.): 5.37-5.03 (br m, 1H), 4.48-4.11 (br m, 1H), 4.11-3.49 (br m, 14H), 3.41 (s, 3H), 3.18-2.46 (br m, 4H), 2.46-1.81 (br m, 5H).

Poly(S-(2-(((2-methoxyethoxy)carbonyl)oxy)-4,7,10,13-tetraoxatetradecyl)-L-homocysteine), 3b A solution of 2f (6.0 mg, 0.020 mmol OH-groups, 1 eq) in THF (0.50 mL) was treated with 2-methoxyethyl chloroformate (24 µL, 0.20 mmol, 10 eq) followed by pyridine (17 µL, 0.20 mmol, 10 eq). The product was purified and isolated analogously to 3a, to provide 3b (7.7 mg, 99% yield).

$^1$H NMR (400 MHz, D$_2$O, 25° C.): 5.20-4.91 (br m, 1H), 4.56-4.08 (br m, 3H), 4.05-3.19 (br m, 22H), 3.11-2.58 (m, 6H), 3.11-2.58 (br m, 4H), 2.47-1.99 (br m, 2H).

Poly(S-(2-hydroxy-4,7-dioxaoctyl)-L-homocysteine sulfoxide), 5a 2b (9.5 mg, 0.038 mmol thioether groups, 1 eq) was dissolved in HFiP (0.75 mL). The solution was treated with 30% aqueous H$_2$O$_2$ (11 µL, 0.10 mmol, 2.8 eq), vortexed briefly and allowed to stand for 16 h. The reaction mixture was quenched with 10% Na$_2$SO$_3$ (75 µL), transferred to a 2 kDa MWCO dialysis bag and dialyzed against H$_2$O (24 h, 4 H$_2$O changes). The retentate lyophilized, to provide 5a (9.6 mg, 95% yield).

$^1$H NMR (400 MHz, D$_2$O, 25° C.): 4.59-4.19 (br m, 2H), 3.94-3.18 (br m, 13H), 2.75-2.26 (br m 2H). ATR-FTIR: 1650, 1542, 1100, 1033 cm$^{-1}$.

Poly(S-(2-hydroxy-4,7-dioxaoctyl)-L-homocysteine sulfone), 5b 2b (10.1 mg, 0.041 mmol thioether groups, 1 eq) was suspended in HCOOH (0.50 mL). The mixture was cooled to 8° C. and treated with 30% aqueous H$_2$O$_2$ (19 µL, 0.19 mmol, 5 eq), then allowed to stir at room temp for 16 h. The reaction mixture was quenched with 10% aqueous NaHSO$_3$ (0.1 mL), transferred to a 2 kDa MWCO dialysis bag and dialyzed against 3 mM aqueous HCl (48 h, 6 H$_2$O changes) followed by H$_2$O (24 h, 3 H$_2$O changes). The retentate lyophilized, to provide 5b (10.9 mg, 96% yield).

$^1$H NMR (400 MHz, D$_2$O, 25° C.): 4.60-4.49 (br m, 1H), 4.38-4.25 (br m, 1H), 3.90-3.27 (br m, 9H), 3.27-2.93 (br m, 4H), 2.50-2.10 (br m, 2H). ATR-FTIR: 1651, 1550, 1284, 1115 cm$^{-1}$.

Example 9: Details of OEG Sulfonium Polymers

Poly(S-(3-(2-hydroxyethoxy)-2-hydroxypropyl)-L-methionine sulfonium chloride), 1a

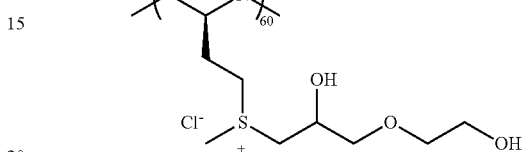

Prepared by the Alkylation Procedure C using 2-hydroxyethyl glycidyl ether.

$^1$H NMR (400 MHz, D$_2$O, 25° C.): 4.72-4.55 (br m, 1H), 4.52-4.25 (br m, 1H), 3.83-3.39 (br m, 10H), 3.15 (m, 3H), 2.61-2.20 (br m, 2H).

Poly(S-(3-(2-methoxyethoxy)-2-hydroxypropyl)-L-methionine sulfonium chloride), 1b

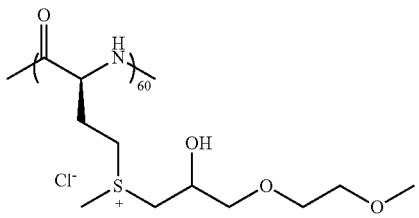

Prepared by the Alkylation Procedure C using 2-methoxyethyl glycidyl ether.

$^1$H NMR (400 MHz, D$_2$O, 25° C.): 4.71-4.51 (br m, 1H), 4.51-4.29 (br m, 1H), 3.87-3.44 (br m, 10H), 3.41 (s, 3H), 3.11 (m, 3H), 2.59-2.12 (br m, 2H).

Poly(S-(3-(2-methoxyethoxy)-2-hydroxypropyl)-DL-methionine sulfonium chloride), rac-1b

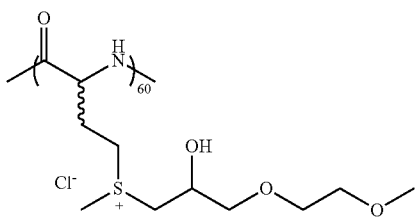

Prepared by the Alkylation Procedure C, substituting M$_{60}$ (SEQ ID NO: 1) with rac-M$_{60}$ using 2-methoxyethyl glycidyl ether.

$^1$H NMR (400 MHz, D$_2$O, 25° C.): 4.72-4.52 (br m, 1H), 4.50-4.25 (br m, 1H), 3.89-3.45 (br m, 10H), 3.42 (s, 3H), 3.18-2.93 (br m, 3H), 2.66-2.19 (br m, 2H).

Poly(S-(3-(2-acetoxyethoxy)-2-hydroxypropyl)-L-methionine sulfonium chloride), 1c

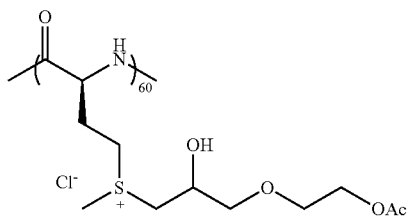

Prepared by the Alkylation Procedure C using 2-acetoxyethyl glycidyl ether.

$^1$H NMR (400 MHz, D$_2$O, 25° C.): 4.73-4.34 (br m, 1H), 4.51-4.34 (br m, 1H), 4.30 (t, J=4.2 Hz, 2H), 3.89-3.47 (br m, 8H), 3.09 (m, 3H), 2.56-2.23 (br m, 2H), 2.15 (s, 3H).

Poly(S-(2-hydroxy-4,7,10-trioxaundecyl)-L-methionine sulfonium chloride), 1d

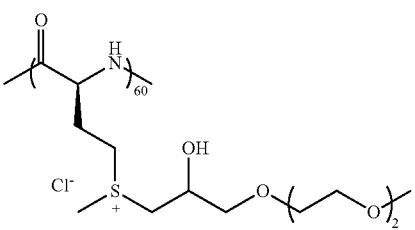

Prepared by the Alkylation Procedure C using (2-(2-methoxyethoxy)ethyl) glycidyl ether.

$^1$H NMR (400 MHz, D$_2$O, 25° C.): 4.72-4.54 (br m, 1H), 4.46-4.33 (br m, 1H), 3.82-3.44 (br m 14H), 3.40 (s, 3H), 3.08 (m, 3H), 2.63-2.19 (m, 2H).

Poly(S-(2-hydroxy-4,7,10-trionadodecyl)-T-methionine sulfonium chloride), 1e

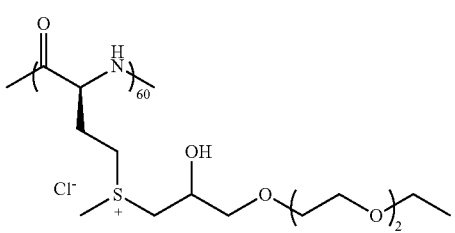

Prepared by the Alkylation Procedure C using (2-(2-ethoxyethoxy)ethyl) glycidyl ether.

$^1$H NMR (400 MHz, D$_2$O, 25° C.): 4.73-4.56 (br m, 1H), 4.52-4.32 (br m, 1H), 3.84-3.43 (br m, 16H), 3.09 (m, 3H), 2.60-2.21 (br m, 2H), 1.23 (t, J=7.0 Hz, 3H).

Poly(S-(2-hydroxy-4,7,10,13-tetraoxatetradecyl)-L-methionine sulfonium chloride), 1f

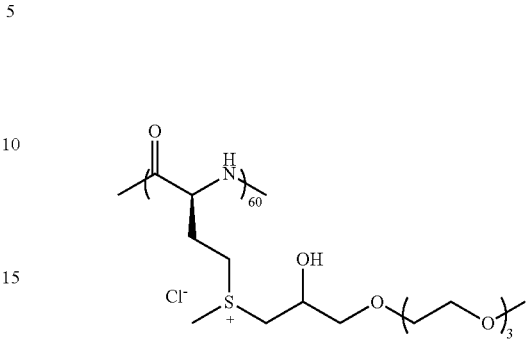

Prepared as described above.

Poly[(S-(2-hydroxy-4,7,10-trioxaundecyl)-L-methionine sulfonium chloride)$_{0.5}$-stat-(S-(2-hydroxy-4,7,10-trioxadodecyl)-L-methionine sulfonium_chloride)$_{0.5}$], 4a

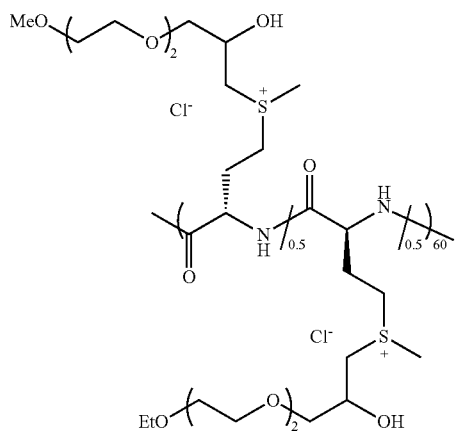

Prepared by the Alkylation Procedure C, using a 1:1 mixture of (2-(2-methoxyethoxy)ethyl) glycidyl ether (1.5 eq) and (2-(2-ethoxyethoxy)ethyl) glycidyl ether (1.5 eq). The distribution of the copolymer matched the ratio of the epoxide feed, as determined by comparing the integration of the terminating —OCH$_3$ and —OCH$_2$CH$_3$ group resonances in the $^1$H NMR spectrum of the product.

$^1$H NMR (400 MHz, D$_2$O, 25° C.): 4.70-4.58 (br m, 1H), 4.50-4.30 (br m, 1H), 3.92-3.45 (br m, 15H), 3.40 (s, 1.5H), 3.08 (m, 3H), 2.58-2.19 (br m, 2H), 1.22 (t, J=7.0 Hz, 1.5H).

Example 10: Details of Specific OEG-Hcy Polymers

Poly(S-(3-(2-hydroxyethoxy)-2-hydroxypropyl)-L-homocysteine), 2a

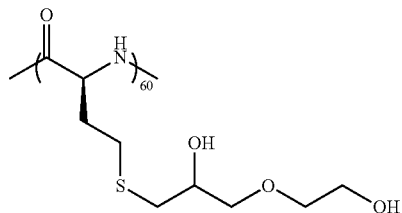

Prepared from 1a using the Demethylation Procedure A.

$^1$H NMR (400 MHz, D$_2$O, 25° C.): 4.54-4.12 (br m, 1H), 4.08-3.92 (br m, 1H), 3.80-3.55 (br m, 6H), 3.08-2.53 (br m, 4H), 2.53-1.96 (br m, 2H).

Poly(S-(3-(2-methoxyethoxy)-2-hydroxypropyl)-L-homocysteine), 2b

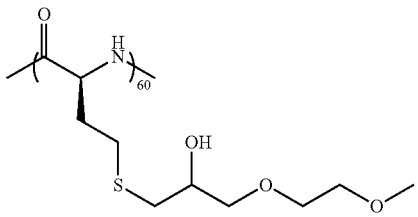

Prepared from 1b using Demethylation Procedure A.

$^1$H NMR (400 MHz, D$_2$O, 25° C.): 4.49-4.17 (br m, 1H), 4.09-3.93 (br m, 1H), 3.86-3.48 (br m, 6H), 3.52 (s, 3H), 3.10-2.56 (br m, 4H), 2.44-2.02 (br m, 2H).

Poly(S-(3-(2-methoxyethoxy)-2-hydroxypropyl)-DL-homocysteine), rac-2b

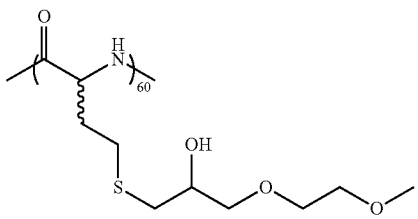

Prepared from rac-1b using Demethylation Procedure A.

$^1$H NMR (400 MHz, D$_2$O, 25° C.): 4.71-4.16 (br m, 1H), 4.13-3.86 (br m, 1H), 3.83-3.50 (br m, 6H), 3.42 (s, 3H), 3.01-2.47 (br m, 4H), 2.31-2.03 (br m, 2H).

Poly(S-(3-(2-acetoxyethoxy)-2-hydroxypropyl)-L-homocysteine), 2c

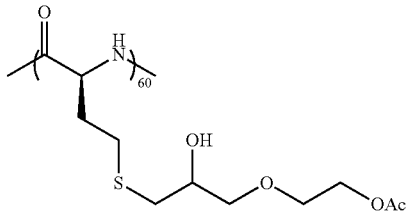

Prepared from 1c using Demethylation Procedure A.

$^1$H NMR (400 MHz, D_TFA, 25° C.): 4.94-4.68 (br m, 1H), 4.51-4.32 (br m, 1H), 4.40 (m, 2H), 4.32-4.12 (br m, 4H), 3.05-2.56 (br m, 4H), 2.17 (m, 5H).

Poly(S-(2-hydroxy-4,7,10-trioxaundecyl)-L-homocysteine), 2d

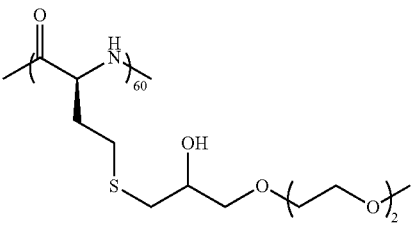

Prepared from 1d using Demethylation Procedure A.

$^1$H NMR (400 MHz, D$_2$O, 25° C.): 4.52-4.12 (br m, 1H), 4.12-3.88 (br m, 1H), 3.88-3.49 (br m, 10H), 3.41 (s, 3H), 3.07-2.59 (br m, 4H), 2.50-2.04 (br m, 2H).

Poly(S-(2-hydroxy-4,7,10-trioxadodecyl)-L-homocysteine), 2e

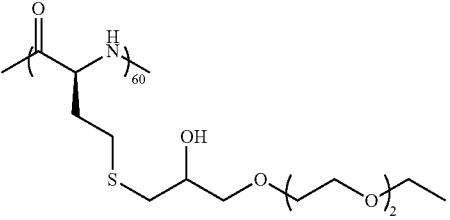

Prepared from 2e using Demethylation Procedure A.

$^1$H NMR (400 MHz, D$_2$O, 25° C.): 4.52-4.18 (br m, 1H), 4.09-3.90 (br m, 1H), 3.83-3.48 (br m, 12H), 3.19-2.58 (br m, 4H), 2.50-2.00 (br m, 2H), 1.25 (t, J=7.2 Hz, 3H).

Poly(S-(2-hydroxy-4,7,10,13-tetraoxatetradecyl)-L-homocysteine), 2f

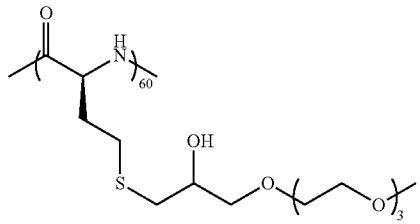

Prepared as described above.

Poly[(S-(2-hydroxy-4,7,10-trioxaundecyl)-L-homocysteine)$_{0.5}$-stat-(S-(2-hydroxy-4,7,10-trioxadodecyl)-L-homocystein)$_{0.5}$], 4b

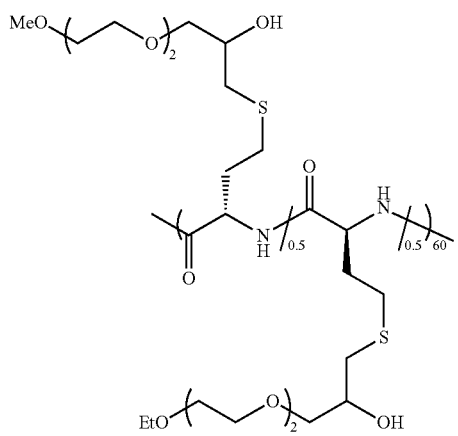

Prepared from 4a using Demethylation Procedure A, with the slight modification that potassium thioacetate (KSAc) was used instead of APDC.

$^1$H NMR (400 MHz, D$_2$O, 25° C.): 5.04-4.61 (br m, 1H), 4.33-4.14 (br m, 1H), 4.14-3.62 (br m, 11H), 3.55 (s, 1.5H), 3.13-2.44 (br m, 4H), 2.31-1.94 (br m, 2H), 1.29 (t, J=7.0 Hz, 1.5H).

Example 9: Helicity as a Function of pH for Exemplary Polymers

The helicity of exemplary ionic C$^H$ derivatives was measured by CD at 0.5 mg/mL in phosphate or tris buffer at 25° C. The results are provided in Table 8.

TABLE 8

Helicity as a Function of pH

| Label | R' | Helicity (%) at pH 5.5 | 7.0 | 9.0 |
|---|---|---|---|---|
| 16a | ~NH$_3^+$ Cl$^-$ | 27 | 35 | 72 |
| 16b | ~O~NH$_3^+$ Cl$^-$ | 47 | 70 | 77 |
| 17b | ~O~NH$_3^+$ Cl$^-$ | 42 | 57 | 64 |
| 16c | ~O~N$^+$H$_2$(i-Pr) Cl$^-$ | 42 | 61 | 81 |
| 16d | ~O~CH(NH$_3^+$Cl$^-$)C(O)NH$_2$ | 71 | 83 | 87 |
| 16e | ~O~CH(NH$_3^+$Cl$^-$)C(O)NH-i-Pr | 83 | 86 | 87 |
| 16f | ~O~CH$_2$C(O)O$^-$ Na$^+$ | 79 | 78 | 77 |
| 16g | ~O~CH$_2$CH(NH$_3^+$)C(O)O$^-$ | 70 | 70 | 71 |
| 17h | ~O~O~NH$_3^+$ Cl$^-$ | 54 | 74 | 75 |

Example 10: Helicity as a Function of Guanidinium Chloride Concentration for Exemplary Polymers The helicity of exemplary ionic C$^H$ derivatives was measured by CD at 0.5 mg/mL and pH 7.0 at varying concentrations of guanidinium chloride in phosphate or tris buffer at 25° C. The results are provided in Table 9.

TABLE 9

Helicity as a Function of [Guanidine]

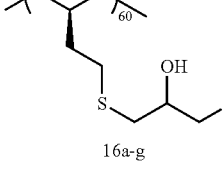

| Label | R' | Helicity (%) at [Guanidine] (M) | | | | |
|---|---|---|---|---|---|---|
| | | 0.0 | 1.0 | 2.0 | 3.0 | 4.0 |
| 16a | 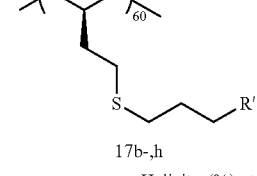 ⁺NH₃ Cl⁻ | 35 | 40 | 15 | 8 | 7 |
| 16b |  O ⁺NH₃ Cl⁻ | 70 | 58 | 42 | 18 | 9 |
| 17b |  O ⁺NH₃ Cl⁻ | 57 | 51 | 44 | 33 | 21 |
| 16c |  O ⁺NH₂ i-Pr Cl⁻ | 61 | 66 | 57 | 23 | 7 |
| 16d |  O NH₂ ⁺NH₃ Cl⁻ | 83 | 68 | 35 | 7 | 5 |
| 16e |  O NH-i-Pr ⁺NH₃ Cl⁻ | 87 | 79 | 57 | 39 | 15 |

TABLE 9-continued

Helicity as a Function of [Guanidine]

| Label | R' | Helicity (%) at [Guanidine] (M) | | | | |
|---|---|---|---|---|---|---|
| | | 0.0 | 1.0 | 2.0 | 3.0 | 4.0 |
| 16f | O O⁻ Na⁺ | 78 | 74 | 26 | 24 | 10 |
| 16g | O O⁻ ⁺NH₃ | 71 | 53 | 30 | 7 | 7 |
| 17h | O O ⁺NH₃ Cl⁻ | 74 | 66 | 11 | 9 | 8 |

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A polypeptide comprising one or more R—C$^H$ residues, wherein each R—C$^H$ residue in the polypeptide has the following structure:

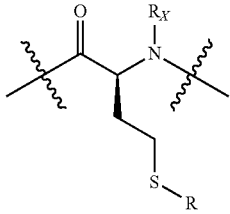
(I)

wherein:

R$_X$, independently for each R—C$^H$ residue, is H or alkyl; and

R, independently for each R—C$^H$ residue is:

i) a moiety with the following structure:

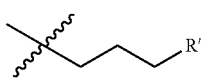

wherein R' is selected from alkoxy,

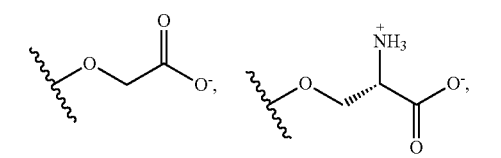

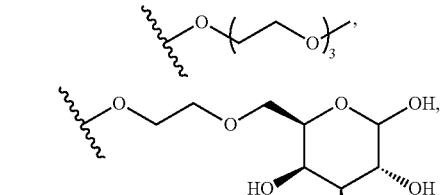

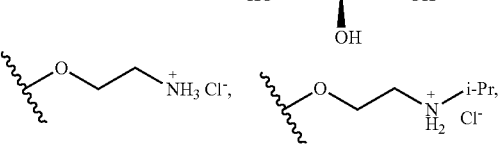

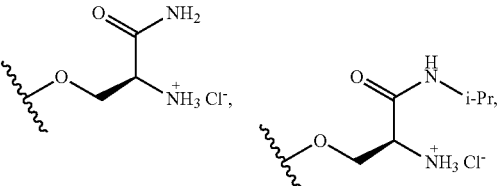

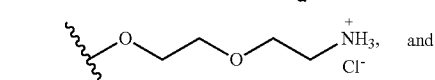

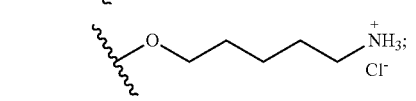

or ii) a moiety with the following structure:

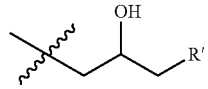

wherein R' is selected from alkoxy,

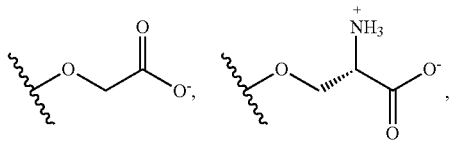

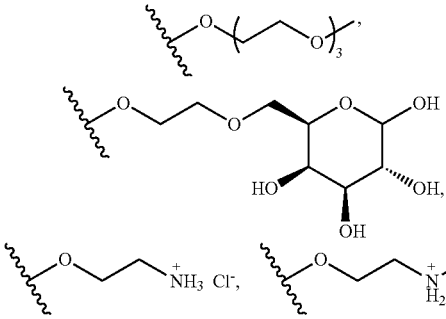

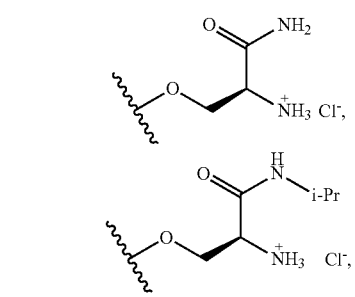

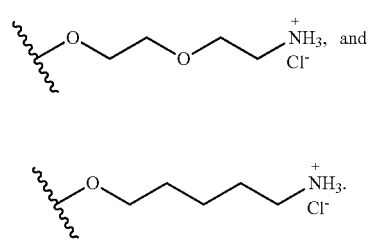

2. The polypeptide of claim 1, wherein the polypeptide is a homopolymer.

3. The polypeptide of claim 1, wherein the polypeptide is a heteropolymer.

4. The polypeptide of claim 1, wherein the polypeptide does not comprise a residue that is not an R—C$^H$ residue.

5. The polypeptide of claim 1, wherein the polypeptide comprises at least 4 residues or at least 10 residues.

6. The polypeptide of claim 1, wherein the polypeptide comprises at least 60 residues.

7. A polypeptide having the following structure:

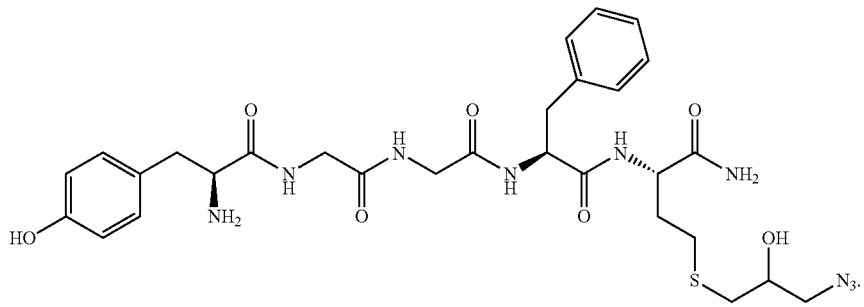 [SMILES: [N-]=[N+]=NCC(O)CSCC[C@H](NC(=O)[C@H](Cc1ccccc1)NC(=O)CNC(=O)CNC(=O)[C@@H](N)Cc1ccc(O)cc1)C(N)=O]

8. The polypeptide of claim 1, wherein R is a moiety with the following structure:

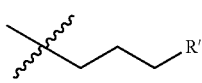

wherein R' is selected from alkoxy,

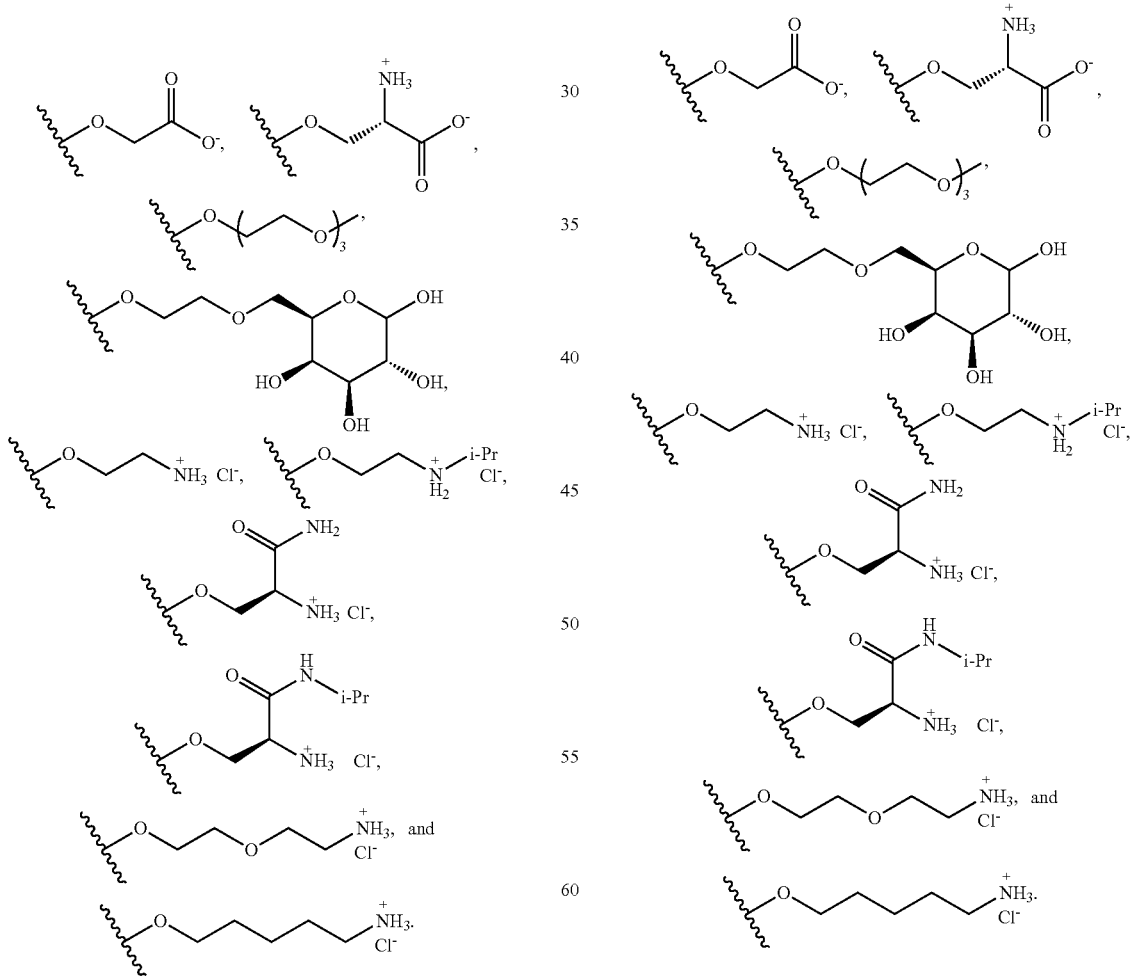

9. The polypeptide of claim 1, wherein R is a moiety with the following structure:

10. A polypeptide comprising one or more R—$C^H$ residues, wherein each R—$C^H$ residue in the polypeptide has the following structure:

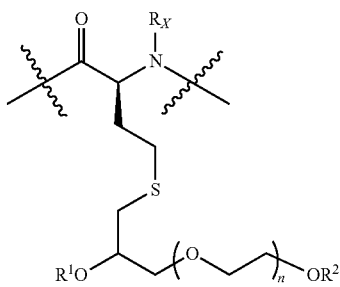

wherein:

$R_X$, independently for each R—$C^H$ residue, is H or alkyl:

$R^1$, independently for each R—$C^H$ residue, is selected from H, alkyl, acyl, and alkoxy-C(O)—;

$R^2$, independently for each R—$C^H$ residue, is selected from H, alkyl, acyl, and alkoxy-C(O)—; and n, independently for each R—$C^H$ residue, is an integer from 0-10.

11. The polypeptide of claim 10, wherein $R_X$ is H, $R^1$ is H; $R^2$ is H, $C_{1-3}$ alkyl, or Ac; and n is 1, 2, or 3.

12. A polypeptide comprising one or more R—$C^H$ residues, wherein each R—$C^H$ residue in the polypeptide has the following structure:

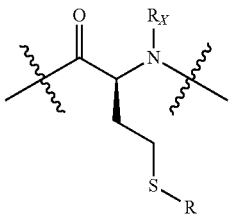 (I)

wherein:

$R_X$, independently for each R—$C^H$ residue, is H or alkyl:

R, independently for each R—$C^H$ residue, is alkyl:

provided that at least one R—$C^H$ residue is

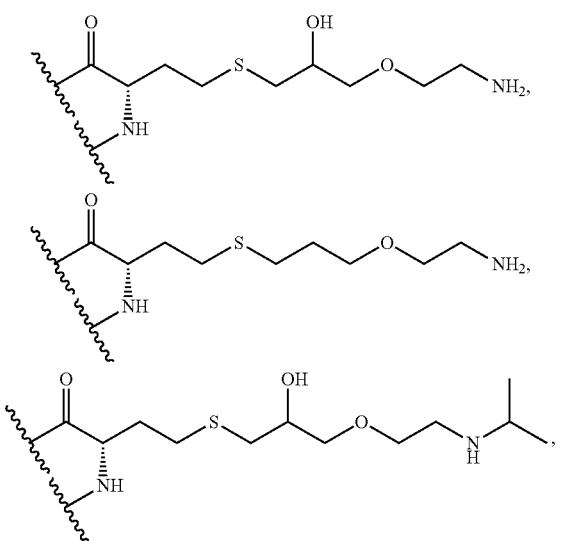

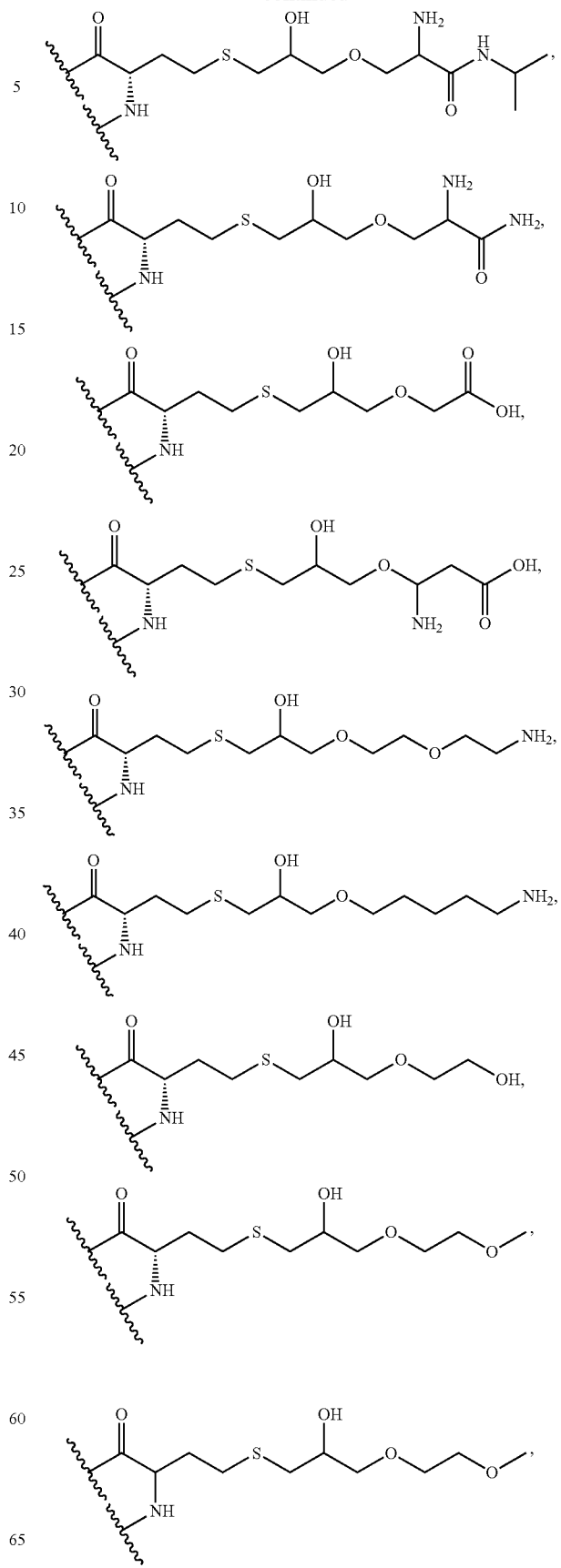

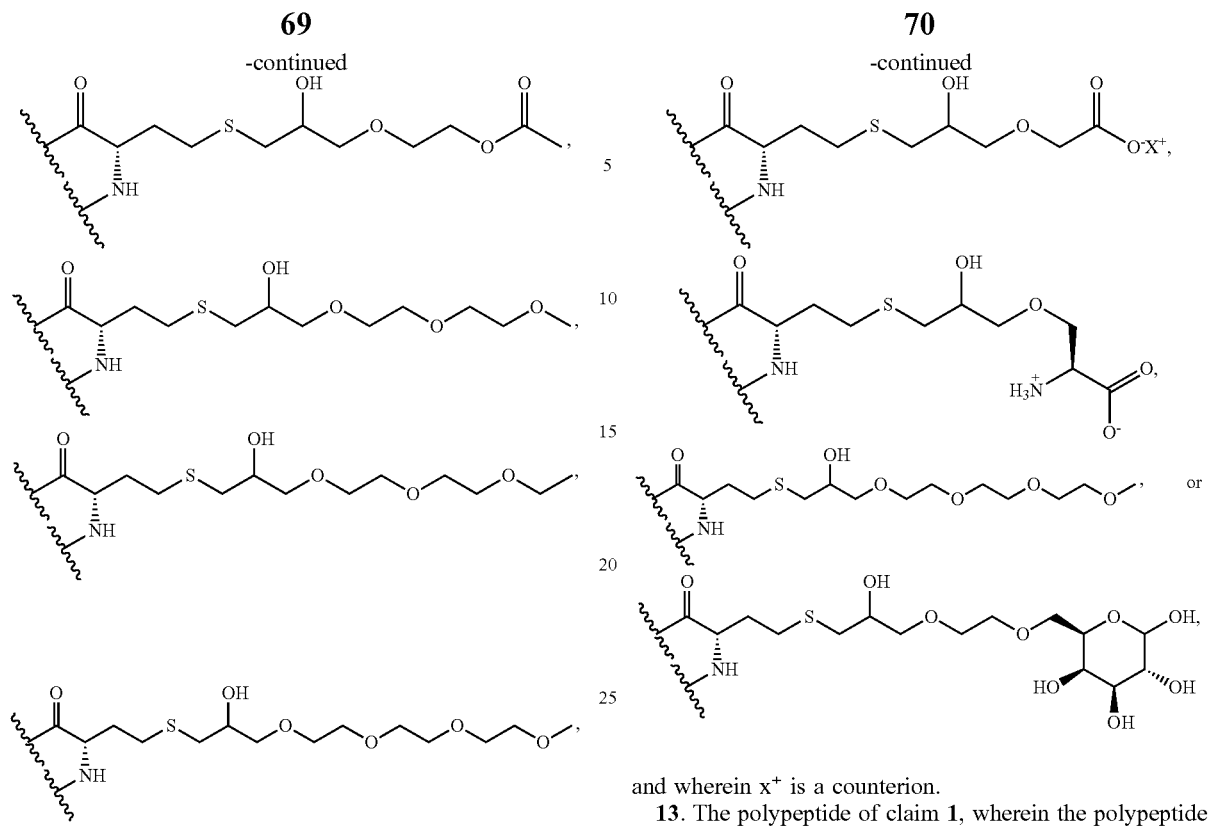
and wherein x⁺ is a counterion.
13. The polypeptide of claim 1, wherein the polypeptide is
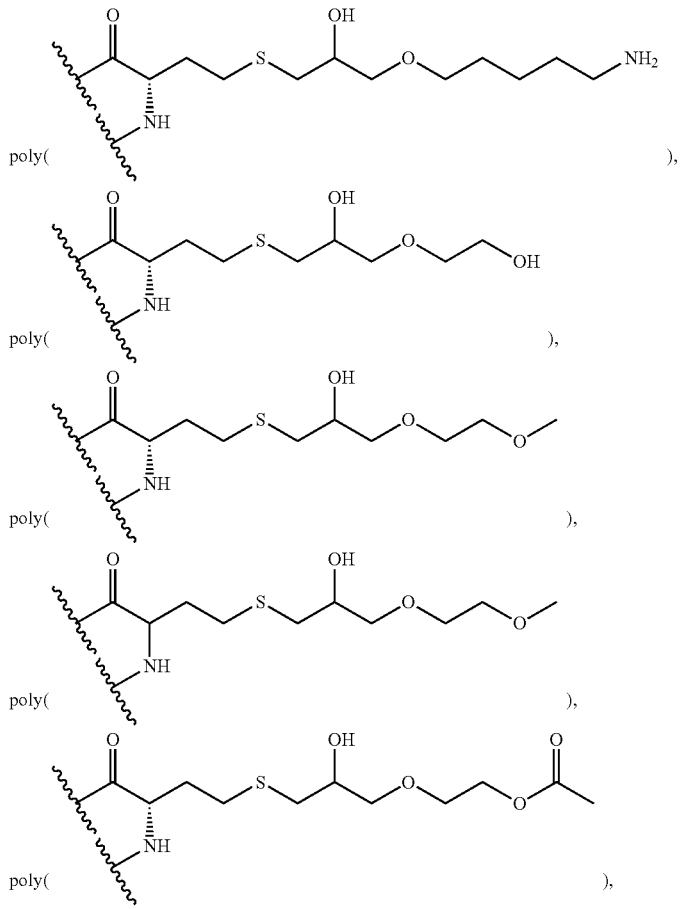

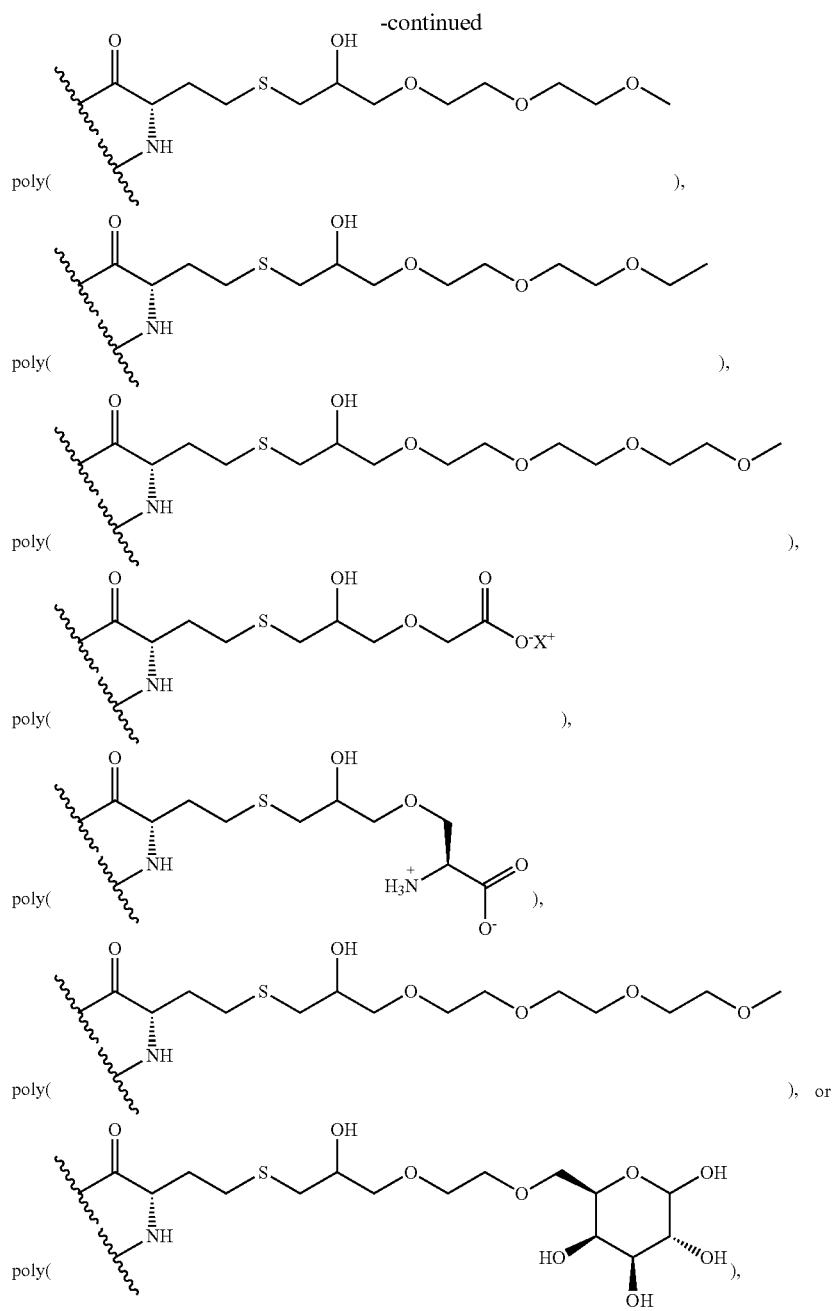
and wherein $X^+$ is a counterion.
14. The polypeptide of claim 1, further comprising at least one M residue and at least one $M^R$ residue, wherein the M and $M^R$ residues are no more than 10% of the M, $M^R$, and R—$C^H$ residues in the polypeptide.
* * * * *

UNITED STATES PATENT AND TRADEMARK OFFICE
CERTIFICATE OF CORRECTION

PATENT NO. : 11,732,008 B2
APPLICATION NO. : 16/096951
DATED : August 22, 2023
INVENTOR(S) : Timothy J. Deming et al.

Page 1 of 2

It is certified that error appears in the above-identified patent and that said Letters Patent is hereby corrected as shown below:

In the Claims

In Claim 13, Line 1, cancel the text beginning with "13. The polypeptide" to and ending "is a counterion." in Line 14, and insert the following claim:
--13. The polypeptide of claim 1, wherein the polypeptide is

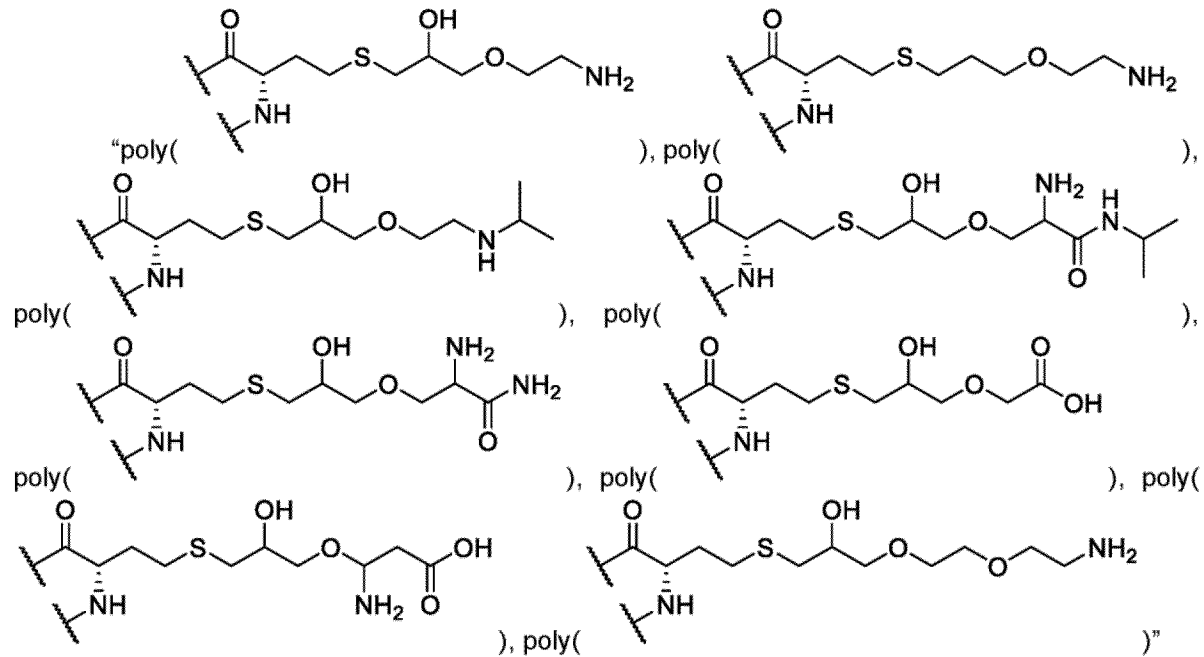

Signed and Sealed this
Twenty-third Day of April, 2024

Katherine Kelly Vidal
*Director of the United States Patent and Trademark Office*

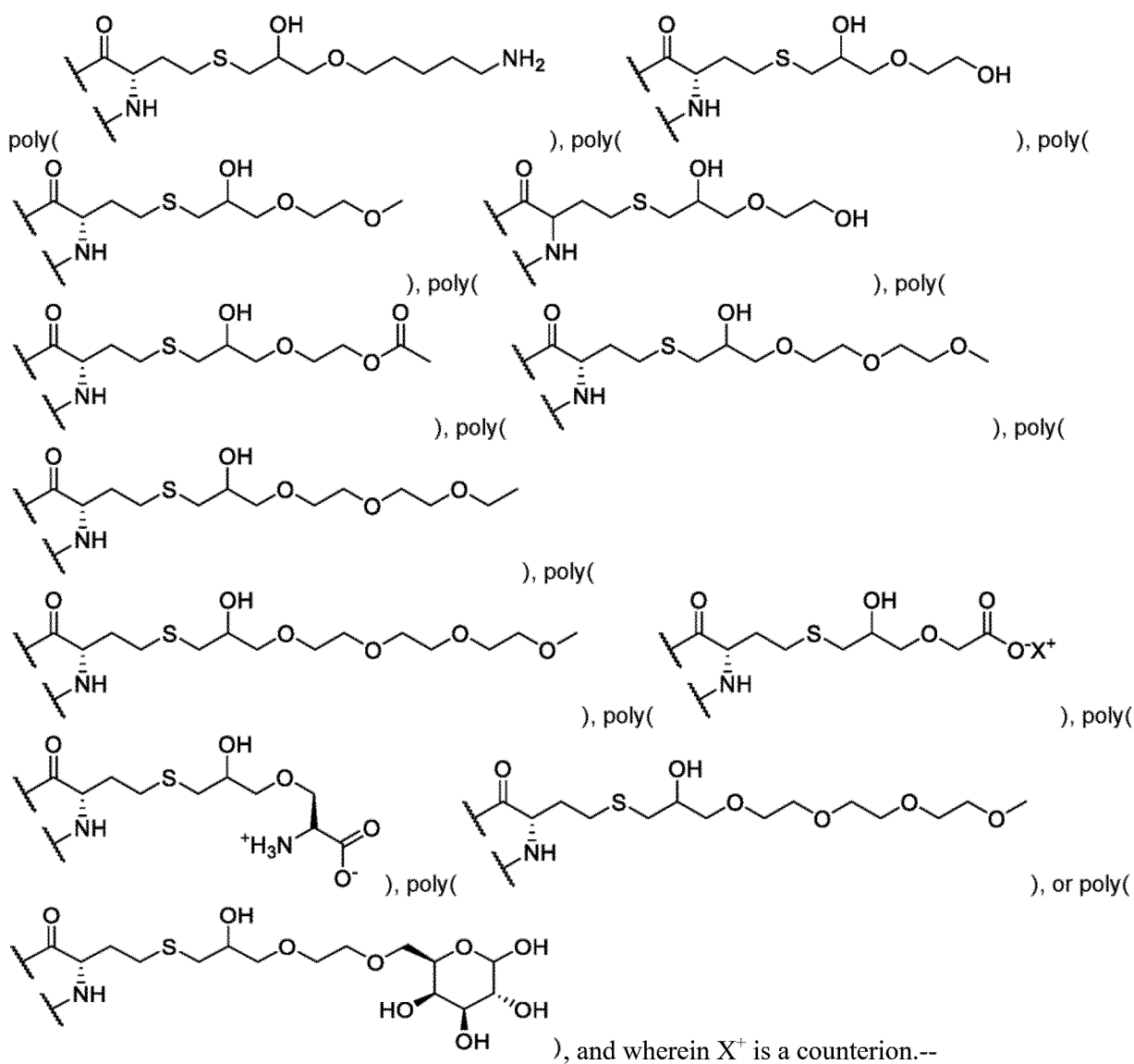
), and wherein $X^+$ is a counterion.--

SEQUENCE LISTING

```
<160> NUMBER OF SEQ ID NOS: 4

<210> SEQ ID NO 1
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Met Met Met Met Met Met Met Met Met Met Met Met Met Met Met
1               5                   10                  15
```

```
Met Met Met Met Met Met Met Met Met Met Met Met Met Met
        20                  25                  30

Met Met Met Met Met Met Met Met Met Met Met Met Met Met
        35                  40                  45

Met Met Met Met Met Met Met Met Met Met Met
        50                  55                  60

<210> SEQ ID NO 2
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(60)
<223> OTHER INFORMATION: Homocysteine

<400> SEQUENCE: 2

Cys Cys Cys Cys Cys Cys Cys Cys Cys Cys Cys Cys Cys Cys Cys Cys
1               5                   10                  15

Cys Cys Cys Cys Cys Cys Cys Cys Cys Cys Cys Cys Cys Cys
        20                  25                  30

Cys Cys Cys Cys Cys Cys Cys Cys Cys Cys Cys Cys Cys Cys
        35                  40                  45

Cys Cys Cys Cys Cys Cys Cys Cys Cys Cys Cys Cys
        50                  55                  60

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Gly Gly Phe Met
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Homocysteine

<400> SEQUENCE: 4

Tyr Gly Gly Phe Cys
1               5
```